US00RE49361E

(19) United States
(12) Reissued Patent
Bingham et al.

(10) Patent Number: US RE49,361 E
(45) Date of Reissued Patent: Jan. 10, 2023

(54) FUSED BICYCLIC (HETERO)AROMATIC COMPOUNDS USEFUL FOR THE TREATMENT OF CANCERS

(71) Applicant: JAZZ PHARMACEUTICALS IRELAND LIMITED, Dublin (IE)

(72) Inventors: Matilda Bingham, Macclesfield (GB); Richard Testar, Macclesfield (GB); Camille Gignoux, Macclesfield (GB)

(73) Assignee: Jazz Pharmaceuticals Ireland Limited, Dublin (IE)

(21) Appl. No.: 17/102,621

(22) Filed: Nov. 24, 2020

Related U.S. Patent Documents

Reissue of:
(64) Patent No.: 10,183,939
Issued: Jan. 22, 2019
Appl. No.: 15/509,952
PCT Filed: Sep. 11, 2015
PCT No.: PCT/GB2015/052640
§ 371 (c)(1),
(2) Date: Mar. 9, 2017
PCT Pub. No.: WO2016/038389
PCT Pub. Date: Mar. 17, 2016

(30) Foreign Application Priority Data

Sep. 12, 2014 (GB) ..... 1416186

(51) Int. Cl.
*C07D 471/04* (2006.01)
*A61K 31/4375* (2006.01)
*A61K 31/4439* (2006.01)
*A61K 45/06* (2006.01)
*C07D 405/14* (2006.01)

(52) U.S. Cl.
CPC ..... *C07D 471/04* (2013.01); *A61K 31/4375* (2013.01); *A61K 31/4439* (2013.01); *A61K 45/06* (2013.01); *C07D 405/14* (2013.01)

(58) Field of Classification Search
CPC ..... C07D 471/04; C07D 405/14; A61K 31/4375; A61K 31/4439; A61K 45/06; A61P 35/00; A61P 35/02; A61P 43/00
See application file for complete search history.

(56) References Cited

U.S. PATENT DOCUMENTS 5,698,550 A * 12/1997 Eggler ..... C07D 215/227 514/217.04

FOREIGN PATENT DOCUMENTS

| | | | |
|---|---|---|---|
| CN | 1690056 | A | 11/2005 |
| JP | 2009-519908 | A | 5/2009 |
| WO | WO-1999063974 | A2 | 12/1999 |
| WO | WO-2003/006452 | A1 | 1/2003 |
| WO | WO-2004/063191 | A1 | 7/2004 |
| WO | WO-2006/087229 | A1 | 8/2006 |
| WO | WO 2006/124874 | A2 | 11/2006 |
| WO | WO-2008/009079 | A3 | 5/2009 |
| WO | WO-2013097224 | A1 | 7/2013 |

OTHER PUBLICATIONS

Lewis et al., "The pharmacokinetics and metabolism of idazoxan in the rat," Xenobiotica, 1988, 18(5) pp. 519-532.
Gilchrist, T "Heterocyclic Chemistry" Addison-Wesley Longman NY 1992 excerpt.*
Search Report issued by Intellectual Property Office in corresponding Application No. GB1416186.3, dated May 26, 2015.

* cited by examiner

*Primary Examiner* — Jerry D Johnson
(74) *Attorney, Agent, or Firm* — Cooley LLP

(57) ABSTRACT

This invention relates to novel compounds. The compounds of the invention are kinase inhibitors. Specifically, the compounds of the invention are useful as inhibitors of Raf kinases, e.g., B-Raf and C-Raf. The invention also contemplates the use of the compounds for treating conditions treatable by the inhibition of Raf kinases, for example, cancer, sarcoma, melanoma, skin cancer, haematological tumors, lymphoma, carcinoma, and leukemia.

24 Claims, 1 Drawing Sheet

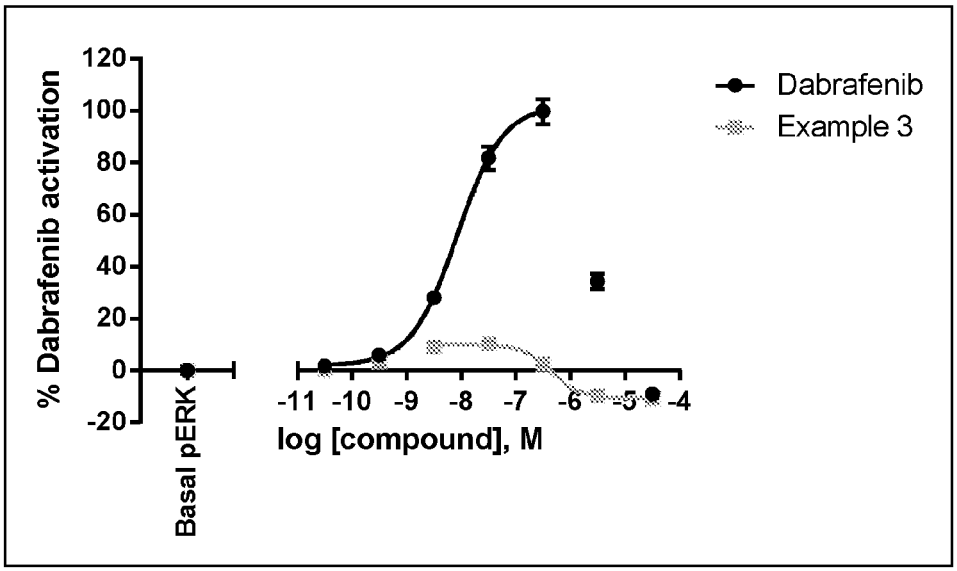
% Dabrafenib activation
120
100
80
60
40
20
0
-20
Basal pERK
-11 -10 -9 -8 -7 -6 -5 -4
log [compound], M
Dabrafenib
Example 3

FUSED BICYCLIC (HETERO)AROMATIC COMPOUNDS USEFUL FOR THE TREATMENT OF CANCERS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATIONS

This application is a § 371 national stage application based on Patent Cooperation Treaty Application serial number PCT/GB2015/052640, filed Sep. 11, 2015, which claims the benefit of priority to GB 1416186.3, filed Sep. 12, 2014.

This invention relates to compounds. More specifically, the invention relates to compounds useful as kinase inhibitors, for example RAF kinases such as B-RAF and C-RAF. In addition the invention contemplates processes to prepare the compounds and uses of the compounds.

BACKGROUND

Kinases are a class of enzyme that control the transfer of phosphate groups from phosphate donors, for example ATP, to specific substrates. Protein kinases are a subset of kinases and serine/threonine-protein kinase B-RAF is one such protein kinase. Serine/threonine-protein kinase B-RAF is more commonly known as B-RAF and throughout this application these two terms will be used interchangeably.

B-RAF is a member of the RAF kinase family, the other members of the family being A-RAF and C-RAF. Each of the RAF kinases is a serine/threonine-specific protein kinase, an enzyme that phosphorylates the hydroxyl group of serine or threonine residues within a protein. The RAF kinases are involved in the mitogen-activated protein kinase (MAPK) cascade, a key pathway involved in internal cell signalling responsible for cell division, cell proliferation, programmed cell death (apoptosis), cell differentiation, and embryonic development.

Defects in the MAPK pathway can affect the signalling within a cell and can lead to uncontrolled cell growth through deviant cell division and irregular cell death. Such defects in the MAPK pathway can be caused by mutations to the RAF kinases or aberrant expression of the RAF kinases, as such abnormalities associated with the RAF kinases, such as the known mutation B-RAF$^{V600E}$ can give rise to uncontrolled cell growth and consequently cancer.

Thus, controlling aberrant functioning of RAF kinases by small molecule inhibition presents a useful approach for the treatment of cancers.

A number of RAF inhibitors have been identified. Two such compounds are dabrafenib and vemurafenib. Dabrafenib is a B-RAF inhibitor indicated in the treatment of malignant melanoma and marketed by GlaxoSmithKline. Dabrafenib was approved for the treatment of malignant melanoma in May 2013 by the US FDA. Similarly, in August 2011 vemurafenib was approved for the treatment of melanoma by the US FDA. As with dabrafenib, vemurafenib is a B-RAF inhibitor, specifically of the B-RAF$^{V600E}$ mutation.

RAF inhibitors such as dabrafenib and vemurafenib have been approved for the treatment of unresectable and metastatic B-RAF-mutant melanoma, but these agents lack efficacy in B-RAF-mutant colorectal cancer (CRC), partly because of EGFR-mediated feedback reactivation of the MAPK pathway. Furthermore, RAF inhibitor treatment of RAS-mutant, B-RAF$^{WT}$-melanomas has been associated with other skin cancers, such as cutaneous squamous cell carcinoma due to MAPK pathway paradoxical activation. There is therefore a clinical need for novel agents targeting the MAPK pathway that do not have the undesirable properties of EGFR-mediated feedback reactivation of the MAPK pathway and MAPK pathway paradoxical activation.

A number of patents have been published describing B-RAF inhibitors. One such publication is WO 2012/125981 which describes a compound having a structure related to dabrafenib. Both compounds contain a central 5-membered heterocycle flanked by two substituted 6-membered (or higher) ring systems. In addition to WO 2012/125981, B-RAF inhibitors have also been disclosed in WO 2012/016993, WO 2011/085269, WO 2011/025927, WO 2011/092088 and WO 2011/023773, for example.

In addition to these documents fused tricyclic compounds as RAF kinase inhibitors were recently disclosed in WO 2013/097224. In addition, US 2010/0197924 discloses aminotetralin compounds with kinase inhibitory activity, specifically RAF kinase inhibitory activity and WO 2007/067444 discloses bicyclic compounds for the same purpose.

It is an aim of certain embodiments of this invention to provide new cancer treatments. In particular, it is an aim of certain embodiments of this invention to provide compounds which have comparable activity to existing cancer treatments, ideally better activity.

Certain embodiments of this invention aim to provide for compounds which are suitable for the treatment of cancers which have been identified as containing a mutation of the BRAF kinase, for example human melanomas, thyroid cancer, Barret's adenocarcinoma, biliary tract carcinomas, breast cancer, cervical cancer, cholangiocarcinoma, central nervous system tumors, glioblastomas, astrocytomas, ependymomas, colorectal cancer, large intestine colon cancer, gastric cancer, carcinoma of the head and neck, hematologic cancers, leukaemia, acute lymphoblastic leukaemia, myelodysplastic syndromes, chronic myelogenous leukaemia, Hodgkin's lymphoma, non-Hodgkin's lymphoma, megakaryoblastic leukaemia, multiple myeloma, hepatocellular carcinoma, lung cancer, ovarian cancer, pancreatic cancer, pituitary adenoma, prostate cancer, renal cancer, sarcoma, uveal melanoma and skin cancer. Certain embodiments of this invention aim to provide for compounds which are suitable for the treatment of cancers which have been identified as containing the BRAF$^{V600E}$ mutation. For example BRAF$^{V600E}$ melanoma, BRAF$^{V600}$E colorectal cancer, BRAF$^{V600E}$ papillary thyroid cancers, BRAF$^{V600E}$ low grade serous ovarian cancers, BRAF$^{V600E}$ glioma, BRAF$^{V600E}$ hepatobiliary cancers, BRAF$^{V600E}$ hairy cell leukaemia, BRAF$^{V600E}$ non-small cell cancer, and BRAF$^{V600E}$ pilocytic astrocytoma.

RAF inhibitor treatment of RAS-mutant, BRAF$^{WT}$-melanomas has been associated with other skin cancers, such as cutaneous squamous cell carcinoma due to MAPK pathway paradoxical activation. There is therefore a clinical need for novel agents targeting the MAPK pathway that do not have these undesirable properties. Certain embodiments of this invention aim to provide compounds which show reduced side effects. For example, certain embodiments of this invention aim to provide for compounds which show reduced paradoxical activation of the MAPK pathway in $BRAF^{WT}$ cells and which inhibit the MAPK pathway at therapeutically relevant concentrations.

Certain embodiments of this invention aim to provide for compounds which show sustained MAPK pathway inhibition over 24 hours in cell lines known to undergo reactivation of the MAPK pathway following treatment with the RAF inhibitors dabrafenib and vemurafenib. Certainembodiments also aim to reduce paradoxical activation of MAPK pathway compared to dabrafenib and/or vemurafenib.

It is an aim of certain embodiments of this invention to provide compounds which exhibit reduced cytotoxicity relative to prior art compounds and existing therapies.

Another aim of certain embodiments of this invention is to provide compounds having a convenient pharmacokinetic profile and a suitable duration of action following dosing. A further aim of certain embodiments of this invention is to provide compounds in which the metabolised fragment or fragments of the drug after absorption are GRAS (Generally Regarded As Safe).

Certain embodiments of the present invention satisfy some or all of the above aims.

BRIEF SUMMARY OF THE DISCLOSURE

In an aspect of the invention there is provided a compound of formula (I):

(I)

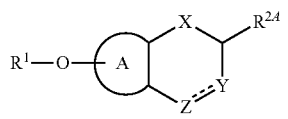

wherein:

A is a phenyl, pyridyl, pyridazinyl, pyrimidinyl, pyrazinyl or thiophenyl ring which is substituted or unsubstituted, and when substituted A contains 1 to 3 substituents independently selected from: halo, =O, —CN, $C_{1-4}$ alkyl, $C_{1-4}$ haloalkyl, $C_{3-6}$ cycloalkyl, $—OR^A$, $—NR^AR^B$, $SO_2R^A$ and $SOR^A$;

$R^1$ is a substituted or unsubstituted heterocyclic moiety which either contains 5 or 6 atoms in a single ring or 8, 9, 10 or 11 atoms in a fused bicyclic ring system, when substituted $R^1$ contains 1 to 4 substituents independently selected from: halo, $—OR^A$, $—NR^AR^B$, =O, $—OC(O)R^C$, $—C(O)R^C$, $—C(O)OR^A$, $—NR^AC(O)R^C$, $—C(O)NR^AR^B$, $—SO_2R^C$, $—SOR^C$, $—NR^ASO_2R^C$, $—SO_2NR^AR^B$, —CN, $C_{1-4}$ alkyl, $C_{1-4}$ haloalkyl and $C_{3-5}$ cycloalkyl;

X is N, O or S;

Y is $—CR^{2B}W$ or —CW;

W represents: $-het^1-R^3$ or $-het^2$, in which $het^1$ is a five or six membered carbocyclic ring or heterocyclic ring, and $het^2$ is a carbocyclic or heterocyclic ring system containing 8, 9 or 10 atoms in a fused bicyclic ring system; and in which each of $het^1$ and $het^2$ may be independently unsubstituted or substituted and contain 1 or 2 substituents independently selected at each occurrence from: halo, $—OR^A$, —CN, $C_{1-4}$ alkyl, $C_{1-4}$ haloalkyl, $C_{3-6}$ cycloalkyl, in which the aforementioned alkyl, haloalkyl and cycloalkyl groups may themselves also be unsubstituted or substituted with 1 to 3 groups independently selected from: $—OR^A$, —CN, $—NR^AR^B$;

Z is N, O, S, $—CR^{2C}$, $—CR^{2C}R^{2D}$;

$R^{2A}$, $R^{2B}$, $R^{2C}$ and $R^{2D}$ are each independently selected at each occurrence from: H, halo, $—OR^A$, —CN, $C_{1-4}$ alkyl, $C_{1-4}$ haloalkyl and $C_{3-6}$ cycloalkyl;

$R^3$ is selected from substituted or unsubstituted: $C_{1-6}$ alkyl, $C_{1-6}$ haloalkyl, a carbocyclic moiety or a heterocyclic moiety, wherein the carbocyclic moiety and heterocyclic moiety either contain 5 or 6 atoms in a single ring or 8, 9 or 10 atoms in a fused bicyclic ring system, and when substituted $R^3$ contains 1 to 4 substituents independently selected from: halo, $—OR^A$, $—NR^AR^B$, $—SO_2R^C$, $—SOR^C$, —CN, $C_{1-4}$ alkyl, $C_{1-4}$ haloalkyl, $C_{3-6}$ cycloalkyl in which the aforementioned alkyl, haloalkyl and cycloalkyl groups may themselves also be unsubstituted or substituted with 1 to 3 groups independently selected from: $—OR^A$, —CN, $—SOR^C$, and $—NR^AR^B$;

$R^A$ and $R^B$ are each independently selected from H, $C_{1-4}$ alkyl and $C_{1-4}$ haloalkyl; and $R^C$ is selected from $C_{1-4}$ alkyl and $C_{1-4}$ haloalkyl.

The present invention provides pharmaceutically acceptable salts of compounds of formula (I) and all other formulae disclosed herein.

$Het^1$ may be a five or six membered cycloalkyl or heterocyclic ring, and $het^2$ may be a carbocyclic or heterocyclic ring system containing 8, 9 or 10 atoms in a fused bicyclic ring system Preferably, $het^1$ is a five or six membered heterocyclic ring and $het^2$ is a heterocyclic ring system containing 8, 9 or 10 atoms in a fused bicyclic ring system.

Ring A is fused to the ring containing X, Y and Z. The two fused rings share two carbon atoms at the point of fusion, as would be understood by the person skilled in the art.

In embodiments the compound of formula (I) is a compound according to formula (Ia)

(Ia)

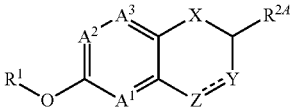

wherein $A^1$, $A^2$ and $A^3$ are each independently selected from $CR^4$ or N, and $R^4$ is independently selected at each occurrence from: halo, $—OR^A$, $—NR^AR^B$, =O, —CN, $C_{1-4}$ alkyl, $C_{1-4}$ haloalkyl and $C_{3-6}$ cycloalkyl.

In preferred embodiments A is phenyl. Thus, in an embodiment, there is provided a compound of formula (II):

(II)

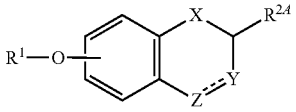

In preferred embodiments, there is provided a compound of formula (IIa):

(IIa)

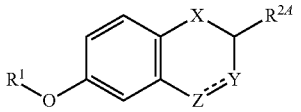

In embodiments X is O or S. Preferably, X is O.

In certain embodiments Z is O, $CR^{2C}$ or $CR^{2C}R^{2D}$. In certain embodiments Z is O and Y is $CR^{2B}W$. In certain embodiments Z is $CR^{2C}R^{2D}$ and Y is $CR^{2B}W$. In certain embodiments Z is $CR^{2C}$ and Y is CW.

In certain embodiments X is O, Z is $CR^{2C}R^{2D}$ and Y is $CR^{2B}W$. Thus, there is provided a compound according to formula (IIIa):

(IIIa)

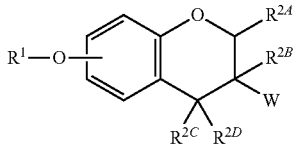

In certain embodiments X is O, Z is $CR^{2C}$ and Y is CW. Thus, there is provided a compound according to formula (IIIb):

(IIIb)

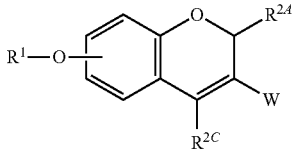

In certain embodiments X is O, Z is O and Y is $CR^{2B}W$. Thus, there is provided a compound according to formula (IIIc):

(IIIc)

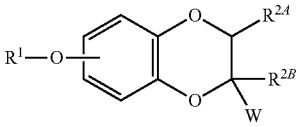

In certain embodiments the compound of formulae (IIIa) and (IIIc) may be single enantiomers. For example, compounds of formula (IIIa) may be compounds of formula (IId) or (IIIe) and compounds of formula (IIIc) may be compounds of formula (IIIf) and (IIIg):

(IIId)

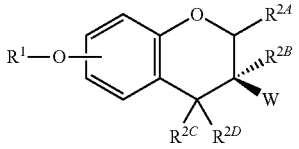

(IIIe)

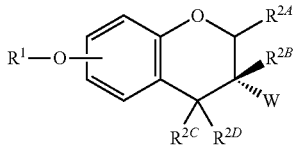

(IIIf)

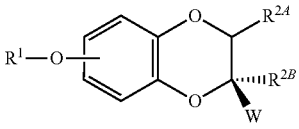

-continued (IIIg)

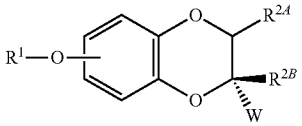

The central bicyclic ring system of the compound of formula (IIIa) is a chromane ring. The central bicyclic ring system of the compound of formula (IIIb) is a chromene ring. The central bicyclic ring system of the compound of formula (IIIc) is a dihydrobenzodioxine ring. Each of the central bicyclic ring systems are substituted with —O—$R^1$. The atoms of each of the central bicyclic groups are numbered as illustrated below.

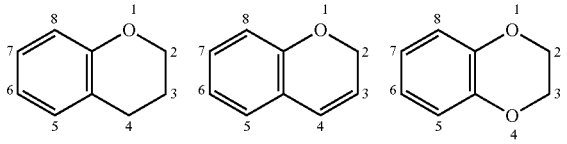

The —O—$R^1$ substituent on the chromane, chromene or dihydrobenzodioxine of formulae (IIIa), (IIIb) and (IIIc) respectively may be substituted at positions 5, 6, 7, or 8. Preferably —O—$R^1$ is substituted at position 6. When —O$R^1$ is substituted at position 6 of the chromane, chromene or dihydrobenzodioxine of formulae (IIIa), (IIIb) and (IIIc) respectively there is provided a compound of formulae (IVa), (IVb) and (IVc):

(IVa)

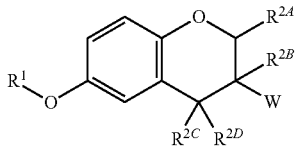

(IVb)

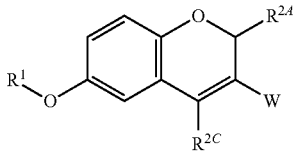

(IVc)

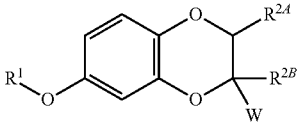

In an embodiment the compounds of the invention are single enantiomers. Thus, as indicated below, the compounds of the present invention may be a compound of formulae (IVd), (IVe), (IVf) or (IVg):

(IVd)

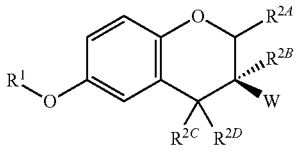

(IVe)

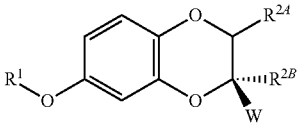

(IVf)

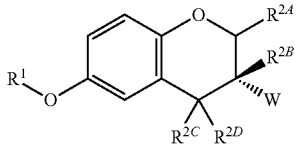

(IVg)

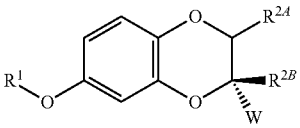

In a preferred embodiment $R^{2A}$, $R^{2B}$, $R^{2C}$ and $R^{2D}$ are each H. It is particularly preferred that $R^{2A}$, $R^{2B}$, $R^{2C}$ and $R^{2D}$ are each H in the compounds of formulae (IVa), (IVb), (IVc), (IVd), (IVe), (IVf) and (IVg) as appropriate.

$R^1$ may be selected from substituted or unsubstituted: pyridyl, pyridazinyl, pyrimidinyl, pyrazinyl, indolyl, isoindolyl, indolinyl, isoindolinyl, quinolinyl, tetrahydroquinolinyl, dihydroquinolinyl, quinolinone-yl, tetrahydroquinolinone-yl, dihydroquinolinone-yl, isoquinolinyl, tetrahydroisoquinolinyl, dihydroisoquinolinyl, isoquinolinone-yl, tetrahydroisoquinolinone-yl, dihydroisoquinolinone-yl, napthyridinyl, oxo-napthyridinyl, dihydronappthyridinyl, tetrahydronaphthyridinyl, oxotetrahydronaphthyridinyl, dihydropyrrolopyridinone (optionally a 1,3-dihydropyrrolopyridinone) and oxo-dihydro-H-naphthyridinyl. Preferably, $R^1$ is substituted or unsubstituted pyridyl, substituted or unsubstituted oxo-dihydro-H-naphthyridinyl, or substituted or unsubstituted dihydropyrrolopyridinone (optionally a 1,3-dihydropyrrolopyridinone). Further preferably, $R^1$ is methylpyridyl or oxodihydro-H-naphthyridinyl.

In embodiments $R^1$ is a substituted or unsubstituted heterocyclic moiety which either contains 6 atoms in a single ring or 10 atoms in a fused bicyclic ring system. $R^1$ may be a substituted or unsubstituted heterocyclic moiety, wherein the heterocyclic moiety is a 6 membered aromatic ring or a fused bicyclic ring system that is unsaturated or aromatic containing 10 atoms. Optionally, the heterocyclic moiety contains 1, 2 or 3 heteroatoms selected from N, O or S. Preferably, the heterocyclic moiety contains 1 or 2 nitrogen atoms.

When $R^1$ is substituted it is preferably substituted with halo, —$OR^A$, —$NR^AR^B$, =O, —OCN, $C_{1-4}$ alkyl, $C_{1-4}$ haloalkyl, —$NR^AC(O)R^C$, —$C(O)NR^AR^B$, —$NR^ASO_2R^C$ or —$SO_2NR^AR^B$. Preferably $R^1$ is substituted with —$NR^AC(O)R^C$, —$C(O)NR^AR^B$, —$NR^ASO_2R^C$ or —$SO_2NR^AR^B$.

In preferred embodiments when $R^1$ is substituted it is preferably substituted with fluoro, chloro, —OH, —$NH_2$, —OMe, —NHMe, —$NMe_2$, =O, —CN, methyl, trifluoromethyl, —NHC(O)Me, —NMeC(O)Me, —NHC(O)Et, —NMeC(O)Et, —$C(O)NH_2$, —C(O)NHMe, —$C(O)NMe_2$, —C(O)NHEt, —$NHSO_2Me$, —$NMeSO_2Me$, —$SO_2NH_2$, —$SO_2NHMe$, —$SO_2NMe_2$. Preferably $R^1$ is substituted with methyl or =O.

$R^1$ may be selected from substituted or unsubstituted: pyridyl, pyridazinyl, pyrimidinyl, pyrazinyl, quinolinyl, tetrahydroquinolinyl, dihydroquinolinyl, quinolinone-yl, tetrahydroquinolinone-yl, dihydroquinolinone-yl, isoquinolinyl, tetrahydroisoquinolinyl, dihydroisoquinolinyl, isoquinolinone-yl, tetrahydroisoquinolinone-yl, dihydroisoquinolinone-yl, napthyridinyl, oxo-napthyridinyl, dihydronappthyridinyl, tetrahydronaphthyridinyl, oxotetrahydronaphthyridinyl, dihydropyrrolopyridinone (optionally a 1,3-dihydropyrrolopyridinone), and oxo-dihydro-H-naphthyridinyl. Preferably, $R^1$ is substituted or unsubstituted pyridyl, dihydropyrrolopyridinone (optionally a 1,3-dihydropyrrolopyridinone) or substituted or unsubstituted oxo-dihydro-H-naphthyridinyl. Further preferably, $R^1$ is methylpyridyl or oxo-dihydro-H-naphthyridinyl.

In an embodiment, there is provided a compound of formulae (I), (II), (III) or (IV) wherein $R^1$ is methylpyridyl or oxo-dihydro-H-naphthyridinyl. For example, there is provided a compound of formula (IVa) wherein $R^1$ is methylpyridyl or oxo-dihydro-H-naphthyridinyl and $R^{2A}$, $R^{2B}$, $R^{2C}$ and $R^{2D}$ are each H. Thus, in an embodiment there is provided a compound of formulae (Va) and (Vb):

(Va)

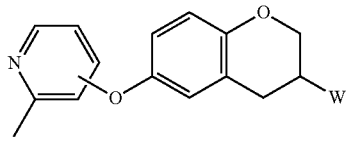

(Vb)

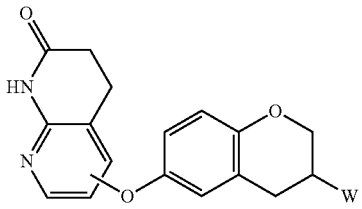

$Het^1$ and $het^2$ may be substituted or unsubstituted. $Het^1$ and $het^2$ may not be substituted with an oxo group, for example pyrollidinone is not a $het^1$ group and purinone is not a $het^2$ group because the groups contain a substiuted oxo group. In an embodiment $het^2$ is not purinone.

In embodiments, W represents -$het^1$-$R^3$ or -$het^2$, wherein $het^1$ is a substituted or unsubstituted five membered carbocyclic ring or heterocyclic ring, and $het^2$ is a substituted or unsubstituted carbocyclic or heterocyclic ring system, containing 8, 9 or 10 atoms in a fused bicyclic ring system.

In embodiments, W represents -$het^1$-$R^3$ or -$het^2$, wherein $het^1$ is a substituted or unsubstituted five membered heterocyclic ring, and $het^2$ is a substituted or unsubstituted heterocyclic ring system, containing 8, 9 or 10 atoms in a fused bicyclic ring system.

In embodiments, W represents -$het^1$-$R^3$ or -$het^2$, wherein $het^1$ is represented by a group selected from substituted or unsubstituted: $C_{5-6}$ cycloalkyl, $C_6$ aryl, $C_{5-6}$ heterocycloalkyl or $C_{5-8}$ heteroaryl, and $het^2$ is represented by a group selected from substituted or unsubstituted $C_{8-10}$ cycloalkyl, $C_{10}$ aryl, $C_{8-10}$ heterocycloalkyl or $C_{8-10}$ heteroaryl.

In embodiments, W represents -$het^1$-$R^3$ or -$het^2$, wherein $het^1$ is represented by a group selected from substituted or unsubstituted: $C_{5-6}$ cycloalkyl, $C_{5-6}$ heterocycloalkyl or $C_{5-6}$ heteroaryl, and $het^2$ is represented by a group selected from substituted or unsubstituted $C_{8-10}$ cycloalkyl, $C_{10}$ aryl, $C_{8-10}$ heterocycloalkyl or $C_{8-10}$ heteroaryl.

$Het^1$ may be a five or six membered heterocyclic ring, and $het^2$ may be a heterocyclic ring system containing 8, 9 or 10 atoms in a fused bicyclic ring system Preferably, $het^1$ is represented by $C_{5-6}$ heteroaryl and $het^2$ is represented by $C_{8-10}$ heteroaryl. Further preferably, $het^1$ is represented by $C_5$ heteroaryl.

In any of the embodiments described herein $het^1$ may be a five membered carbocyclic ring or heterocyclic ring (preferably heterocyclic) which is unsubstituted or substituted and $het^2$ may be a 9 membered carbocyclic or heterocyclic bicyclic ring system (preferably heterocyclic) which is unsubstituted or substituted.

In embodiments $het^2$ may be a bicyclic ring system with one of the rings of the bicyclic ring system being a five membered ring. Optionally, the five membered ring may be bonded to the ring containing X, Y and Z, for example the five membered ring may be bonded to the chromane, chromene or dihydrobenzodioxine of formulae (IIIa), (IIIb) and (IIIc) respectively.

In embodiments $het^1$ and $het^2$ are unsubstituted.

$Het^1$ may be represented by substituted or unsubstituted: pyrrole, furan, thiophene, pyrazole, imidazole, oxazole, isoxazole, thiazole, isothiazole, oxadiazole, thiadiazole and triazole, and $het^2$ may be represented by substituted or unsubstituted: indoline, isoindoline, benzodioxane, benzofurane, isobenzofurane, benzothiophene, isobenzothiophene, benzodioxolane, indazole, indazoline, benzimidazole, benzimidazoline, benzthiazole, benzoisothiazole, chromane, isochromane, tetraline, quinoline, isoquinoline, tetrahydroquinoline, tetrahydroisoquinoline and tetrahydroquinoxaline. Preferably, $het^1$ is represented by substituted or unsubstituted: pyrazole, imidazole or oxadiazole and $het^2$ is represented by substituted or unsubstituted benzimidazole.

In an embodiment there are provided compounds wherein W represents -$het^1$-$R^3$ and $het^1$ is represented by substituted or unsubstituted: pyrazole, imidazole or oxadiazole. In an alternative embodiment there are provided compounds wherein W represents -$het^2$ and $het^2$ is represented by substituted or unsubstituted benzimidazole.

In an embodiment there are provided compounds of formulae (IIIa), (IIIb) and (IIIc), wherein W represents -$het^1$-$R^3$ and $het^1$ is represented by substituted or unsubstituted: pyrazole, imidazole or oxadiazole. In an alternative embodiment there are provided compounds of formulae (Ilila), (IIIb) and (IIIc), wherein W represents -$het^2$ and $het^2$ is represented by substituted or unsubstituted benzimidazole.

In an embodiment there are provided compounds of formulae (IVa), (IVb) and (IVc), wherein W represents -$het^1$-$R^3$ and $het^1$ is represented by substituted or unsubstituted: pyrazole, imidazole or oxadiazole. In an alternative embodiment there are provided compounds of formulae (IVa), (IVb) and (IVc), wherein W represents -$het^2$ and $het^2$ is represented by substituted or unsubstituted benzimidazole.

In an embodiment the compounds according to formula (I) are compounds of formulae (VIa), (VIb), (VIc), (VId) or (VIe):

(VIa)

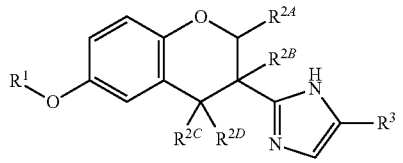

(VIb)

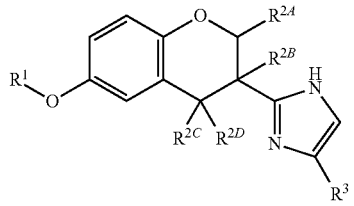

(VIc)

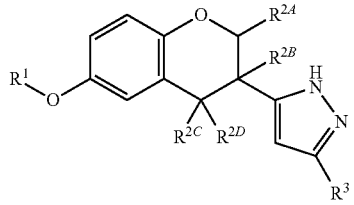

(VId)

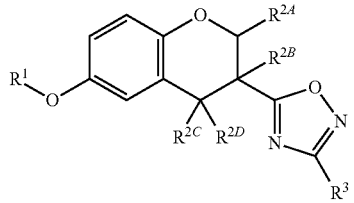

(VIe)

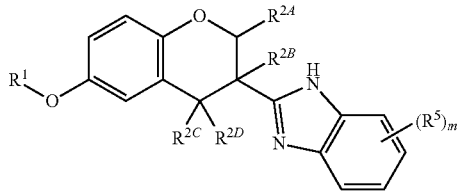

wherein m is selected from 0, 1 or 2; and $R^5$ is independently selected at each occurrence from: halo, —$OR^A$, $C_{1-4}$ alkyl, $C_{1-4}$ haloalkyl and $C_{3-6}$ cycloalkyl.

In an embodiment the compounds according to formula (I) are compounds of formulae (VIf), (VIg), (VIh), (VIi) or (VIj):

(VIf)

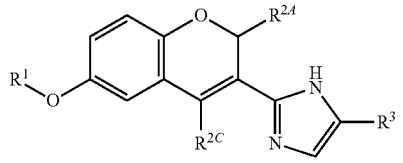

-continued (VIg)

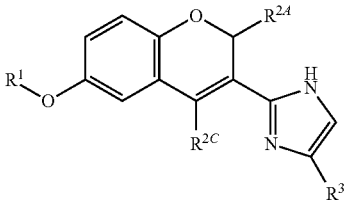

(VIh)

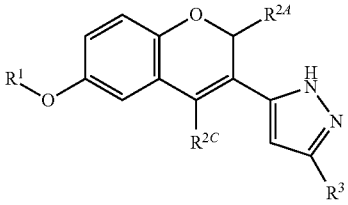

(VIi)

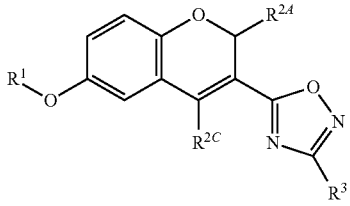

(VIj)

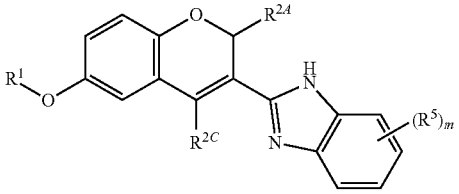

wherein m is selected from 0, 1 or 2; and $R^5$ is independently selected at each occurrence from: halo, —$OR^A$, $C_{1-4}$ alkyl, $C_{1-4}$ haloalkyl and $C_{3-6}$ cycloalkyl.

In an embodiment the compounds according to formula (I) are compounds of formulae (VIk), (VIm), (VIn), (VIo) or (VIp):

(VIk)

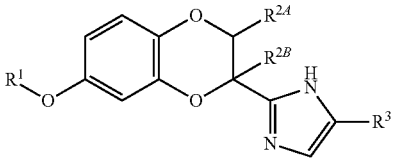

(VIm)

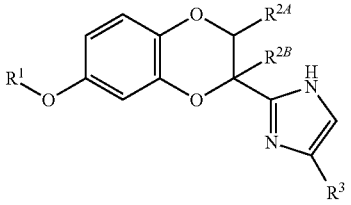

-continued (VIn)

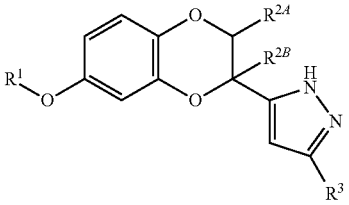

(VIo)

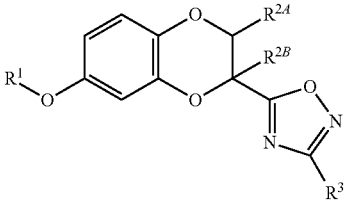

(VIp)

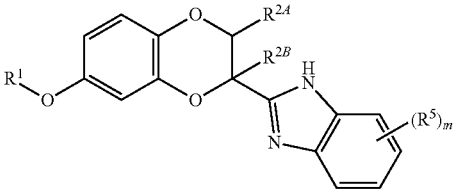

wherein m is selected from 0, 1 or 2; and $R^5$ is independently selected at each occurrence from: halo, —$OR^A$, $C_{1-4}$ alkyl, $C_{1-4}$ haloalkyl and $C_{3-6}$ cycloalkyl.

In an embodiment there is provided compounds of formulae (VIa), (VIb), (VIc), (VId), (VIe), (VIf), (VIg), (VIh), (VIi), (VIj) (VIk), (VIm), (VIn), (VIo) or (VIp).

In a preferred embodiment of the compounds of (VIa), (VIb), (VIc), (VId), (VIe), (VIf), (VIg), (VIh), (VIi), (VIj) (VIk), (VIm), (VIn), (VIo) or (VIp), $R^{2A}$, $R^{2B}$, $R^{2C}$ and $R^{2D}$ (as appropriate) are each H.

In an embodiment m is 0 or 1. In an embodiment $R^5$ is halo, preferably chloro. In a preferred embodiment m is 0 or 1 and $R^5$ is halo, preferably chloro.

In an embodiment, there are provided compounds of formulae (VIa), (VIb), (VIc), (VId), (VIe), (VIf), (VIg), (VIh), (VIi), (VIj) (VIk), (VIm), (VIn), (VIo) or (VIp), wherein $R^1$ is substituted or unsubstituted pyridyl or substituted or unsubstituted oxo-dihydro-H-naphthyridinyl, preferably wherein $R^1$ is methylpyridyl or oxo-dihydro-H-naphthyridinyl.

In embodiments $R^3$ is selected from: $C_{1-6}$ alkyl, a substituted or unsubstituted carbocyclic moiety or a substituted or unsubstituted heterocyclic moiety, wherein the carbocyclic moiety and heterocyclic moiety either contain 5 or 6 atoms in a single aromatic ring or 8, 9 or 10 atoms in a fused bicyclic ring system, wherein one ring of the bicyclic ring system is aromatic.

$R^3$ may be selected from a substituted or unsubstituted: iso-propyl, tert-butyl, phenyl, pyridyl, pyridazinyl, pyrimidinyl, pyrazinyl pyrrolyl, furanyl, thiophenyl, pyrazolyl, imidazolyl, oxazolyl, isoxazolyl, thiazolyl, isothiazolyl, oxadiazolyl, thiadiazolyl, triazolyl, indolinyl, isoindolinyl, benzodioxanyl, benzofuranyl, isobenzofuranyl, benzothiophenyl, isobenzothiophenyl, benzodioxolanyl, indazolyl, indazolinyl, benzimidazolyl, benzimidazolinyl, benzthiazolyl, benzoisothiazol, chromanyl, isochromanyl, tetralinyl, quinolinyl, isoquinolinyl, tetrahydroquinolinyl, tetrahydroisoquinolinyl and tetrahydroquinoxalinyl.

Preferably, $R^3$ may be selected from: tert-butyl, phenyl, pyridyl, benzodioxanyl, benzofuranyl, benzodioxolanyl and thiophenyl.

When $R^3$ is substituted it may contain 1 or 2 substituents. When $R^3$ is substituted it may contain 1 to 4 substituents independently selected from: halo, —$OR^A$, —$NR^AR^B$, =O, —$OC(O)R^C$, —$C(O)R^C$, —$C(O)OR^A$, —$NR^AC(O)R^C$, —$C(O)NR^AR^B$, —$SO_2R^C$, —$SOR^C$, —CN, $C_{1-4}$ alkyl, $C_{1-4}$ haloalkyl and $C_{3-6}$ cycloalky in which the aforementioned-alkyl, haloalkyl and cycloalkyl groups may themselves also be unsubstituted or substituted with 1 to 3 groups independently selected from: —$OR^A$, —CN, —$SOR^C$, and $NR^AR^B$I.

In embodiments $R^3$ is substituted by 1 or 2 substituents selected from: chloro, fluoro, methyl, ethyl, —OMe, —CN, —$SO_2$Me, trifluoromethyl and trifluoroethyl, in particular chloro, fluoro, methyl, ethyl, —$SO_2$Me, trifluoromethyl and trifluoroethyl.

In embodiments $R^A$ and $R^B$ are each independently selected from H, methyl, ethyl or trifluoromethyl and $R^C$ is selected from methyl, ethyl or trifluoromethyl. Preferably, $R^A$ and $R^B$ are H; $R^A$ and $R^B$ are methyl; or $R^A$ is H and $R^B$ is methyl. Preferably, $R^C$ is methyl.

Any compound of the invention may be a racemic mixture of two enantiomers or a single enantiomer, either the (R)- or (S)-enantiomer. The compounds of the invention may also be a single enantiomer, either the (+)- or (−)-enantiomer, as determined by the degree of rotation of plane polarized light.

In particular, the invention provides the following compounds.

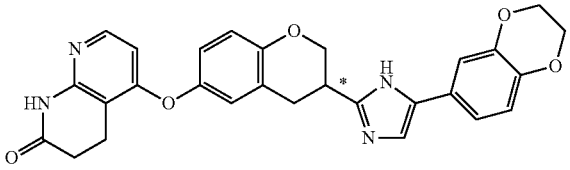

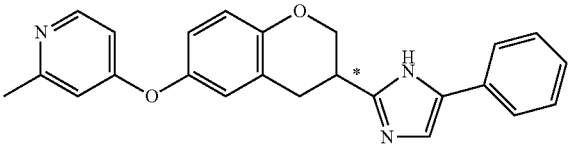

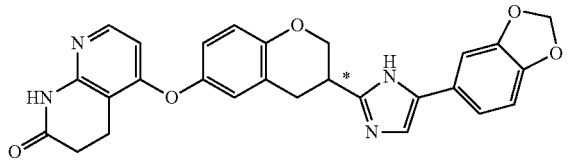

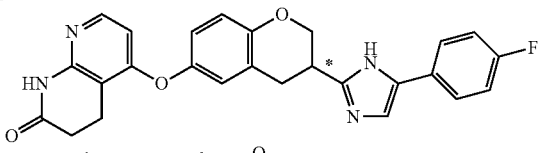

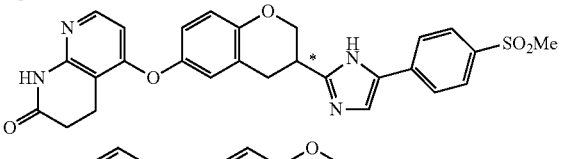

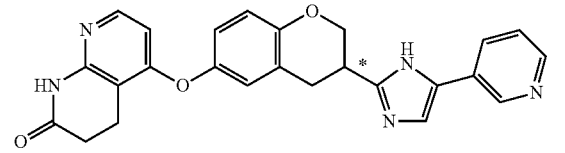

-continued

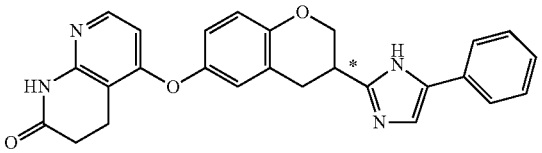

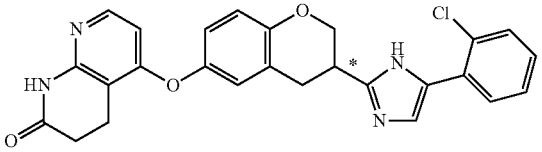

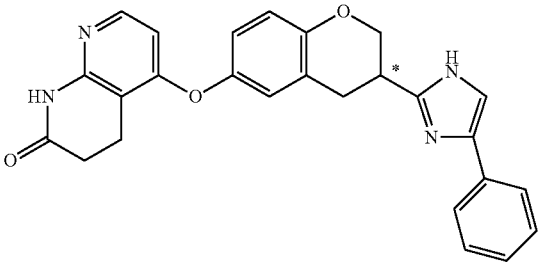

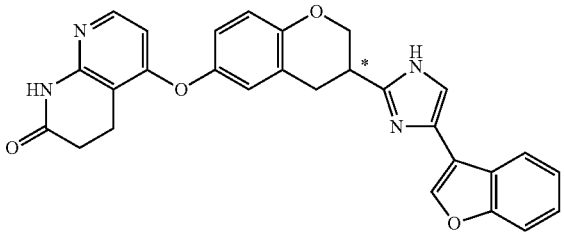

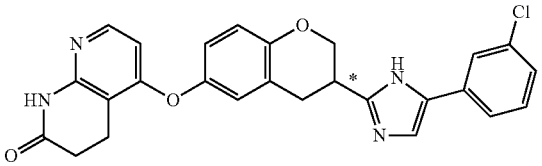

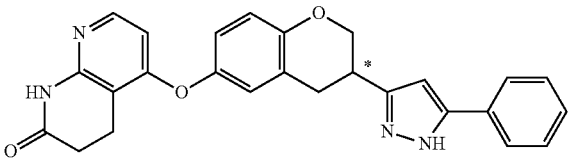

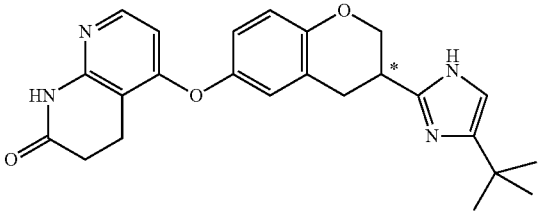

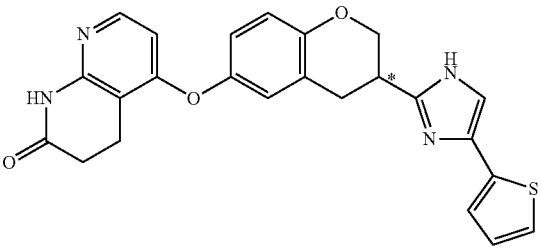

-continued

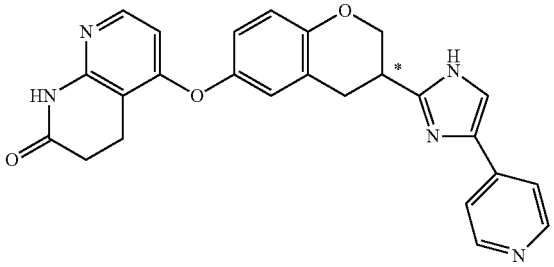

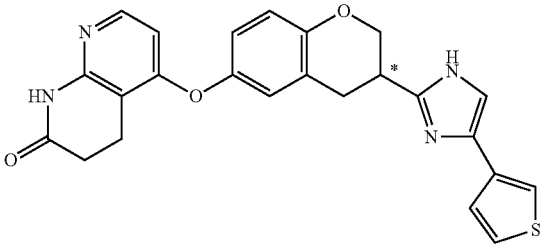

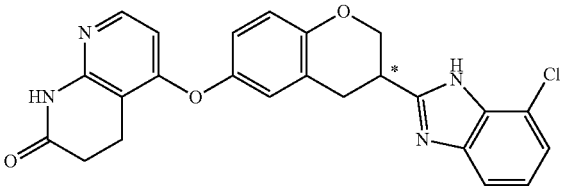

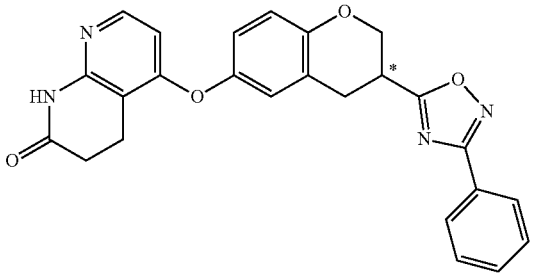

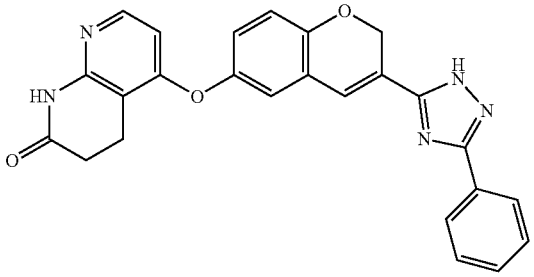

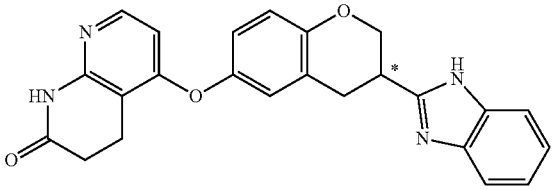

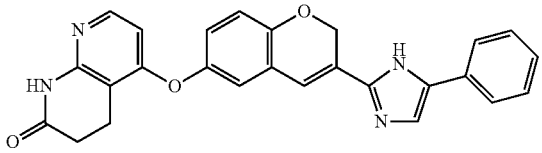

-continued

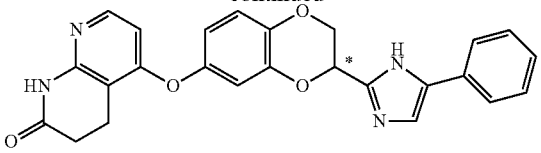

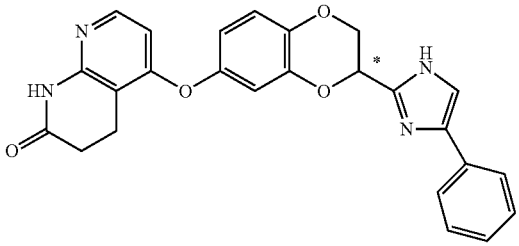

Some of the above compounds have a chiral centre. Both enantiomers of the above compounds are contemplated by the invention. The chiral centre is indicated on the compounds above with a * symbol. In one embodiment the compounds of the invention have the (R)-configuration at the stereocentre. In an alternative embodiment the compounds of the invention have the (S)-configuration at the stereocentre.

In another aspect of the invention there is provided a compound of formula (I) for use as a medicament.

In another aspect a compound of formula (I) is for use in the treatment of a condition which is modulated by RAF kinases, for example B-RAF or C-RAF. Usually conditions that are modulated by RAF kinases, optionally B-RAF or C-RAF, are conditions that would be treated by the inhibition of RAF kinases, optionally B-RAF or C-RAF, using a compound of the present invention. A compound of formula (I) may be for use in the treatment of a condition treatable by the inhibition of RAF kinases, optionally B-RAF or C-RAF.

RAF kinase inhibition is relevant for the treatment of many different diseases associated with the abnormal activity of the MAPK pathway. In embodiments the condition treatable by the inhibition of RAF kinases, for example B-RAF or C-RAF, may be selected from: cancer, sarcoma, melanoma, skin cancer, haematological tumors, lymphoma, carcinoma and leukemia. Specific cancers, sarcomas, melanomas, skin cancers, haematological tumors, lymphomas, carcinomas and leukemia treatable by the inhibition of RAF kinases, for example B-RAF or C-RAF, may be selected from: Barret's adenocarcinoma; biliary tract carcinomas; breast cancer; cervical cancer; cholangiocarcinoma; central nervous system tumors; primary CNS tumors; glioblastomas, astrocytomas; glioblastoma multiforme; ependymomas; seconday CNS tumors (metastases to the central nervous system of tumors originating outside of the central nervous system); brain tumors; brain metastases; colorectal cancer; large intestinal colon carcinoma; gastric cancer; carcinoma of the head and neck; squamous cell carcinoma of the head and neck; acute lymphoblastic leukemia; acute myelogenous leukemia (AML); myelodysplastic syndromes; chronic myelogenous leukemia; hairy cell leukaemia; Hodgkin's lymphoma; non-Hodgkin's lymphoma; megakaryoblastic leukemia; multiple myeloma; erythroleukemia; hepatocellular carcinoma; lung cancer; small cell lung cancer; non-small cell lung cancer; ovarian cancer; endometrial cancer; pancreatic cancer; pituitary adenoma; prostate cancer; renal cancer; metastatic melanoma; uveal melanoma; and papilliary thyroid cancers.

RAF kinases inhibition, for example B-RAF or C-RAF, may also be relevant to the treatment of cardio-facio cutaneous syndrome and polycystic kidney disease.

In another aspect a compound of formula (I) is for use in the treatment of a condition which is modulated by a mutant RAF kinase, for example B-RAF$^{V600E}$. Usually conditionsthat are modulated by mutant RAF kinases, optionally B-RAF$^{V600E}$, are conditions that would be treated by the inhibition of mutant RAF kinases, optionally B-RAF$^{V600E}$, using a compound of the present invention. A compound of formula (I) may be for use in the treatment of a condition treatable by the inhibition of mutant RAF kinases, optionally B-RAF$^{V600E}$. In emboidiments the condition treatable by the inhibition of mutant RAF kinases, for example B-RAF$^{V600E}$, may be selected from: BRAF$^{V600E}$ melanoma, BRAF$^{V600E}$ colorectal cancer, BRAF$^{V600E}$ papillary thyroid cancers, BRAF$^{V600E}$ low grade serous ovarian cancers, BRAF$^{V600E}$ glioma, BRAF$^{V600E}$ hepatobiliary cancers, BRAF$^{V600E}$ hairy cell leukaemia, BRAF$^{V600E}$ non-small cell cancer, and BRAF$^{V600E}$ pilocytic astrocytoma.

In an embodiment the conditions treatable by the inhibition of RAF kinases, for example B-RAF or C-RAF, may be selected from melanoma, non-small cell cancer, colorectal cancer, ovarian cancer, thyroid cancer, breast cancer and cholangiocarcinoma. In particular, the condition treatable by the inhibition of RAF kinases, for example B-RAF or C-RAF, may be colorectal cancer or melanoma.

The invention contemplates methods of treating the above mentioned conditions and contemplates compounds of the invention for use in a method of treatment of the above mentioned conditions In an aspect of the invention, a compound of the invention may be for use in the treatment of a condition selected from: cancer, sarcoma, melanoma, skin cancer, haematological tumors, lymphoma, carcinoma and leukemia. Specific cancers, sarcomas, melanomas, skin cancers, haematological tumors, lymphomas, carcinomas and leukemia that may be treated by the compound of the invention may be selected from: Barret's adenocarcinoma; biliary tract carcinomas; breast cancer; cervical cancer; cholangiocarcinoma; central nervous system tumors; primary CNS tumors; glioblastomas, astrocytomas; glioblastoma multiforme; ependymomas; seconday CNS tumors (metastases to the central nervous system of tumors originating outside of the central nervous system); brain tumors; brain metastases; colorectal cancer; large intestinal colon carcinoma; gastric cancer; carcinoma of the head and neck; squamous cell carcinoma of the head and neck; acute lymphoblastic leukemia; acute myelogenous leukemia (AML); myelodysplastic syndromes; chronic myelogenous leukemia; hairy cell leukaemia; Hodgkin's lymphoma; non-Hodgkin's lymphoma; megakaryoblastic leukemia; multiple myeloma; erythroleukemia; hepatocellular carcinoma; lung cancer; small cell lung cancer; non-small cell lung cancer; ovarian cancer; endometrial cancer; pancreatic cancer; pituitary adenoma; prostate cancer; renal cancer; metastatic melanoma; uveal melanoma; and papilliary thyroid cancers.

In an embodiment a compound of the invention may be for use in the treatment of a condition selected from: melanoma, non-small cell cancer, colorectal cancer, ovarian cancer, thyroid cancer, breast cancer and cholangiocarcinoma. In particular, the compound of the invention may be for use in the treatment of colorectal cancer or melanoma.

In an aspect of the invention there is provided a method of treatment of a condition which is modulated by RAF kinases, wherein the method comprises administering a therapeutic amount of a compound of the invention, to a patient in need thereof.

The method of treatment may be a method of treating a condition treatable by the inhibition of RAF kinases, e.g. B-RAF or C-RAF. These conditions are described above in relation to conditions treatable by the inhibition of RAF kinases.

In an aspect of the invention there is provided a method of treatment of a condition selected from: cancer, sarcoma, melanoma, skin cancer, haematological tumors, lymphoma, carcinoma and leukemia wherein the method comprises administering a therapeutic amount of a compound of the invention, to a patient in need thereof. Specific cancers, sarcomas, melanomas, skin cancers, haematological tumors, lymphomas, carcinomas and leukemia that may be treated by the method of treatment may be selected from: Barret's adenocarcinoma; biliary tract carcinomas; breast cancer; cervical cancer; cholangiocarcinoma; central nervous system tumors; primary CNS tumors; glioblastomas, astrocytomas; glioblastoma multiforme; ependymomas; seconday CNS tumors (metastases to the central nervous system of tumors originating outside of the central nervous system); brain tumors; brain metastases; colorectal cancer; large intestinal colon carcinoma; gastric cancer; carcinoma of the head and neck; squamous cell carcinoma of the head and neck; acute lymphoblastic leukemia; acute myelogenous leukemia (AML); myelodysplastic syndromes; chronic myelogenous leukemia; hairy cell leukaemia; Hodgkin's lymphoma; non-Hodgkin's lymphoma; megakaryoblastic leukemia; multiple myeloma; erythroleukemia; hepatocellular carcinoma; lung cancer; small cell lung cancer; non-small cell lung cancer; ovarian cancer; endometrial cancer; pancreatic cancer; pituitary adenoma; prostate cancer; renal cancer; metastatic melanoma; uveal melanoma; and papilliary thyroid cancers.

In an embodiment the method may be for treating a condition selected from: melanoma, non-small cell cancer, colorectal cancer, ovarian cancer, thyroid cancer, breast cancer and cholangiocarcinoma, wherein the method comprises administering a therapeutic amount of a compound of the invention to a patient in need thereof. In particular, method may be for treating colorectal cancer or melanoma.

In another aspect of the invention there is provided a pharmaceutical composition, wherein the composition comprises a compound of the invention and one or more pharmaceutically acceptable excipients.

In an embodiment the pharmaceutical composition may be a combination product comprising an additional pharmaceutically active agent. The additional pharmaceutically active agent may be an anti-tumor agent described below.

In an aspect of the invention there is provided a use of a compound of formula (I) in the manufacture of a medicament for the treatment of a condition which is modulated by RAF kinases, e.g. B-RAF or C-RAF. The condition may be any of the conditions mentioned above.

In any of the aspects or embodiments of the invention the RAF kinases may be B-RAF or C-RAF. In any of the aspects or embodiments of the invention the B-RAF kinase may be the B-RAF V600E mutant. Thus, the compounds of the invention may be utilised in the treatment of a condition which is modulated by B-RAF and/or C-RAF. Similarly, the compounds of the invention may be utilised in the treatment of conditions treatable by the inhibition of B-RAF and/or C-RAF. Furthermore, the compounds of the invention may be utilised in the treatment of a condition which is modulated by B-RAF$^{V600E}$. In addition the compounds of the invention may be utilised in the treatment of conditions treatable by the inhibition of B-RAF$^{V600E}$. B-RAF$^{V600E}$ is a mutant form of wild type B-RAF which is believed to play a role in aberrant MAPK pathway signalling, giving rise to uncontrolled cell growth.

In an aspect of the invention there is provided a use of a compound of the invention for preventing cutaneous squamous cell carcinoma during the treatment of melanomas.

BRIEF DESCRIPTION OF THE DRAWINGS

Embodiments of the invention are further described hereinafter with reference to the accompanying drawings, in which:

FIG. 1 is a graph showing reduced paradoxical activation of MAPK pathway for a compound of the invention (Example 3).

DETAILED DESCRIPTION

Given below are definitions of terms used in this application. Any term not defined herein takes the normal meaning as the skilled person would understand the term.

The term "halo" refers to one of the halogens, group 17 of the periodic table. In particular the term refers to fluorine, chlorine, bromine and iodine. Preferably, the term refers to fluorine or chlorine.

The term "$C_{1-6}$ alkyl" refers to a linear or branched hydrocarbon chain containing 1, 2, 3, 4, 5 or 6 carbon atoms, for example methyl, ethyl, n-propyl, iso-propyl, n-butyl, sec-butyl, tert-butyl, n-pentyl and n-hexyl. Alkylene groups may likewise be linear or branched and may have two places of attachment to the remainder of the molecule. Furthermore, an alkylene group may, for example, correspond to one of those alkyl groups listed in this paragraph. The alkyl and alkylene groups may be unsubstituted or substituted by one or more substituents. Possible substituents are described below. Substituents for the alkyl group may be halogen, e.g. fluorine, chlorine, bromine and iodine, OH, $C_{1-6}$ alkoxy.

The term "$C_{1-6}$ alkoxy" refers to an alkyl group which is attached to a molecule via oxygen. This includes moieties where the alkyl part may be linear or branched and may contain 1, 2, 3, 4, 5 or 6 carbon atoms, for example methyl, ethyl, n-propyl, iso-propyl, n-butyl, sec-butyl, tert-butyl, n-pentyl and n-hexyl. Therefore, the alkoxy group may be methoxy, ethoxy, n-propoxy, iso-propoxy, n-butoxy, sec-butoxy, tert-butoxy, n-pentoxy and n-hexoxy. The alkyl part of the alkoxy group may be unsubstituted or substituted by one or more substituents. Possible substituents are described below. Substituents for the alkyl group may be halogen, e.g. fluorine, chlorine, bromine and iodine, OH, $C_{1-6}$ alkoxy.

The term "$C_{1-6}$ haloalkyl" refers to a hydrocarbon chain substituted with at least one halogen atom independently chosen at each occurrence, for example fluorine, chlorine, bromine and iodine. The halogen atom may be present at any position on the hydrocarbon chain. For example, $C_{1-6}$ haloalkyl may refer to chloromethyl, flouromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl.

The term "$C_{2-6}$ alkenyl" refers to a branched or linear hydrocarbon chain containing at least one double bond and having 2, 3, 4, 5 or 6 carbon atoms. The double bond(s) may be present as the E or Z isomer. The double bond may be at any possible position of the hydrocarbon chain. For example, the "$C_{2-6}$ alkenyl" may be ethenyl, propenyl, butenyl, butadienyl, pentenyl, pentadienyl, hexenyl and hexadienyl.

The term "$C_{2-6}$ alkynyl" refers to a branched or linear hydrocarbon chain containing at least one triple bond and having 2, 3, 4, 5 or 6 carbon atoms. The triple bond may be at any possible position of the hydrocarbon chain. For example, the "$C_{2-6}$ alkynyl" may be ethynyl, propynyl, butynyl, pentynyl and hexynyl.

The term "$C_{1-6}$ heteroalkyl" refers to a branched or linear hydrocarbon chain containing 1, 2, 3, 4, 5, or 6 carbon atoms and at least one heteroatom selected from N, O and S positioned between any carbon in the chain or at an end of the chain. For example, the hydrocarbon chain may contain one or two heteroatoms. The $C_{1-6}$ heteroalkyl may be bonded to the rest of the molecule through a carbon or a heteroatom. For example, the "$C_{1-6}$ heteroalkyl" may be $C_{1-6}$ N-alkyl, $C_{1-6}$ N,N-alkyl, or $C_{1-6}$ O-alkyl.

The term "carbocyclic" refers to a saturated or unsaturated carbon containing ring system. A "carbocyclic" system may be monocyclic or a fused polycyclic ring system, for example, bicyclic or tricyclic. A "carbocyclic" moiety may contain from 3 to 14 carbon atoms, for example, 3 to 8 carbon atoms in a monocyclic system and 7 to 14 carbon atoms in a polycyclic system. "Carbocyclic" encompasses cycloalkyl moieties, cycloalkenyl moieties, aryl ring systems and fused ring systems including an aromatic portion.

The term "heterocyclic" refers to a saturated or unsaturated ring system containing at least one heteroatom selected from N, O or S. A "heterocyclic" system may contain 1, 2, 3 or 4 heteroatoms, for example 1 or 2. A "heterocyclic" system may be monocyclic or a fused polycyclic ring system, for example, bicyclic or tricyclic. A "heterocyclic" moiety may contain from 3 to 14 carbon atoms, for example, 3 to 8 carbon atoms in a monocyclic system and 7 to 14 carbon atoms in a polycyclic system. "Heterocyclic" encompasses heterocycloalkyl moieties, heterocycloalkenyl moieties and heteroaromatic moieties. For example, the heterocyclic group may be: oxirane, aziridine, azetidine, oxetane, tetrahydrofuran, pyrrolidine, imidazolidine, succinimide, pyrazolidine, oxazolidine, isoxazolidine, thiazolidine, isothiazolidine, piperidine, morpholine, thiomorpholine, piperazine, and tetrahydropyran.

The term "$C_{3-8}$ cycloalkyl" refers to a saturated hydrocarbon ring system containing 3, 4, 5, 6, 7 or 8 carbon atoms. For example, the "$C_{3-8}$ cycloalkyl" may be cyclopropyl, cyclobutyl, cyclopentyl, cyclohexyl, cycloheptyl and cyclooctyl.

The term "$C_{3-8}$ cycloalkenyl" refers to an unsaturated hydrocarbon ring system containing 3, 4, 5, 6, 7 or 8 carbon atoms that is not aromatic. The ring may contain more than one double bond provided that the ring system is not aromatic. For example, the "$C_{3-8}$ cycloalkyl" may be cyclopropenyl, cyclobutenyl, cyclopentenyl, cyclopentadienyl, cyclohexenyl, cyclohexadienly, cycloheptenyl, cycloheptadiene, cyclooctenyl and cycloatadienyl.

The term "$C_{3-8}$ heterocycloalkyl" refers to a saturated hydrocarbon ring system containing 3, 4, 5, 6, 7 or 8 carbon atoms and at least one heteroatom within the ring selected from N, O and S. For example there may be 1, 2 or 3 heteroatoms, optionally 1 or 2. The "$C_{3-8}$ heterocycloalkyl" may be bonded to the rest of the molecule through any carbon atom or heteroatom. The "$C_{3-8}$ heterocycloalkyl" may have one or more, e.g. one or two, bonds to the rest of the molecule: these bonds may be through any of the atoms in the ring. For example, the "$C_{3-8}$ heterocycloalkyl" may be oxirane, aziridine, azetidine, oxetane, tetrahydrofuran, pyrrolidine, imidazolidine, succinimide, pyrazolidine, oxazolidine,isoxazolidine, thiazolidine, isothiazolidine, piperidine, morpholine, thiomorpholine, piperazine, and tetrahydropyran.

The term "$C_{3-8}$ heterocycloalkenyl" refers to an unsaturated hydrocarbon ring system, that is not aromatic, containing 3, 4, 5, 6, 7 or 8 carbon atoms and at least one heteroatom within the ring selected from N, O and S. For example there may be 1, 2 or 3 heteroatoms, optionally 1 or 2. The "$C_{3-8}$ heterocycloalkenyl" may be bonded to the rest of the molecule through any carbon atom or heteroatom. The "$C_{3-8}$ heterocycloalkenyl" may have one or more, e.g. one or two, bonds to the rest of the molecule: these bonds may be through any of the atoms in the ring. For example, the "$C_{3-8}$ heterocycloalkyl" may be tetrahydropyridine, dihydropyran, dihydrofuran, pyrroline.

The term "aromatic" when applied to a substituent as a whole means a single ring or polycyclic ring system with 4n+2 electrons in a conjugated π system within the ring or ring system where all atoms contributing to the conjugated π system are in the same plane.

The term "aryl" refers to an aromatic hydrocarbon ring system. The ring system has 4n+2 electrons in a conjugated π system within a ring where all atoms contributing to the conjugated π system are in the same plane. For example, the "aryl" may be phenyl and naphthyl. The aryl system itself may be substituted with other groups.

The term "heteroaryl" refers to an aromatic hydrocarbon ring system with at least one heteroatom within a single ring or within a fused ring system, selected from O, N and S. The ring or ring system has 4n+2 electrons in a conjugated π system where all atoms contributing to the conjugated π system are in the same plane. For example, the "heteroaryl" may be imidazole, thiene, furane, thianthrene, pyrrol, benzimidazole, pyrazole, pyrazine, pyridine, pyrimidine and indole.

The term "alkaryl" refers to an aryl group, as defined above, bonded to a $C_{1-4}$ alkyl, where the $C_{1-4}$ alkyl group provides attachment to the remainder of the molecule.

The term "alkheteroaryl" refers to a heteroaryl group, as defined above, bonded to a $C_{1-4}$ alkyl, where the alkyl group provides attachment to the remainder of the molecule.

The term "halogen" herein includes reference to F, Cl, Br and I. Halogen may be Cl. Halogen may be F.

A bond terminating in a "∿" represents that the bond is connected to another atom that is not shown in the structure. A bond terminating inside a cyclic structure and not terminating at an atom of the ring structure represents that the bond may be connected to any of the atoms in the ring structure where allowed by valency.

Where a moiety is substituted, it may be substituted at any point on the moiety where chemically possible and consistent with atomic valency requirements. The moiety may be substituted by one or more substituents, e.g. 1, 2, 3 or 4 substituents; optionally there are 1 or 2 substituents on a group. Where there are two or more substituents, the substituents may be the same or different. The substituent(s) may be selected from: OH, $NHR^9$, amidino, guanidino, hydroxyguanidino, formamidino, isothioureido, ureido, mercapto, C(O)H, acyl, acyloxy, carboxy, sulfo, sulfamoyl, carbamoyl, cyano, azo, nitro, halo, $C_{1-6}$ alkyl, $C_{1-6}$ alkoxy, $C_{1-6}$ haloalkyl, $C_{3-8}$ cycloalkyl, $C_{2-6}$ alkenyl, $C_{2-6}$ alkynyl, aryl, heteroaryl or alkaryl. Where the group to be substituted is an alkyl group the substituent may be =O. Where the moiety is substituted with two or more substituents and two of the substituents are adjacent the adjacent substituents may form a $C_{4-8}$ ring along with the atoms of the moiety on which the substituents are substituted, wherein the $C_{4-8}$ ring is a saturated or unsaturated hydrocarbon ring with 4, 5, 6, 7, or 8 carbon atoms or a saturated or unsaturated hydrocarbon ring with 4, 5, 6, 7, or 8 carbon atoms and 1, 2 or 3 heteroatoms.

Substituents are only present at positions where they are chemically possible, the person skilled in the art being able to decide (either experimentally or theoretically) without inappropriate effort which substitutions are chemically possible and which are not.

Ortho, meta and para substitution are well understood terms in the art. For the absence of doubt, "ortho" substitution is a substitution pattern where adjacent carbons possess a substituent, whether a simple group, for example the fluoro group in the example below, or other portions of the molecule, as indicated by the bond ending in "∿"

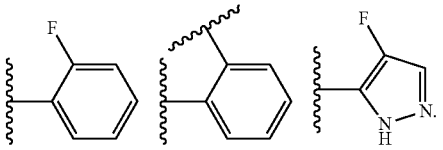

"Meta" substitution is a substitution pattern where two substituents are on carbons one carbon removed from each other, i.e with a single carbon atom between the substituted carbons. In other words there is a substituent on the second atom away from the atom with another substituent. For example the groups below are meta substituted.

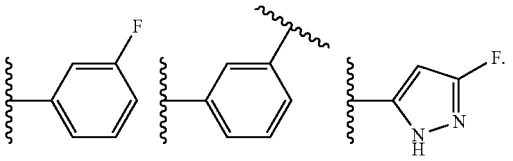

"Para" substitution is a substitution pattern where two substituents are on carbons two carbons removed from each other, i.e with two carbon atoms between the substituted carbons. In other words there is a substituent on the third atom away from the atom with another substituent. For example the groups below are para substituted.

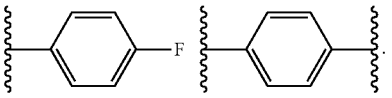

By "acyl" is meant an organic radical derived from, for example, an organic acid by the removal of the hydroxyl group, e.g. a radical having the formula R—C(O)—, where R may be selected from H, $C_{1-6}$ alkyl, $C_{3-8}$ cycloalkyl, phenyl, benzyl or phenethyl group, eg R is H or $C_{1-3}$ alkyl. In one embodiment acyl is alkyl-carbonyl. Examples of acyl groups include, but are not limited to, formyl, acetyl, propionyl and butyryl. A particular acyl group is acetyl.

Throughout the description the disclosure of a compound also encompasses pharmaceutically acceptable salts, solvates and stereoisomers thereof. Where a compound has a stereocentre, both (R) and (S) stereoisomers are contemplated by the invention, equally mixtures of stereoisomers ora racemic mixture are completed by the present application. Where a compound of the invention has two or more stereocentres any combination of (R) and (S) stereoisomers is contemplated. The combination of (R) and (S) stereoisomers may result in a diastereomeric mixture or a single diastereoisomer. The compounds of the invention may be present as a single stereoisomer or may be mixtures of stereoisomers, for example racemic mixtures and other enantiomeric mixtures, and diasteroemeric mixtures. Where the mixture is a mixture of enantiomers the enantiomeric excess may be any of those disclosed above. Where the compound is a single stereoisomer the compounds may still contain other diasteroisomers or enantiomers as impurities. Hence a single stereoisomer does not necessarily have an enantiomeric excess (e.e.) or diastereomeric excess (d.e.) of 100% but could have an e.e. or d.e. of about at least 85%

In embodiments where there is a single enantiomer of the compounds of the invention, the compounds of the invention may have an enantiomeric purity of at least about 90% enantiomeric excess (ee), at least about 95% enantiomeric excess (ee), at least about 98% enantiomeric excess (ee), at least about 99% enantiomeric excess (ee), or 100% enantiomeric excess (ee). In embodiments where there is a mixture of enantiomers of the compounds of the invention, the compounds of the invention may be a racemic mixture or any other mixture of enantiomers, for example the compounds of the invention may have an enantiomeric purity of at least about 50% enantiomeric excess (ee), at least about 60% enantiomeric excess (ee), at least about 70% enantiomeric excess (ee), at least about 80% enantiomeric excess (ee), at least about 90% enantiomeric excess (ee), or at least about 95% enantiomeric excess (ee).

The invention contemplates pharmaceutically acceptable salts of the compounds of formula (I). These may include the acid addition and base salts of the compounds. These may be acid addition and base salts of the compounds. In addition the invention contemplates solvates of the compounds. These may be hydrates or other solvated forms of the compound.

Suitable acid addition salts are formed from acids which form non-toxic salts. Examples include the acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 1,5-naphthalenedisulfonate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate and hemicalcium salts. For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) may be prepared by one or more of three methods:
(i) by reacting the compound of formula (I) with the desired acid or base;
(ii) by removing an acid- or base-labile protecting group from a suitable precursor of the compound of formula (I) or by ring-opening a suitable cyclic precursor, for example, a lactone or lactam, using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to compounds of any formula include references to salts, solvates and complexes thereof and to solvates and complexes of salts thereof.

The compounds of the invention include compounds of a number of formula as herein defined, including all polymorphs and crystal habits thereof, prodrugs and isomers thereof (including optical, geometric and tautomeric isomers) as hereinafter defined and isotopically-labeled compounds of the invention.

Before purification, the compounds of the present invention may exist as a mixture of enantiomers depending on the synthetic procedure used. The enantiomers can be separated by conventional techniques known in the art. Thus the invention covers individual enantiomers as well as mixtures thereof.

For some of the steps of the process of preparation of the compounds of formula (I), it may be necessary to protect potential reactive functions that are not wished to react, and to cleave said protecting groups in consequence. In such a case, any compatible protecting radical can be used. In particular methods of protection and deprotection such as those described by T. W. GREENE (Protective Groups in Organic Synthesis, A. Wiley-Interscience Publication, 1981) or by P. J. Kocienski (Protecting groups, Georg Thieme Verlag, 1994), can be used. All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

Also, the compounds of the present invention as well as intermediates for the preparation thereof can be purified according to various well-known methods, such as for example crystallization or chromatography.

The method of treatment or the compound for use in the treatment of cancer, sarcoma, melanoma, skin cancer, haematologicaltumors, lymphoma, carcinoma and leukemia as defined hereinbefore may be applied as a sole therapy or be a combination therapy with an additional active agent.

The method of treatment or the compound for use in the treatment of cancer, sarcoma, melanoma, skin cancer, haematological tumors, lymphoma, carcinoma and leukemia may involve, in addition to the compound of the invention, conventional surgery or radiotherapy or chemotherapy. Such chemotherapy may include one or more of the following categories of anti-tumor agents:

(i) antiproliferative/antineoplastic drugs and combinations thereof, such as alkylating agents (for example cis-platin, oxaliplatin, carboplatin, cyclophosphamide, nitrogen mustard, bendamustin, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, pemetrexed, cytosine arabinoside, and hydroxyurea); antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); proteasome inhibitors, for example carfilzomib and bortezomib; interferon therapy; and topoisomerase inhibitors (for example epipodophyllotoxins like etoposide and teniposide, amsacrine, topotecan, mitoxantrone and camptothecin);

(ii) cytostatic agents such as antiestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents, for example dasatinib and bosutinib (SKI-606), and metalloproteinase inhibitors, inhibitors of urokinase plasminogen activator receptor function or antibodies to Heparanase;

(iv) inhibitors of growth factor function: for example such inhibitors include growth factor antibodies and growth factor receptor antibodies, for example the anti-erbB2 antibody trastuzumab [Herceptin™], the anti-EGFR antibody panitumumab, the anti-erbB1 antibody cetuximab, tyrosine kinase inhibitors, for example inhibitors of the epidermal growth factor family (for example EGFR family tyrosine kinase inhibitors such as gefitinib, erlotinib and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; modulators of protein regulators of cell apoptosis (for example Bcl-2 inhibitors); inhibitors of the platelet-derived growth factor family such as imatinib and/or nilotinib (AMN107); inhibitors of serine/threonine kinases (for example Ras/RAF signalling inhibitors such as farnesyl transferase inhibitors, for example sorafenib, tipifarnib and lonafarnib), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor, kinase inhibitors; aurora kinase inhibitors and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™); thalidomide; lenalidomide; and for example, a VEGF receptor tyrosine kinase inhibitor such as vandetanib, vatalanib, sunitinib, axitinib and pazopanib;

(vi) gene therapy approaches, including for example approaches to replace aberrant genes such as aberrant p53 or aberrant BRCA1 or BRCA2;

(vii) immunotherapy approaches, including for example antibody therapy such as alemtuzumab, rituximab, ibritumomab tiuxetan (Zevalin®) and ofatumumab; interferons such as interferon α; interleukins such as IL-2 (aldesleukin); interleukin inhibitors for example IRAK4 inhibitors; cancer vaccines including prophylactic and treatment vaccines such as HPV vaccines, for example Gardasil, Cervarix, Oncophage and Sipuleucel-T (Provenge); toll-like receptor modulators for example TLR-7 or TLR-9 agonists; and PD-1 antagonists, PDL-1 antagonists, and IDO-1 antagonists; and (viii) cytotoxic agents for example fludaribine (fludara), cladribine, pentostatin (Nipent™);

(ix) steroids such as corticosteroids, including glucocorticoids and mineralocorticoids, for example aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives. A combination of steroids may be used, for example a combination of two or more steroids mentioned in this paragraph;

(x) targeted therapies, for example PI3Kd inhibitors, for example idelalisib and perifosine.

Such combination treatment may be achieved by way of the simultaneous, sequential or separate dosing of the individual components of the treatment. Such combination products employ the compounds of this invention within a therapeutically effective dosage range described hereinbefore and the other pharmaceutically-active agent within its approved dosage range.

According to a further aspect of the invention there is provided a pharmaceutical product comprising a compound of formula (I), or a pharmaceutically acceptable salt thereof as defined hereinbefore and an additional active agent. The additional active agent may be an anti-tumour agent as defined hereinbefore for the combination treatment of a condition modulated by a RAF kinase, for example B-RAF or C-RAF.

According to a further aspect of the invention there is provided a method of treatment a condition modulated by a RAF kinase, for example B-RAF or C-RAF comprising administering a therapeutically effective amount of a compound of formula (I), or a pharmaceutically acceptable salt thereof simultaneously, sequentially or separately with an additional anti-tumor agent, as defined hereinbefore, to a patient in need thereof.

According to a further aspect of the invention there is provided a compound of formula (I), or a pharmaceutically acceptable salt thereof for use simultaneously, sequentially or separately with an additional anti-tumour agent as defined hereinbefore, in the treatment of a condition modulated by a RAF kinase, for example B-RAF or C-RAF.

According to another aspect of the invention there is provided a use of the compound of formula (I) in combination with an anti-tumor agent as hereinbefore described. The compound of formula (I) may be used simultaneously, sequentially or separately with the additional anti-tumor agent The use may be in a single combination product comprising the compound of formula (I) and the anti-tumor agent.

According to a further aspect there is provided a method of providing a combination product, wherein the method comprises providing a compound of formula (I) simultaneously, sequentially or separately with an anti-tumor agent, as defined hereinbefore. The method may comprise combining the compound of formula (I) and the anti-tumor agent in a single dosage form. Alternatively the method may comprise providing the anti-tumor agent as separate dosage forms.

According to a further aspect there is provided a method of providing a combination product, wherein the method comprises providing a compound of formula (I) simultaneously, sequentially or separately with an anti-tumor agent, as defined hereinbefore. The method may comprise combining the compound of formula (I) and the anti-tumor agent in a single dosage form. Alternatively the method may comprise providing the anti-tumor agent as separate dosage forms.

The condition modulated by a RAF kinase, for example B-RAF or C-RAF, described above may be cancer, sarcoma, melanoma, skin cancer, haematological tumors, lymphoma, carcinoma and leukemia. More specifically the condition modulated by a RAF kinase, for example B-RAF or C-RAF, may be selected from: Barret's adenocarcinoma; biliary tract carcinomas; breast cancer; cervical cancer; cholangiocarcinoma; central nervous system tumors; primary CNS tumors; glioblastomas, astrocytomas; glioblastoma multiforme; ependymomas; seconday CNS tumors (metastases to the central nervous system of tumors originating outside of the central nervous system); brain tumors; brain metastases; colorectal cancer; large intestinal colon carcinoma; gastric cancer; carcinoma of the head and neck; squamous cell carcinoma of the head and neck; acute lymphoblastic leukemia; acute myelogenous leukemia (AML); myelodysplastic syndromes; chronic myelogenous leukemia; hairy cell leukaemia; Hodgkin's lymphoma; non-Hodgkin's lymphoma; megakaryoblastic leukemia; multiple myeloma; erythroleukemia; hepatocellular carcinoma; lung cancer; small cell lung cancer; non-small cell lung cancer; ovarian cancer; endometrial cancer; pancreatic cancer; pituitary adenoma; prostate cancer; renal cancer; metastatic melanoma; and papilliary thyroid cancers. In particular, the condition modulated by a RAF kinase, for example B-RAF or C-RAF, may be selected from: melanoma, non-small cell cancer, colorectal cancer, ovarian cancer, thyroid cancer, breast cancer and cholangiocarcinoma.

Compounds of the invention may exist in a single crystal form or in a mixture of crystal forms or they may be amorphous. Thus, compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

For the above-mentioned compounds of the invention the dosage administered will, of course, vary with the compound employed, the mode of administration, the treatment desired and the disorder indicated. For example, if the compound of the invention is administered orally, then the daily dosage of the compound of the invention may be in the range from 0.01 micrograms per kilogram body weight (m/kg) to 100 milligrams per kilogram body weight (mg/kg).

A compound of the invention, or pharmaceutically acceptable salt thereof, may be used on their own but will generally be administered in the form of a pharmaceutical composition in which the compounds of the invention, or pharmaceutically acceptable salt thereof, is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration of the compounds of the invention, the pharmaceutical composition which is used to administer the compounds of the invention will preferably comprise from 0.05 to 99% w (percent by weight) compounds of the invention, more preferably from 0.05 to 80% w compounds of the invention, still more preferably from 0.10 to 70% w compounds of the invention, and even more preferably from 0.10 to 50% w compounds of the invention, all percentages by weight being based on total composition.

The pharmaceutical compositions may be administered topically (e.g. to the skin) in the form, e.g., of creams, gels, lotions, solutions, suspensions, or systemically, e.g. by oral administration in the form of tablets, capsules, syrups, powders or granules; or by parenteral administration in the form of a sterile solution, suspension or emulsion for injection (including intravenous, subcutaneous, intramuscular, intravascular or infusion); by rectal administration in the form of suppositories; or by inhalation in the form of an aerosol.

For oral administration the compounds of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compounds of the invention may be admixed with, for example, a vegetable oil or polyethylene glycol. Hard gelatine capsules may contain granules of the compound using either the above-mentioned excipients for tablets. Also liquid or semi-solid formulations of the compound of the invention may be filled into hard gelatine capsules. Liquid preparations for oral application may be in the form of syrups or suspensions, for example, solutions containing the compound of the invention, the balance being sugar and a mixture of ethanol, water, glycerol and propylene glycol. Optionally such liquidpreparations may contain colouring agents, flavouring agents, sweetening agents (such as saccharine), preservative agents and/or carboxymethylcellulose as a thickening agent or other excipients known to those skilled in art.

For intravenous (parenteral) administration the compounds of the invention may be administered as a sterile aqueous or oily solution.

The size of the dose for therapeutic purposes of compounds of the invention will naturally vary according to the nature and severity of the conditions, the age and sex of the animal or patient and the route of administration, according to well-known principles of medicine.

Dosage levels, dose frequency, and treatment durations of compounds of the invention are expected to differ depending on the formulation and clinical indication, age, and comorbid medical conditions of the patient. The standard duration of treatment with compounds of the invention is expected to vary between one and seven days for most clinical indications. It may be necessary to extend the duration of treatment beyond seven days in instances of recurrent infections or infections associated with tissues or implanted materials to which there is poor blood supply including bones/joints, respiratory tract, endocardium, and dental tissues.

Examples and Synthesis

Solvents, reagents and starting materials were purchased from commercial vendors and used as received unless otherwise described. All reactions were performed at room temperature unless otherwise stated. Reactions heated in a microwave used a Biotage® Initiator Sixty. Compound identity and purity confirmations were performed by LCMS UV using a Waters Acquity SQ Detector 2 (ACQ-SQD2#LCA081). The diode array detector wavelength was 254 nM and the LCMS was in positive and negative electrospray mode (m/z: 150-800). A 2 μL aliquot was injected onto a guard column (0.2 μm×2 mm filters) and UPLC column (C18, 50×2.1 mm, <2 μm) in sequence maintained at 40° C. The samples were eluted at a flow rate of 0.6 mL/min with a mobile phase system composed of A (0.1% (v/v) Formic Acid in Water) and B (0.1% (v/v) Formic Acid in Acetonitrile) according to the gradients outlined in Table 1 below. Retention times RT are reported in minutes.

TABLE 1

| Long | | | Short | | |
|---|---|---|---|---|---|
| Time (min) | % A | % B | Time (min) | % A | % B |
| 0 | 95 | 5 | 0 | 95 | 5 |
| 1.1 | 95 | 5 | 0.3 | 95 | 5 |
| 6.1 | 5 | 95 | 2 | 5 | 95 |
| 7 | 5 | 95 | 2.6 | 95 | 5 |
| 7.5 | 95 | 5 | 3 | 95 | 5 |
| 8 | 95 | 5 | | | |

Chiral column conditions as follows:

TABLE 2

| | |
|---|---|
| Instrument | Agilent 1100 HPLC-DAD |
| Column | Chiralcel OZ-RH, 4.6 × 150 mm, 5 μM |
| Analysis wavelength (nm) | 254 nm |
| Flow Rate (mL/min) | 1.10 mL/min |
| Mobile Phase A | 20 mM Ammonium bicarbonate (pH 9.0) |
| Mobile Phase B | Acetonitrile |

TABLE 2-continued

| | |
|---|---|
| Standard diluent | 1 mL Acetonitrile |
| Sample diluent | 1 mL Methanol |

| Isocratic conditions Time (min) | % A | % B |
|---|---|---|
| 0 | 40 | 60 |
| 20 | 40 | 60 |

NMR was also used to characterise final compounds. NMR spectra were obtained on a Bruker AVIII 400 Nanobay with 5 mm BBFO probe.

Compound purification was performed by flash column chromatography on silica using a Biotage® Isolera One or by preparative LCMS. LCMS purification was performed using a Waters 3100 Mass detector in positive and negative electrospray mode (m/z: 150-800) with a Waters 2489 UV/Vis detector. Samples were eluted at a flow rate of 20 mL/min on a XBridge™ prep C18 5 μM OBD 19×100 mm column with a mobile phase system composed of A (0.1% (v/v) Formic Acid in Water) and B (0.1% (v/v) Formic Acid in Acetonitrile) according to the gradient outlined in Table 2 below.

TABLE 3

| Time (min) | % A | % B |
|---|---|---|
| 0 | 70 | 30 |
| 1.5 | 70 | 30 |
| 11.7 | 5 | 95 |
| 13.7 | 5 | 95 |
| 14 | 70 | 30 |
| 15 | 70 | 30 |

Chemical names were generated using mol2nam—Structure to Name Conversion by OpenEye Scientific Software. Starting materials were purchased from commercial sources or synthesised according to literature procedures.

Abbreviations: DCM—Dichloromethane; EtOAc—Ethyl acetate; MeOH—methanol; DMF—Dimethylacetamide; Hept—Heptane; pet. Ether—40/60 petroluem ether; $Et_2O$—Diethyl ether; tBuOH—tert butanol; hr(s)—hour or hours; sat—saturated; NaH—sodium hydride 60% in mineral oil; NaHCOs—sodium hydrogen carbonate; $Cs_2CO_3$—Cesium carbonate; Brine—saturated aqueous sodium chloride solution; $Na_2SO_4$—anhydrous sodium sulphate; $NH_4OAc$—ammonium acetate; Sat aq $NH_4Cl$—saturated aqueous ammonium chloride; AcOH—acetic acid; HCl—1N aqueous hydrochloric acid; TFA—trifluoroacetic acid; SCX-2—strong cationic resin; $NEt_3$-triethylamine; DIPEA—Diisopropylethylamine; MW—microwave irradiation; HATU—1-[Bis(dimethylamino)methylene]-1H-1,2,3-triazolo[4,5-b]pyridinium 3-oxid hexafluorophosphate; DMP—Dess-Martin Periodinane; $CDCl_3$—deuterated chloroform;

$MeOD_4$—deuterated Methanol; $d_6$-DMSO—deuterated dimthylsulfoxide; Na—sodium; $^t$Bu—tert butyl.

Preparation of intermediates useful in the synthesis of compounds of the invention.

Intermediate 1: 5-fluoro-3,4-dihydro-1H-1,8-naphthyridin-2-one (Prepared According to J. Med. Chem. 2011, 54, 1836-1846.)

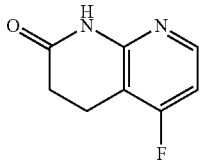

Intermediate 2: 6-hydroxychromane-3-carboxylic acid

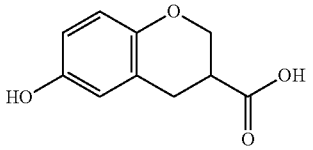

Step 1.

To a solution of 2,5-dihydroxybenzaldehyde (5.33 g, 38.59 mmol) and pyridinium p-toluenesulfonate (0.97 g, 3.86 mmol) in DCM (165 mL) was added 3,4-dihydro-2H-pyran (3.8 mL, 41.68 mmol) dropwise. The reaction was stirred for 18 hrs, diluted with DCM (150 mL), washed sat. aq. $NaHCO_3$ (250 mL)/brine (50 mL), dried ($Na_2SO_4$), filtered and concentrated in vacuo. The aqueous layer was extracted with EtOAc (400 mL), dried ($Na_2SO_4$), filtered and concentrated in vacuo. The combined organic residues were purified by flash column chromatography (0-10% EtOAc/Hept) to provide 2-hydroxy-5-tetrahydropyran-2-yloxy-benzaldehyde (8.17 g, 95% yield) as a yellow solid.

LCMS ($ES^+$, Short): RT 1.66 min, m/z 223.2 $[M+H]^+$ $^1$H NMR (400 MHz, $CDCl_3$) δ: 10.69 (1H, s), 9.84 (1H, d, J=0.5 Hz), 7.28-7.24 (2H, m), 6.94-6.90 (1H, m), 5.34 (1H, t, J=3.3 Hz), 3.95-3.87 (1H, m), 3.66-3.59 (1H, m), 2.04-1.93 (1H, m), 1.90-1.83 (2H, m), 1.76-1.60 (3H, m).

Step 2:

To a solution of 2-hydroxy-5-tetrahydropyran-2-yloxy-benzaldehyde (4.0 g, 18 mmol) in DMF (60 mL) was added $K_2CO_3$ (2.49 g, 18 mmol) and tert-butyl acrylate (3.95 mL, 27 mmol). The mixture was heated at 100° C. for 1 hr, then slowly raising the temperature from 100° C. to 135° C. (over 2 hrs) and maintained at 135° C. for 18 hrs. The reaction was cooled, concentrated in vacuo and the residue was partitioned between DCM (300 mL) and water (250 mL). The aqueous layer was extracted with DCM (250 mL), EtOAc (250 mL) and the combined organic layers were dried ($Na_2SO_4$), filtered and concentrated in vacuo. The residue was purified by flash column chromatography (0-10% EtOAc/Hept) to provide tert-butyl 6-tetrahydropyran-2-yloxy-2H-chromene-3-carboxylate (2.13 g, 36% yield) as a yellow solid.

LCMS ($ES^+$, Short) RT 2.21 min. m/z 277.2 $[M+H-^tBu]^+$ $^1$H NMR (400 MHz, $CDCl_3$) δ: 7.31 (1H, br s), 6.94 (1H, dd, J=2.8, 8.6 Hz), 6.89 (1H, d, J=2.8 Hz), 6.79 (1H, d, J=8.7 Hz), 5.31 (1H, t, J=3.2 Hz), 4.93-4.89 (2H, m), 3.98-3.89 (1H, m), 3.66-3.58 (1H, m), 2.05-1.95 (1H, m), 1.90-1.83 (2H, m), 1.73-1.60 (3H, m), 1.55 (9H, s).

Step 3

A solution of tert-butyl 6-tetrahydropyran-2-yloxy-2H-chromene-3-carboxylate (2.15 g, 6.47 mmol) in MeOH (180 mL) was hydrogenated on the H Cube (10% Pd/C cartridge) for 26 hrs. The solution was concentrated in vacuo to provide crude tert-butyl 6-tetrahydropyran-2-yloxychromane-3-carboxylate (2.01 g, 93% yield) as a pale yellow oil.

LCMS ($ES^+$, Short) RT 2.10 min, m/z 357.3 $[M+Na]^+$

Step 4:

To a solution of tert-butyl 6-tetrahydropyran-2-yloxy-chromane-3-carboxylate (2.01 g, 6.01 mmol) in MeOH (30 mL) was added pyridinium p-toluenesulfonate (194 mg, 0.77 mmol) and the mixture was stirred for 18 hrs. The reaction was concentrated in vacuo, partitioned between EtOAc (150 mL) and water (50 mL), washed with brine (50 mL), dried ($Na_2SO_4$), filtered and concentrated in vacuo. The residue was purified by flash column chromatography (0-30% EtOAc/Hept) to provide tert-butyl 6-hydroxychromane-3-carboxylate (1.48 g, 98% yield) as an off white solid.

LCMS ($ES^+$, Short) RT 1.63 min, m/z 273.2 $[M+Na]^+$ $^1$H NMR (400 MHz, $CDCl_3$) δ: 6.71 (1H, d, J=8.5 Hz), 6.63-6.57 (2H, m), 4.52 (1H, s), 4.40-4.34 (1H, m), 4.07-4.00 (1H, m), 3.06-2.87 (3H, m), 1.48 (9H, s).

Step 5:

To a solution of tert-butyl 6-hydroxychromane-3-carboxylate (1.48 g, 5.91 mmol) in DCM (20 mL) was added TFA (10 mL, 130.68 mmol) and the mixture stirred for 18 hrs. Further TFA (10 mL, 130.68 mmol) was added and the reaction stirred for 72 hrs. The reaction was concentrated in vacuo to provide 6-hydroxychromane-3-carboxylic acid (1.267 g, 110% yield) as an off white solid.

LCMS ($ES^-$, Short) RT 1.03 min, m/z 193.1 $[M-H]^-$ $^1$H NMR (400 MHz, $CD_3OD$) δ: 6.61-6.56 (1H, m), 6.53-6.49 (2H, m), 4.33-4.25 (1H, m), 4.10-4.03 (1H, m), 2.99-2.88 (3H, m).

Intermediate 3: 6-[(7-oxo-6,8-dihydro-5H-1,8-naphthyridin-4-yl)oxy]chromane-3-carboxylic acid

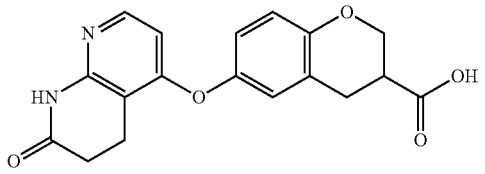

A mixture of 5-fluoro-3,4-dihydro-1H-1,8-naphthyridin-2-one (500. mg, 3.01 mmol), 6-hydroxychromane-3-carboxylic acid (642.8 mg, 3.31 mmol) and $Cs_2CO_3$ (2.94 g, 9.03 mmol) in DMF (15 mL) was split into 2 MW vials and irradiated at 150° C. for 1 hr. The combined reactions were diluted with water (100 mL), stirred for 10 mins, pH adjusted to −3 and the precipitate was filtered and dried. The precipitate was purified by SCX-2 and flash column chromatography (1-10% MeOH/DCM) to provide intermediate 3 [6-[(7-oxo-6,8-dihydro-5H-1,8-naphthyridin-4-yl)oxy]chromane-3-carboxylic acid] (335 mg, 33% yield) as a light brown solid.

LCMS ($ES^+$, Short) RT 1.25 min, m/z 341.3 $[M+H]^+$

Intermediate 4:

6-hydroxy-2H-chromene-3-carboxylic acid

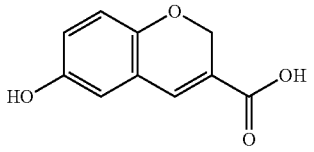

Step 1

Tert-butyl 6-hydroxy-2H-chromene-3-carboxylate was prepared using the material tert-butyl 6-tetrahydropyran-2-yloxy-2H-chromene-3-carboxylate (Intermediate 2, step 2) following the synthetic procedure for tert-butyl 6-hydroxy-chromane-3-carboxylate (Intermediate 2, step 4).

LCMS ($ES^-$, Short) RT 1.73 min, m/z 247.2 $[M-H]^-$ $^1H$ NMR (400 MHz, DMSO) δ: 9.17 (1H, s), 7.34-7.31 (1H, m), 6.73-6.71 (1H, m), 6.70-6.67 (2H, m), 4.67 (2H, d, J=1.4 Hz), 1.49 (9H, s).

Step 2

6-Hydroxy-2H-chromene-3-carboxylic acid was prepared using the material tert-butyl 6-hydroxy-2H-chromene-3-carboxylate following the synthetic procedure for 6-hydroxy-chromane-3-carboxylic acid (Intermediate 2, step 5).

LCMS ($ES^-$, Short) RT 1.13 min. m/z 191.2 $[M-H]^-$

Intermediate 5: 6-[(7-oxo-6,8-dihydro-5H-1,8-naphthyridin-4-yl)oxy]-2H-chromene-3-carboxylic acid

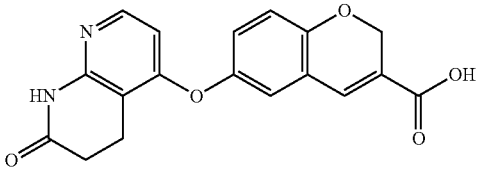

6-[(7-oxo-6,8-dihydro-5H-1,8-naphthyridin-4-yl)oxy]-2H-chromene-3-carboxylic acid (Intermediate 5) was prepared using the material 5-fluoro-3,4-dihydro-1H-1,8-naphthyridin-2-one (Intermediate 1) and 6-hydroxy-2H-chromene-3-carboxylic acid (Intermediate 4) following the synthetic procedure for 6-[(7-oxo-6,8-dihydro-5H-1,8-naphthyridin-4-yl)oxy]chromane-3-carboxylic acid (Intermediate 3)

LCMS ($ES^+$, Short) RT 1.31 min, m/z 339.1 $[M+H]^+$ $^1H$ NMR (400 MHz, $d_6$-DMSO) δ: 12.90 (1H, br s), 10.49 (1H, s), 7.97 (1H, d, J=5.8 Hz), 7.47-7.43 (1H, m), 7.21 (1H, d, J=2.9 Hz), 7.09-7.05 (1H, m), 6.94 (1H, d, J=8.8 Hz), 6.29 (1H, d, J=5.8 Hz), 4.94 (2H, d, J=1.4 Hz), 2.96-2.90 (2H, m), 2.57-2.51 (2H, m).

EXAMPLES

Example 1: 5-[3-(1H-benzimidazol-2-yl)chroman-6-yl]oxy-3,4-dihydro-1H-1,8-naphthyridin-2-one

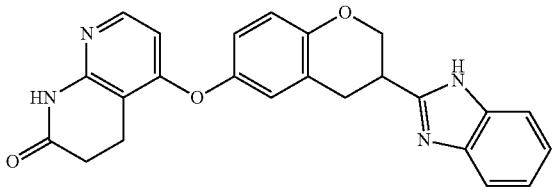

To a mixture of o-phenylenediamine (20.27 mg, 0.19 mmol), 6-[(7-oxo-6,8-dihydro-5H-1,8-naphthyridin-4-yl)oxy]chromane-3-carboxylic acid (58 mg, 0.17 mmol) and DIPEA (0.12 mL, 0.66 mmol) in DMF (2 mL) was added HATU (73.21 mg, 0.19 mmol). The mixture was stirred for 20 hrs, diluted with EtOAc (40 mL), washed brine (2×30 mL), dried ($Na_2SO_4$), filtered and concentrated in vacuo.

The residue was dissolved in AcOH (2 mL), heated at 80° C. for 4 hrs and concentrated in vacuo. The residue was diluted with sat. aq. $Na_2CO_3$ (30 mL), extracted with EtOAc (75, 50 mL) and the combined organic layers were dried ($Na_2SO_4$), filtered and concentrated in vacuo. The residue was purified by flash column chromatography (0-6% MeOH/DCM) to provide 5-[3-(1H-benzimidazol-2-yl)chroman-6-yl]oxy-3,4-dihydro-1H-1,8-naphthyridin-2-one (40 mg, 57% yield) as an off white solid.

LCMS: ($ES^+$, Long): RT 2.11 min, m/z 413.3 $[M+H]^+$ $^1H$ NMR shows a mixture of confirmers:

$^1H$ NMR (400 MHz, $d_6$ DMSO) δ: 12.61 (1H, br s), 10.47 (1H, s), 7.97 (1H, d, J=5.9 Hz), 7.57-7.50 (2H, m), 7.26-7.14 (2H, m), 7.03 (1H, d, J=2.6 Hz), 6.94 (0.2H, d, J=2.7 Hz), 6.92 (0.8H, d, J=2.7 Hz), 6.90 (0.8H, s), 6.88 (0.2H, s), 6.28 (1H, d, J=5.8 Hz), 4.64-4.56 (1H, m), 4.33-4.26 (1H, m), 3.64-3.55 (1H, m), 3.27-3.18 (2H, m), 2.97-2.90 (2H, m), 2.57-2.52 (2H, m).

Example 2: 5-[3-(7-chloro-1H-benzimidazol-2-yl)chroman-6-yl]oxy-3,4-dihydro-1H-1,8-naphthyridin-2-one

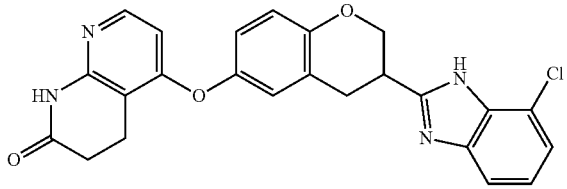

To a solution of 6-[(7-oxo-6,8-dihydro-5H-1,8-naphthyridin-4-yl)oxy]chromane-3-carboxylic acid (50 mg, 0.15 mmol) and 3-chlorobenzene-1,2-diamine (22 mg, 0.15 mmol) in DMF (2 mL) was added DIPEA (0.1 mL, 0.5700 mmol) and HATU (62.56 mg, 0.16 mmol). The mixture was stirred for 24 hrs, diluted with water (15 mL) and extracted with EtOAc (60, 30 mL). The combined organic layers were washed with brine (30 mL), dried ($Na_2SO_4$), filtered and concentrated in vacuo.

The residue was dissolved in AcOH (3 mL), heated at 80° C. for 20 hrs, cooled and concentrated in vacuo. The residuewas diluted with sat. aq. $Na_2CO_3$ (30 mL), extracted with EtOAc (75, 50 mL) and the combined organic layers were washed with brine (30 mL), dried ($Na_2SO_4$), filtered and concentrated in vacuo. The residue was purified by flash column chromatography (0-5% and 2-5% MeOH/DCM) and prep HPLC to provide 5-[3-(7-chloro-1H-benzimidazol-2-yl)chroman-6-yl]oxy-3,4-dihydro-1H-1,8-naphthyridin-2-one (22.9 mg, 35% yield) as an off white solid.

LCMS ($ES^+$, Long): RT 3.26 min, m/z 447.0, 449.0 $[M+H]^+$ $^1H$ NMR shows a mixture of confirmers:

$^1H$ NMR (400 MHz, $d_6$-DMSO) δ: 12.82 (1H, br s), 10.47 (1H, s), 7.97 (1H, d, J=5.8 Hz), 7.54-7.44 (2H, m), 7.24 (1H, d, J=7.4 Hz), 7.17 (1H, t, J=7.8 Hz), 7.05 (1H, d, J=2.4 Hz), 6.95 (0.2H, d, J=2.6 Hz), 6.93 (0.8H, d, J=2.6 Hz), 6.92 (0.8H, s), 6.89 (0.2H, s), 6.28 (1H, d, J=5.8 Hz), 4.65-4.57 (1H, m), 4.29 (0.5H, d, J=9.7 Hz), 4.27 (0.5H, 9.6 Hz), 3.68-3.57 (1H, m), 3.27-3.12 (1H, m), 2.94 (2H, t, J=7.7 Hz), 2.57-2.53 (2H, m).

Example 3: 5-[3-(4-phenyl-1H-imidazol-2-yl)chroman-6-yl]oxy-3,4-dihydro-1H-1,8-naphthyridin-2-one]

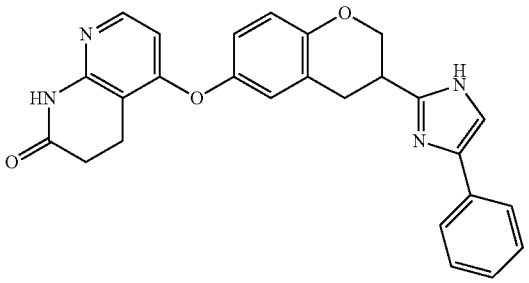

To a solution of 6-[(7-oxo-6,8-dihydro-5H-1,8-naphthyridin-4-yl)oxy]chromane-3-carboxylic acid (80 mg, 0.24 mmol) in DMF (2 mL) was added $K_2CO_3$ (97.48 mg, 0.71 mmol) and 2-bromoacetophenone (93.59 mg, 0.47 mmol). The reaction was stirred for 30 mins, diluted with water (30 mL) and extracted with EtOAc (2×50 mL). The combined organic layers were washed with brine (20 mL), dried ($Na_2SO_4$), filtered and concentrated in vacuo. The residue was purified by flash column chromatography (0-5% MeOH/DCM) to provide a yellow solid (66 mg).

The residue as dissolved in AcOH (1 mL) and added to a solution of $NH_4OAc$ (181.22 mg, 2.35 mmol) in AcOH (1 mL). The mixture was heated at 120° C. in a sealed vial for 72 hrs, cooled and concentrated in vacuo. The residue was diluted with sat. aq. $NaHCO_3$ (30 mL) and extracted with EtOAc (2×50 mL). The combined organic layers were washed with brine (30 mL), dried ($Na_2SO_4$), filtered and concentrated in vacuo. The residue was purified by flash column chromatography (0-5% and 2-5% MeOH/DCM) to provide 5-[3-(4-phenyl-1H-imidazol-2-yl)chroman-6-yl]oxy-3,4-dihydro-1H-1,8-naphthyridin-2-one (20.2 mg, 20% yield) as an orange solid.

LCMS: ($ES^+$, Long): RT 2.65 min, m/z 439.2 $[M+H]^+$ $^1H$ NMR shows a mixture of confirmers:

$^1H$ NMR (400 MHz, $d_6$-DMSO) δ: 12.31 (0.2H, s), 12.09 (0.8H, s), 10.46 (1H, s), 7.96 (1H, d, J=5.8 Hz), 7.77-7.73 (1.6H, m), 7.66-7.62 (0.4H, m), 7.60 (0.8H, d, J=2.0 Hz), 7.43-7.38 (0.5H, m), 7.36-7.30 (1.5H, m), 7.28 (0.2H, d, J=1.6 Hz), 7.26-7.21 (0.3H, m), 7.19-7.13 (0.7H, m), 7.03-6.99 (1H, m), 6.93 (0.2H, d, J=2.7 Hz), 6.91 (0.8H, d, J=2.6 Hz), 6.90 (0.8H, s), 6.88 (0.2H, s), 6.27 (1H, d, J=5.8 Hz), 4.55-4.48 (1H, m), 4.17-4.09 (1H, m), 3.45-3.35 (1H, m), 3.30-3.20 (1H, m), 3.17-3.07 (1H, m), 2.97-2.90 (2H, m), 2.57-2.52 (2H, m).

Chiral purification of Example 3 provided two enantiomrs 3A and 3B:

Analytical Separation Method:
Instrument: Thar analytical SFC
Column: ChiraCel OJ-H, 250×4.6 mm
Mobile phase: A for $CO_2$ and B for MeOH (0.05% DEA)
Gradient: B 50%
Flow rate: 2.0 mL/min
Back pressure: 100 bar
Column temperature: 35° C.
Wavelength: 220 nm Preparative Separation Method
Instrument: MG II preparative SFC
Column: ChiraCel OJ-H, 250×30 mml·D.
Mobile phase: A for $CO_2$ and B for MEOH
Gradient: B 50%
Flow rate: 50 mL/min
Back pressure: 100 bar
Column temperature: 38° C.
Wavelength: 220 nm
Cycletime: ~7.0 min Example 3A Light tan solid (45.7 mg)

LCMS:($ES^+$, final purity): RT 2.67 min, m/z 439.2 $[M+H]^+$

Chiral ee of enantiomer—99.5% [RT—7.26 mins]

Example 3B

Off white solid (48.1 mg)

LCMS: ($ES^+$, final purity): RT 2.69 min, m/z 439.2 $[M+H]^+$ Chiral ee of enantiomer—99.7% [RT—8.46 mins]

Example 4: 5-[3-[4-(4-pyridyl)-1H-imidazol-2-yl]chroman-6-yl]oxy-3,4-dihydro-1H-1,8-naphthyridin-2-one

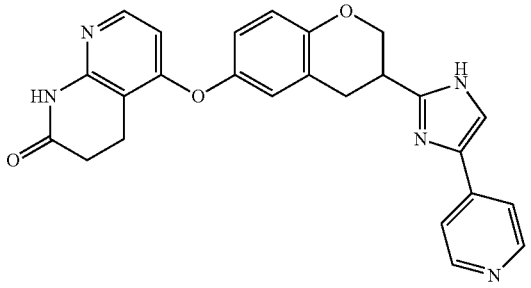

To a mixture of 6-[(7-oxo-6,8-dihydro-5H-1,8-naphthyridin-4-yl)oxy]chromane-3-carboxylic acid (80. mg, 0.24 mmol) and $K_2CO_3$ (0.04 mL, 0.47 mmol) in DMF (1 mL) was added a mixture of 4-(bromoacetyl)pyridine hydrobromide (0.07 mL, 0.47 mmol) and $NEt_3$ (0.07 mL, 0.47 mmol) in DMF (1 mL). The mixture was stirred for 30 mins, diluted with water (30 mL) and extracted with EtOAc (2×50 mL). The combined organic layers were washed with brine (30 mL), dried ($Na_2SO_4$), filtered and concentrated in vacuo.

The combined aqueous layers were extracted with EtOAc (100 mL) and the organic layer was dried ($Na_2SO_4$), filtered and concentrated in vacuo.

The combined residues were dissolved in AcOH (2.5 mL), $NH_4OAc$ (2.23 g, 28.93 mmol) was added and the reaction heated in a sealed vial at 130° C. for 68 hrs. The reaction was cooled, concentrated in vacuo, added to sat. aq. $NaHCO_3$ (70 mL) and extracted with EtOAc (2×70 mL). The combined organic layers were dried ($Na_2SO_4$), filtered and concentrated in vacuo. The residue was purified by flash column chromatography (0-10% and 5-10% MeOH/DCM) to provide 5-[3-[4-(4-pyridyl)-1H-imidazol-2-yl]chroman-6-yl]oxy-3,4-dihydro-1H-1,8-naphthyridin-2-one (25 mg, 22% yield) as a yellow powder.

LCMS ($ES^+$, Long): RT 2.40 min, m/z 440.1 $[M+H]^+$.

$^1H$ NMR shows a mixture of confirmers:

$^1H$ NMR (400 MHz, $d_6$-DMSO δ 12.37 (1H, s), 10.47 (1H, s), 8.51-8.46 (2H, m), 7.96 (1H, d, J=5.8 Hz), 7.90 (1H, s), 7.71-7.67 (2H, m), 7.02 (1H, d, J=2.7 Hz), 6.94 (0.2H, d, J=2.7 Hz), 2.92 (0.8H, d, J=2.7 Hz), 6.90 (0.8H, s), 6.88 (02H, s), 6.27 (1H, d, J=5.8 Hz), 4.54-4.49 (1H, m), 4.15 (1H, t, J=10.2 Hz), 3.47-3.37 (1H, m), 3.27-3.20 (1H, m), 3.18-3.09 (1H, m), 2.94 (2H, t, J=7.7 Hz), 2.57-2.52 (2H, m).

Example 5: 5-[3-(4-tert-butyl-1H-imidazol-2-yl) chroman-6-yl]oxy-3,4-dihydro-1H-1,8-naphthyridin-2-one

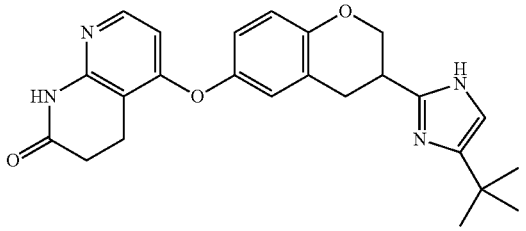

To a solution of 6-[(7-oxo-6,8-dihydro-5H-1,8-naphthyridin-4-yl)oxy]chromane-3-carboxylic acid (80 mg, 0.24 mmol) in DMF (2 mL) was added $K_2CO_3$ (64.97 mg, 0.47 mmol) and 1-bromo-3,3-dimethylbutan-2-one (0.06 mL, 0.47 mmol). The reaction was stirred for 30 mins, diluted with water (30 mL), extracted with EtOAc (2×50 mL) and the combined organic layers were washed with brine (30 mL), dried ($Na_2SO_4$), filtered and concentrated in vacuo to provide a brown solid (101 mg). The residue was dissolved in AcOH (3 mL), $NH_4OAc$ (2.23 g, 28.93 mmol) was added and the reaction heated in a sealed tube at 130° C. for 120 hrs. The mixture was cooled, concentrated in vacuo. The residue was slowly added dropwise to sat. aq. $NaHCO_3$ (50 mL) and extracted with EtOAc (2×100 mL). The combined organic layers were washed with brine (30 mL), dried ($Na_2SO_4$), filtered and concentrated in vacuo. The residue was purified by flash column chromatography (0-5% MeOH/DCM) and SCX-2. The residue was dissolved in EtOAc (50 mL), washed with sat. aq. $NaHCO_3$ (50 mL), dried ($Na_2SO_4$), filtered and concentrated in vacuo. The residue was purified by flash column chromatography (0-5% MeOH/DCM) provided 5-[3-(4-tert-butyl-1H-imidazol-2-yl)chroman-6-yl]oxy-3,4-dihydro-1H-1,8-naphthyridin-2-one (10 mg, 10% yield) as an off white solid.

LCMS ($ES^+$, Long): RT 2.57 min, m/z 419.2 $[M+H]^+$ $^1H$ NMR shows a mixture of confirmers:

$^1H$ NMR (400 MHz, $d_6$-DMSO) δ: 11.62 (0.5H, s), 11.55 (0.5H, s), 10.46 (1H, s), 7.96 (1H, dd, J=1.7, 5.8 Hz), 7.00-6.97 (1H, m), 6.92 (0.2H, d, J=2.8 Hz), 6.90 (0.8H, d, J=2.6 Hz), 6.89 (0.8H, s), 6.86 (0.2H, s), 6.73 (0.5H, d, J=1.9 Hz), 6.46 (0.5H, d, J=1.8 Hz), 6.26 (1H, dd, J=0.9, 5.8 Hz), 4.48-4.40 (1H, m), 4.07-3.97 (1H, td, J=3.8, 4.0 Hz), 3.32-3.24 (1H, m), 3.20-3.10 (1H, m), 3.08-2.99 (1H, m), 2.93 (2H, t, J=7.7 Hz), 2.57-2.53 (2H, m), 1.27 (5H, s), 1.19 (4H, s).

Example 6: 5-[3-[4-(3-thienyl)-1H-imidazol-2-yl] chroman-6-yl]oxy-3,4-dihydro-1H-1,8-naphthyridin-2-one

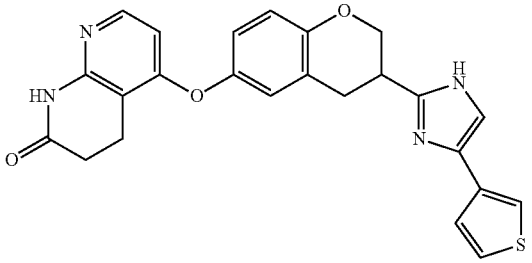

To a solution of 6-[(7-oxo-6,8-dihydro-5H-1,8-naphthyridin-4-yl)oxy]chromane-3-carboxylic acid (80 mg, 0.24 mmol) in DMF (2 mL) was added $K_2CO_3$ (64.97 mg, 0.47 mmol) and 3-(bromoacetyl)thiophene (0.07 mL, 0.47 mmol). The reaction was stirred for 30 mins, diluted with water (30 mL) and extracted with EtOAc (2×50 mL). The combined organic layers were washed with brine (30 mL), dried ($Na_2SO_4$), filtered and concentrated in vacuo to provide a brown solid (106 mg).

The solid was dissolved in AcOH (3 mL), $NH_4OAc$ (2.23 g, 28.93 mmol) was added and the reaction heated in a sealed tube at 130° C. for 72 hrs. The mixture was cooled, concentrated in vacuo, the residue dissolved in EtOAc (50 mL) and washed with sat. aq. $NaHCO_3$ (2×50 mL) and water (50 mL). The combined aqueous phases were extracted with EtOAc (50 mL) and the combined organic layers were dried ($Na_2SO_4$), filtered and concentrated in vacuo. The residue was purified by flash column chromatography (0-5% MeOH/DCM) and prep HPLC to provide 5-[-3-[4-(3-thienyl)-1H-imidazol-2-yl]chroman-6-yl]oxy-3,4-dihydro-1H-1,8-naphthyridin-2-one (9.3 mg, 9% yield) as an off white solid.

LCMS ($ES^+$, Long) RT 2.59 min, m/z 445.1 $[M+H]^+$ $^1H$ NMR shows a mixture of confirmers:

$^1H$ NMR (400 MHz, $d_6$ DMSO) δ: 12.33 (0.3H, br s), 12.05 (0.7H, br s), 10.47 (1H, s), 7.96 (1H, d, J=5.8 Hz), 7.60-7.38 (4H, m), 7.01 (1H, d, J=2.4 Hz), 6.93 (0.2H, d, J=2.5 Hz), 6.91 (0.8H, d, J=2.6 Hz), 6.90 (0.8H, s), 6.89 (0.2H, s), 6.27 (1H, d, J=5.8 Hz), 4.53-4.63 (1H, m), 4.11 (1H, t, J=10.3 Hz), 3.43-3.35 (1H, m), 3.28-3.18 (1H, m), 3.14-3.06 (1H, m), 2.94 (2H, t, J=7.7 Hz), 2.57-2.53 (2H, m).

Example 7: 5-[3-[4-(2-thienyl)-1H-imidazol-2-yl]chroman-6-yl]oxy-3,4-dihydro-1H-1,8-naphthyridin-2-one

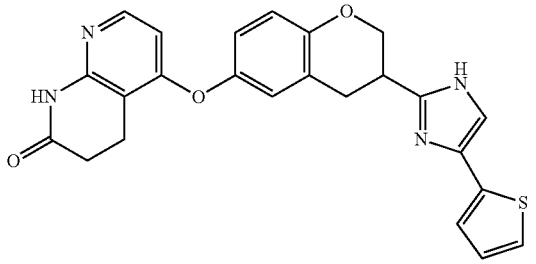

To a solution of 6-[(7-oxo-6,8-dihydro-5H-1,8-naphthyridin-4-yl)oxy]chromane-3-carboxylic acid (80 mg, 0.24 mmol) in DMF (2 mL) was added $K_2CO_3$ (64.97 mg, 0.47 mmol) and 2-bromo-1-(2-thienyl)ethanone (0.07 mL, 0.47 mmol). The reaction was stirred for 30 mins, diluted with water (30 mL) and extracted with EtOAc (2×50 mL). The combined organic layers were washed with brine (30 mL), dried ($Na_2SO_4$), filtered and concentrated in vacuo to provide a brown solid (159 mg). The solid was dissolved in AcOH (3 mL), $NH_4OAc$ (2.23 g, 28.93 mmol) was added and the reaction heated in a sealed tube at 130° C. for 72 hours. The mixture was cooled, concentrated in vacuo and the residue dissolved in EtOAc (50 mL). The organic layer was washed with sat. aq. $NaHCO_3$ (2×50 mL) and water (50 mL). The combined aqueous phases were extracted with EtOAc (50 mL) and the combined organic layers were dried ($Na_2SO_4$), filtered and concentrated in vacuo. The residue was purified by flash column chromatography (0-5% MeOH/DCM) and prep HPLC to provide 5-[3-[4-(2-thienyl)-1H-imidazol-2-yl]chroman-6-yl]oxy-3,4-dihydro-1H-1,8-naphthyridin-2-one (22.6 mg, 22% yield) as an off white solid.

LCMS (ES$^+$, Long): RT 2.65 min, m/z 445.1 $[M+H]^+$ $^1$H NMR shows a mixture of confirmers:

$^1$H NMR (400 MHz, $d_6$-DMSO) δ: 12.16 (1H, s), 10.46 (1H, s), 7.96 (1H, d, J=5.8 Hz), 7.46 (1H, s), 7.31 (1H, d, J=4.4 Hz), 7.22 (1H, d, J=3.0 Hz), 7.02 (2H, m), 6.93 (0.2H, d, J=2.7 Hz), 6.91 (0.8H, d, J=2.7 Hz), 6.90 (0.8H, s), 6.87 (0.2H, s), 6.27 (1H, d, J=5.8 Hz), 4.52-4.44 (1H, m), 4.11 (1H, t, J=10.3 Hz), 3.43-3.35 (1H, m), 3.26-3.17 (1H, m), 3.14-3.06 (1H, m), 2.93 (2H, t, J=7.7 Hz), 2.57-2.53 (2H, m).

Example 8: 5-[3-[5-(2-chlorophenyl)-1H-imidazol-2-yl]chroman-6-yl]oxy-3,4-dihydro-1H-1,8-naphthyridin-2 -one

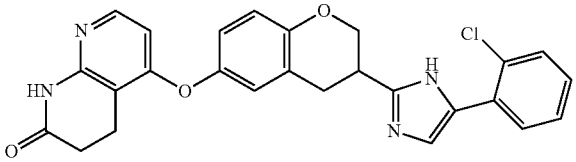

To a solution of 6-[(7-oxo-6,8-dihydro-5H-1,8-naphthyridin-4-yl)oxy]chromane-3-carboxylic acid (70 mg, 0.21 mmol) in DMF (2 mL) was added $K_2CO_3$ (56.86 mg, 0.41 mmol) and 2-bromo-1-(2-chlorophenyl)ethanone (59.9 uL, 0.41 mmol). The reaction was stirred for 2 hrs, diluted with water (20 mL) and extracted with EtOAc (50 mL). The organic layer was washed with water (30 mL), brine (20 mL), dried ($Na_2SO_4$), filtered and concentrated in vacuo. The residue was purified by flash column chromatography (0-5% MeOH/DCM) to provide a solid.

The solid was dissolved in AcOH (3 mL) and $NH_4OAc$ (1.58 g, 20.57 mmol) was added. The mixture was heated in a seal vial at 140° C. for 24 hrs, cooled and added to sat. aq. $NaHCO_3$ (250 mL)/EtOAc (50 mL). The mixture was stirred for 1 hr, diluted with EtOAc (100 mL) and the combined organic layers were washed with brine (100 mL). The combined aqueous layers were extracted with EtOAc (100 mL) and the combined organic layers were dried ($Na_2SO_4$), filtered and concentrated in vacuo. The residue was purified by flash column chromatography (0-5% MeOH/DCM) and prep HPLC to provide 5-[3-[5-(2-chlorophenyl)-1H-imidazol-2-yl]chroman-6-yl]oxy-3,4-dihydro-1H-1,8-naphthyridin-2-one (14.1 mg, 14% yield) as an off white solid.

LCMS: (ES$^+$, Long): RT 2.88 min, m/z 473.1, 475.1 $[M+H]^+$ $^1$H NMR shows a mixture of confirmers:

$^1$H NMR (400 MHz, $d_6$-DMSO) δ: 12.34 (0.2H, s), 12.28 (0.8H, s), 10.46 (1H, s), 8.13-8.08 (1H, m), 7.95 (1H, d, J=6.0 Hz), 7.74 (1H, s), 7.47-7.42 (1H, m), 7.38-7.32 (1H, m), 7.24-7.18 (1H, m), 7.02-6.99 (1H, m), 6.93 (0.2H, d, J=2.7 Hz), 6.91 (0.8H, d, J=2.6 Hz), 6.90 (0.8H, s), 6.87 (0.2H, s), 6.27 (1H, d, J=5.8 Hz), 4.55-4.49 (1H, m), 4.15 (1H, t, J=10.2 Hz), 3.48-3.37 (1H, m), 3.29-3.21 (1H, m), 3.18-3.08 (1H, m), 2.93 (2H, t, J=7.7 Hz), 2.56-2.52 (2H, m).

Example 9: 5-[3-[5-(3-chlorophenyl)-1H-imidazol-2-yl]chroman-6-yl]oxy-3,4-dihydro-1H-1,8-naphthyridin-2-one

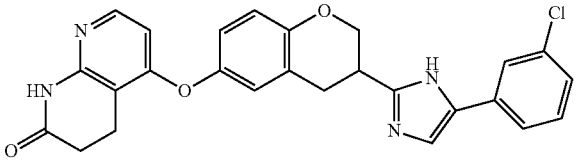

To a solution of 6-[(7-oxo-6,8-dihydro-5H-1,8-naphthyridin-4-yl)oxy]chromane-3-carboxylic acid (70 mg, 0.21 mmol) in DMF (2 mL) was added $K_2CO_3$ (56.86 mg, 0.41 mmol) and 2-bromo-1-(3-chlorophenyl)ethanone (96.06 mg, 0.41 mmol). The reaction was stirred for 3 days and further 2-bromo-1-(3-chlorophenyl)ethanone (96.06 mg, 0.41 mmol) and $K_2CO_3$ (56.86 mg, 0.41 mmol) were added. The mixture was stirred for 24 hrs, diluted with water (50 mL) and extracted with EtOAc (2×50 mL). The organic layers were washed with brine (50 mL). The combined aqueous layers were extracted with EtOAc (50 mL) and the combined organic layers were dried ($Na_2SO_4$), filtered and concentrated in vacuo to provide a solid.

The solid was dissolved in AcOH (3 mL) and $NH_4OAc$ (1.59 g, 20.57 mmol) was added. The mixture was heated in a sealed vial at 140° C. for 24 hrs. The mixture was added to sat. aq. $NaHCO_3$ (250 mL) and extracted with EtOAc (200 mL). The organic layer was washed with brine (2×100 mL), dried ($Na_2SO_4$), filtered and concentrated in vacuo. The residue was purified by flash column chromatography (0-5%

MeOH/DCM) to provide 5-[3-[5-(3-chlorophenyl)-1H-imidazol-2-yl]chroman-6-yl]oxy-3,4-dihydro-1H-1,8-naphthyridin-2-one (10.1 mg, 10% yield) as a brown solid.

LCMS (ES$^+$, Long): RT 3.04 min, m/z 473.1, 475.1 [M+H]$^+$ $^1$H NMR shows a mixture of confirmers:

$^1$H NMR (400 MHz, $d_6$-DMSO) δ: 12.40 (0.2H, s), 12.31 (0.8H, s), 10.46 (1H, s), 7.96 (1H, d, J=5.8 Hz), 7.80 (0.8H, t, J=1.8 Hz), 7.76-7.69 (2.2H, m), 7.36 (1H, t, J=7.9 Hz), 7.23-7.19 (1H, m), 7.03-7.00 (1H, m), 6.94 (0.2H, d, J=2.6 Hz) 6.91 (0.8H, d, J=2.6 Hz), 6.89 (0.7H, s), 6.88 (0.3H, s), 6.27 (1H, d, J=5.8 Hz), 4.54-4.48 (1H, m), 4.14 (1H, t, J=10.2 Hz), 3.44-3.36 (1H, m), 3.29-3.20 (1H, m), 3.16-3.08 (1H, m), 2.93 (2H, t, J=7.7 Hz), 2.57-2.52 (2H, m).

Example 10: 5-[3-[4-(benzofuran-3-yl)-1H-imidazol-2-yl]chroman-6-yl]oxy-3,4-dihydro-1H-1,8-naphthyridin-2-one

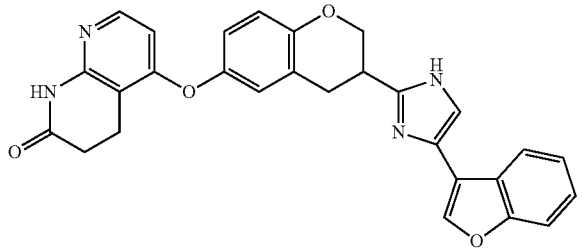

To a solution of 6-[(7-oxo-6,8-dihydro-5H-1,8-naphthyridin-4-yl)oxy]chromane-3-carboxylic acid (70 mg, 0.21 mmol) and $K_2CO_3$ (56.85 mg, 0.41 mmol) in DMF (2 mL) was added 1-(benzofuran-3-yl)-2-bromo-ethanone (98.35 mg, 0.41 mmol). The reaction was stirred for 1.5 hrs, diluted with water (10 mL) and extracted with EtOAc (80 mL). The organic layer was washed with water (30 mL), brine (30 mL), dried ($Na_2SO_4$), filtered and concentrated in vacuo. The residue was purified by flash column chromatography (0-5% MeOH/DCM) to provide a beige solid (104 mg).

The solid was dissolved in AcOH (4 mL), $NH_4OAc$ (1.49 g, 19.27 mmol) was added and the mixture heated at 140° C. in a sealed vial for 18 hrs. The reaction was cooled, added to water (40 mL), pH adjusted to 8-9 and extracted with EtOAc (2×150 mL). The combined organic layers were dried ($Na_2SO_4$), filtered and concentrated in vacuo. The residue was purified by flash column chromatography (0-10% MeOH/DCM) and prep HPLC to provide 5-[3-[4-(benzofuran-3 -yl)-1H-imidazol-2-yl]chroman-6-yl]oxy-3,4-dihydro-1H-1,8-naphthyridin-2-one (6 mg, 6% yield) as an off white solid.

LCMS (ES$^+$, Long): RT 2.98 min, m/z 479.2 [M+H]$^+$

1H NMR shows a mixture of confirmers:

1H NMR (400 MHz, $d_6$DMSO) δ: 12.42 (0.2H, br s), 12.21 (0.8H, brs), 10.47 (1H, s), 8.25 (0.2H, br s), 8.18 (0.8H, s), 8.11-8.04 (1H, m), 7.96 (1H, d, J=5.8 Hz), 7.58-7.56 (2H, m), 7.44-7.28 (2H, m), 7.03 (1H, d, J=2.4 Hz), 6.94 (0.2H, d, J=2.9 Hz), 6.92 (0.8H, d, J=2.6 Hz), 6.91 (0.8H, s), 6.89 (0.2H, s), 6.28 (1H, d, J=5.8 Hz), 4.57-4.50 (1H, m), 4.16 (1H, t, J=10.3 Hz), 3.48-3.39 (1H, m), 3.30-3.23 (1H, m), 3.19-3.10 (1H, m), 2.94 (2H, t, J=7.7 Hz), 2.58-2.52 (2H, m).

Example 11: 5-[3-[5-(3-pyridyl)-1H-imidazol-2-yl]chroman-6-yl]oxy-3,4-dihydro-1H-1,8-naphthyridin-2-one

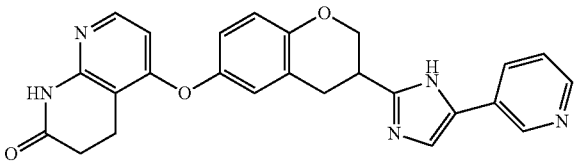

To a mixture of 6-[(7-oxo-6,8-dihydro-5H-1,8-naphthyridin-4-yl)oxy]chromane-3-carboxylic acid (80 mg, 0.24 mmol) in DMF (2 mL) was added $K_2CO_3$ (64.99 mg, 0.47 mmol) and 2-bromo-1-(3-pyridyl)ethanone hydrobromide (132.1 mg, 0.47 mmol). The reaction was 1 hr, diluted with water (20 mL) and extracted with EtOAc (50 mL). The organic layer was washed with water (30 mL) and brine (50 mL). The combined aqueous layers were extracted with EtOAc (50 mL). The combined organic layers were dried ($Na_2SO_4$), filtered and concentrated in vacuo. The residue was purified using flash column chromatography (0-5% MeOH/DCM) to provide a dark brown oil (100 mg). The brown oil was dissolved in AcOH (3 mL), $NH_4OAc$ (1.82 g, 23.51 mmol) was added and the mixture heated in a sealed vial at 140° C. for 18 hrs. The mixture was added to sat. aq. $NaHCO_3$ (250 mL) and EtOAc (50 mL) and stirred for 1 hr. The mixture was diluted with EtOAc (100 mL). The organic layer was washed with brine (100 mL) and the combined aqueous layers were extracted with EtOAc (100 mL). The combined organic layers were dried ($Na_2SO_4$), filtered, concentrated in vacuo and the residue was purified by prep HPLC to provide 5-[3-[5-(3-pyridyl)-1H-imidazol-2-yl]chroman-6-$_{yl]oxy-}$3,4-dihydro-1H-1,8-naphthyridin-2-one (7 mg, 7% yield) as an off white solid.

LCMS (ES$^+$, Long): RT 2.40 min, m/z 440.1 [M+H]$^+$ $^1$H NMR shows a mixture of confirmers:

$^1$H NMR (400 MHz, $d_6$-DMSO) δ: 12.26 (1H, s), 10.46 (1H, s), 8.97 (1H, s), 8.40-8.35 (1H, m), 8.10-8.04 (1H, m), 7.96 (1H, d, J=5.8 Hz), 7.75 (1H, s), 7.38-7.33 (1H, m), 7.04-7.00 (1H, m), 6.94 (0.2H, d, J=2.6 Hz), 6.92 (0.8H, d, J=2.6 Hz), 6.90 (0.8H, s), 6.88 (0.2H, s), 6.27 (1H, d, J=5.8 Hz), 4.55-4.48 (1H, m), 4.15 (1H, t, J=10.3 Hz), 3.47-3.38 (1H, m), 3.29-3.21 (1H, m), 3.18-3.10 (1H, m), 2.94 (2H, t, J=7.7 Hz), 2.57-2.52 (2H, m).

Example 12: 5-[3-[5-(4-methylsulfonylphenyl)-1H-imidazol-2-yl]chroman-6-yl]oxy-3,4-dihydro-1H-1,8-naphthridin-2-one

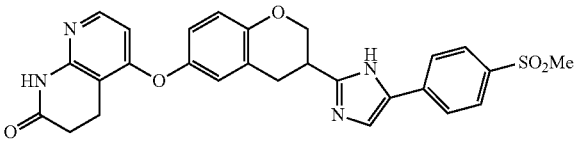

To a stirred mixture of 6-[(7-oxo-6,8-dihydro-5H-1,8-naphthyridin-4-yl)oxy]chromane-3-carboxylic acid (80 mg, 0.24 mmol) in DMF (2 mL) was added $K_2CO_3$ (64.99 mg, 0.47 mmol) and 4-Methylsulfonyl alpha-bromoacetophenone (130.31 mg, 0.47 mmol). The reaction was stirred for 1 hr, diluted with water (20 mL) and extracted with EtOAc (50 mL). The organic layer was washed with water (30 mL) and brine (50 mL). The combined aqueous layers were extracted with EtOAc (50 mL). The combined organic layers were dried ($Na_2SO_4$), filtered and concentrated in vacuo to provide a dark orange solid (100 mg).

The orange solid was dissolved in AcOH (3 mL), $NH_4OAc$ (1.81 g, 23.51 mmol) was added and the mixture heated in a sealed vial at 140° C. for 18 hrs. The mixture was added to sat. aq. $NaHCO_3$ (250 mL) and EtOAc (50 mL) and stirred until neutralised. Further EtOAc (100 mL) was added and the organic layer was washed with brine (100 mL). The combined aqueous layers were extracted with EtOAc (100 mL). The combined organic layers were dried ($Na_2SO_4$), filtered and concentrated in vacuo. The residue was purified using flash column chromatography (0-5% MeOH/DCM and 0-5% MeOH/DCM) and prep HPLC to provide 5-[3-[5-(4-methylsulfonylphenyl)-1H-imidazol-2-yl]chroman-6-yl]oxy-3,4-dihydro-1H-1,8-naphthyridin-2-one (26.8 mg, 22% yield) as a pale yellow solid.

LCMS ($ES^+$, Long): RT 2.62 min, m/z 517.1 $[M+H]^+$ $^1H$ NMR shows a mixture of confirmers:

$^1H$ NMR (400 MHz, $d_6$-DMSO) δ: 12.35 (1H, s), 10.46 (1H, s), 8.02-7.95 (3H, m), 7.90-7.84 (3H, m), 7.04-7.00 (1H, m), 6.95-6.87 (2H, m), 6.27 (1H, d, J=5.8 Hz), 4.56-4.49 (1H, m), 4.15 (1H, t, J=10.2 Hz), 3.48-3.38 (1H, m), 3.28-3.21 (1H, m), 3.20 (3H, s), 3.18-3.09 (1H, m), 2.94 (2H, t, J=7.7 Hz), 2.57-2.52 (2H, m).

Example 13: 5-[3-[5-(4-fluorophenyl)-1H-imidazol-2-yl]chroman-6-yl]oxy-3,4-dihydro-1H-1,8-naphthyridin-2-one

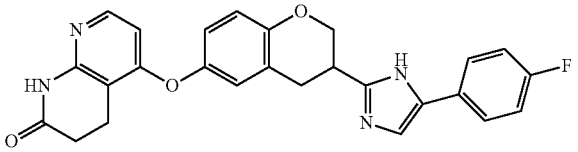

To a solution of 6-[(7-oxo-6,8-dihydro-5H-1,8-naphthyridin-4-yl)oxy]chromane-3-carboxylic acid (80 mg, 0.24 mmol) in DMF (2 mL) was added $K_2CO_3$ (64.99 mg, 0.47 mmol) and p-fluorophenacyl bromide (102.05 mg, 0.47 mmol). The reaction was stirred for 1 hr, diluted with water (20 mL) and extracted with EtOAc (50 ml). The organic layer was washed with water (30 mL) and brine (50 mL). The combined aqueous layers were extracted with EtOAc (50 mL). The combined organic layers were combined dried ($Na_2SO_4$), filtered, concentrated in vacuo and purified by flash column chromatography (0-5% MeOH/DCM) to provide a dark brown oil.

The brown oil was dissolved in AcOH (3 mL), $NH_4OAc$ (1.81 g, 23.51 mmol) was added and the mixture heated in a sealed vial at 140° C. for 18 hrs. The mixture was added to sat. aq. $NaHCO_3$ (100 mL) and EtOAc (50 mL) and stirred until neutralised. The mixture was diluted with EtOAc (50 mL) and the combined organic layers were washed with brine (50 mL). The combined aqueous layers were extracted with EtOAc (50 mL). The combined organic layers were dried ($Na_2SO_4$), filtered and concentrated in vacuo. The residue was purified by flash column chromatography (0-5% MeOH/DCM) and prep HPLC to provide 5-[3-[5-(4-fluorophenyl)-1H-imidazol-2-yl]chroman-6-yl]oxy-3,4-dihydro-1H-1,8-naphthyridin-2-one (7.7 mg, 7% yield) as an off white solid.

LCMS: ($ES^+$, Long): RT 2.76 min, m/z 457.2 $[M+H]^+$ $^1H$ NMR shows a mixture of confirmers:

$^1H$ NMR (400 MHz, $d_6$-DMSO) δ: 12.33 (0.2H, s), 12.11 (0.8H, s), 10.46 (1H, s), 7.96 (1H, d, J=5.8 Hz), 7.81-7.74 (1.7H, m), 7.70-7.64 (0.3H, m), 7.58 (0.8H, s), 7.29-7.23 (0.5H, m), 7.20-7.12 (1.7H, m), 7.03-6.99 (1H, m), 6.94 (0.2H, d, J=2.6 Hz), 6.91 (0.8H, d, J=2.6 Hz), 6.90 (0.8H, s), 6.88 (0.2H, s), 6.27 (1H, d, J=5.8 Hz), 4.54-4.48 (1H, m), 4.13 (1H, t, J=10.3 Hz), 3.45-3.36 (1H, m), 3.29-3.19 (1H, m), 3.16-3.07 (1H, m), 2.94 (2H, t, J=7.7 Hz), 2.57-2.53 (2H, m).

Example 14: 5-[3-[5-(1,3-benzodioxol-5-yl)-1H-imidazol-2-yl]chroman-6-yl]oxy-3,4-dihydro-1H-1,8-naphthyridin-2-one

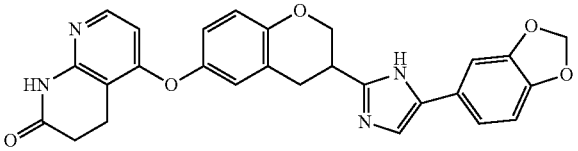

To a mixture of 6-[(7-oxo-6,8-dihydro-5H-1,8-naphthyridin-4-yl)oxy]chromane-3-carboxylic acid (160 mg, 0.47 mmol) in DMF (4 mL) was added $K_2CO_3$ (129.95 mg, 0.94 mmol) and 1-(1,3-benzodioxol-5-yl)-2-bromoethanone (228.53 mg, 0.94 mmol). The reaction was stirred for 2 hrs, diluted with water (20 mL) and extracted with EtOAc (50 mL). The organic layer was washed with water (30 mL) and brine (50 mL). The combined aqueous layers were extracted with EtOAc (50 mL). The combined organic layers were dried ($Na_2SO_4$), filtered, concentrated in vacuo and residue was purified by flash column chromatography (0-5% MeOH/DCM) to provide a yellow oil.

The yellow oil was dissolved in AcOH (6 mL), $NH_4OAc$ (3.62 g, 47.01 mmol) was added and the mixture heated in a sealed tube at 140° C. for 3 hrs. The mixture was diluted with sat. aq. $NaHCO_3$ (250 mL) and EtOAc (50 mL) and stirred till neutralised. The biphasic mixture was diluted with EtOAc (100 mL). The organic layer was washed with brine (100 mL) and the combined aqueous layers were extracted with EtOAc (100 mL). The combined organic layers were dried ($Na_2SO_4$), filtered and concentrated invacuo. The residue was purified using flash column chromatography (0-5% DCM/MeOH) and HPLC prep to provide 5-[3-[5-(1,3-benzodioxol-5-yl)-1H-imidazol-2-yl]chroman-6-yl]oxy-3,4-dihydro-1H-1,8-naphthyridin-2-one (13.8 mg, 6% yield) as an off white solid.

LCMS ($ES^+$, Long): RT 2.71 min, m/z 483.2 $[M+H]^+$ $^1H$ NMR shows a mixture of confirmers:

$^1H$ NMR (400 MHz, $d_6$-DMSO) δ: 12.19 (0.2H, s), 12.02 (0.8H, s), 10.45 (1H, s), 7.95 (1H, d, J=5.9 Hz), 7.50-7.45 (1H, m), 7.30-7.10 (2H, m), 7.01-6.98 (1H, m), 6.94-6.84 (3H, m), 6.26 (1H, d, J=5.7 Hz), 6.05-5.96 (2H, m), 4.52-4.46 (1H, m), 4.11 (1H, t, J=10.2 Hz), 3.41-3.34 (1H, m), 3.27-3.18 (1H, m), 3.13-3.05 (1H, m), 2.93 (2H, t, J=7.7 Hz), 2.57-2.52 (2H, m).

Example 15: 5-[3-[5-(2,3-dihydro-1,4-benzodioxin-6-yl)-1H-imidazol-2-yl]chroman-6-yl]oxy-3,4-dihydro-1H-1,8-naphthyridin-2-one

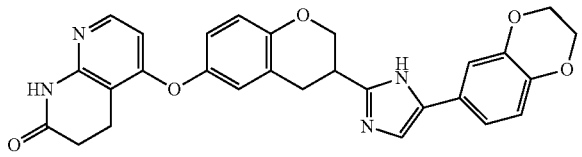

To a solution of 6-[(7-oxo-6,8-dihydro-5H-1,8-naphthyridin-4-yl)oxy]chromane-3-carboxylic acid (160 mg, 0.47 mmol) in DMF (4 mL) was added $K_2CO_3$ (129.95 mg, 0.94 mmol) and 3,4-(Ethylenedioxy)phenacyl bromide (168 mg, 0.65 mmol). The reaction was stirred for 1 hr, diluted with water (20 mL) and extracted with EtOAc (50 mL). The organic layer was washed with water (30 mL) and brine (50 mL). The combined aqueous layers were extracted with EtOAc (50 mL). The combined organic layers were dried ($Na_2SO_4$), filtered, concentrated invacuo and residue purified by flash column chromatography (0-5% MeOH/DCM) to provide a yellow oil.

The yellow oil was dissolved in AcOH (6 mL), $NH_4OAc$ (3.62 g, 47.01 mmol) was added and the mixture heated in a sealed tube at 140° C. for 1.5 hrs, cooled and stirred for a further 90 hrs. The mixture was diluted with sat. aq. $NaHCO_3$ (150 mL), EtOAc (50 mL) and stirred till neutralised. The mixture was diluted with further EtOAc (50 ml). The organic layer was washed with brine (100 mL) and the combined aqueous layers were extracted with EtOAc (100 mL). The combined organic layers were dried ($Na_2SO_4$), filtered, concentrated in vacuo. The residue was purified by flash column chromatography (0-5% DCM/MeOH) and prep HPLC to provide 5-[3-[5-(2,3-dihydro-1,4-benzodioxin-6-yl)-1H-imidazol-2-yl]chroman-6-yl]oxy-3,4-dihydro-1H-1,8-naphthyridin-2-one (21.6 mg, 9% yield) as an off white solid LCMS: (ES$^+$, Long): RT 2.73 min, m/z 497.1 $[M+H]^+$ $^1$H NMR shows a mixture of confirmers:

$^1$H NMR (400 MHz, $d_6$-DMSO) δ: 12.02 (1H, s), 10.47 (1H, s), 7.96 (1H, d, J=5.8 Hz), 7.42 (1H, s), 7.24-7.15 (2H, m), 7.02-6.98 (1H, m), 6.93 (0.2H, d, J=2.7 Hz), 6.91 (0.8H, d, J=2.7 Hz), 6.89 (0.8H, s), 6.88 (0.2H, s), 6.82 (1H, d, J=8.5 Hz), 6.27 (1H, d, J=5.8 Hz), 4.53-4.46 (1H, m), 4.24 (4H, s), 4.12 (1H, t, J=10.3 Hz), 3.42-3.34 (1H, m), 3.27-3.18 (1H, m), 3.15-3.06 (1H, m), 2.93 (2H, t, J=7.7 Hz), 2.57-2.52 (2H, m).

Example 16: 5-[[3-(4-phenyl-1H-imidazol-2-yl)-2H-chromen-6-yl]oxy]-3,4-dihydro-1H-1,8-naphthyridin-2-one

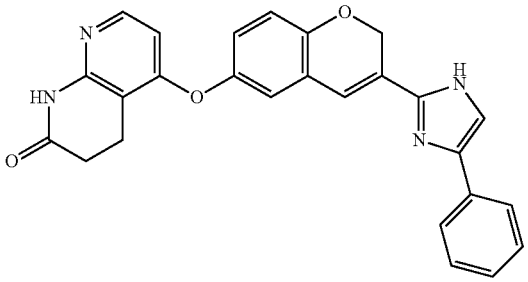

To a solution of 6-[(7-oxo-6,8-dihydro-5H-1,8-naphthyridin-4-yl)oxy]-2H-chromene-3-carboxylic acid (354 mg, 1.05 mmol) in DMF (7 mL) was added $K_2CO_3$ (289.13 mg, 2.09 mmol) and 2-bromoacetophenone (0.31 mL, 2.09 mmol). The reaction was stirred for 30 mins at room temperature, diluted with water (30 mL) and extracted with EtOAc (2×50 mL). The combined organic layers were washed with brine (30 mL), dried ($Na_2SO_4$), filtered and 60 concentrated in vacuo to provide a brown solid.

The solid was dissolved in AcOH (10 mL), $NH_4OAc$ (6.45 g, 83.71 mmol) was added and the reaction heated in a sealed tube at 130° C. for 16 hrs. The mixture was cooled, concentrated in vacuo and the residue dissolved in EtOAc (50 mL). The organic layer was washed with sat. aq. $NaHCO_3$ (2×50 mL) and water (1×50 mL). The combined aqueous layers were extracted with EtOAc (50 mL) and the combined organic layers were dried ($Na_2SO_4$), filtered and concentrated in vacuo. The residue was purified by flash column chromatography (0-5% MeOH/DCM) and prep HPLC to provide 5-[[3-(4-phenyl-1H-imidazol-2-yl)-2H-chromen-6-yl]oxy]-3,4-dihydro-1H-1,8-naphthyridin-2-one (21 mg, 5% yield) as a yellow solid.

LCMS (ES$^+$, Long) RT 3.14 min, m/z 437.2 $[M+H]^+$ $^1$HNMR shows a mixture of confirmers:

$^1$H NMR (400 MHz, $d_6$-DMSO) δ: 12.73 (0.8H, br s), 12.70 (0.2H, br s), 10.48 (1H, s), 7.98 (1H, d, J=5.8 Hz), 7.86-7.75 (2H, m), 7.53-7.28 (3H, m), 7.25-7.18 (1H, m), 7.15 (1H, br s), 7.02 (1H, t, J=1.5 Hz), 6.95 (2H, d, J=1.6 Hz), 6.33 (1H, d, J=5.8 Hz), 5.27 (1.5H, s), 5.23 (0.5H, s), 2.98-2.91 (2H, m), 2.58-2.52 (2H, m).

Example 17: 5-[3-(3-phenyl-1,2,4-oxadiazol-5-yl) chroman-6-yl]oxy-3,4-dihydro-1H-1,8-naphthyridin-2-one

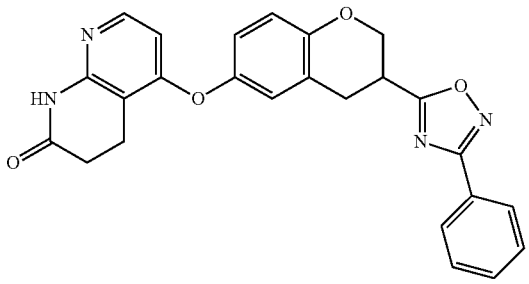

To a mixture of 6-[(7-oxo-6,8-dihydro-5H-1,8-naphthyridin-4-yl)oxy]chromane-3-carboxylic acid (62 mg, 0.18 mmol), N-Hydroxybenzenecarboximidamide (26 mg, 0.19 mmol) and DIPEA (0.05 mL, 0.27 mmol) in DMF (2 mL) was added HATU (79.66 mg, 0.21 mmol). The reaction was stirred for 22 hrs, quenched with water (15 mL) and extracted with EtOAc (50 mL). The aqueous layer was diluted with EtOAc (50 mL), filtered, diluted with further EtOAc (150 mL) and brine (50 mL), separated and the combined organic layers were dried ($Na_2SO_4$), filtered and concentrated in vacuo.

The residue was dissolved in pyridine (3 mL, 37.09 mmol) and heated at 100° C. in a sealed vial for 20 hrs. The mixture was cooled, concentrated in vacuo and the residue was purified by flash column chromatography (0-5% MeOH/DCM) and prep HPLC to provide 5-[3-(3-phenyl-1,2,4-oxadiazol-5-yl)chroman-6-yl]oxy-3,4-dihydro-1H-1,8-naphthyridin-2-one (5 mg, 6% yield) as an off white solid.

LCMS (ES$^+$, Long): RT 4.11 min, m/z 441.2 $[M+H]^+$ $^1$H NMR shows a mixture of confirmers:

$^1$H NMR (400 MHz, $d_6$-DMSO) δ: 10.47 (1H, s), 8.03-7.97 (2H, m), 7.96 (1H, d, J=5.8 Hz), 7.64-7.54 (3H, m), 7.07 (1H, d, J=2.5 Hz), 6.95 (0.3H, d, J=2.7 Hz), 6.93 (0.7H, d, J=2.7 Hz), 6.91 (0.7H, s), 6.89 (0.3H, s), 6.26 (1H, d, J=5.8 Hz), 4.63-4.56 (1H, m), 4.48-4.40 (1H, dd, J=7.4 Hz), 3.98-3.88 (1H, m), 3.40-3.25 (2H, m), 2.93 (2H, t, J=7.4, 10.9 Hz), 2.57-2.53 (2H, m).

Example 18: 5-[3-(5-phenyl-1 H-pyrazol-3-yl)chroman-6-yl]oxy-3,4-dihydro-1H-1,8-naphthyridin-2-one

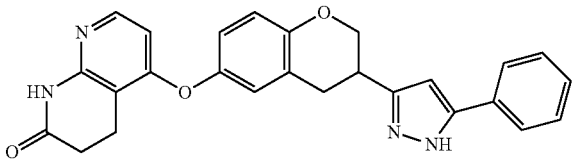

Step 1:

To a mixture of 6-[(7-oxo-6,8-dihydro-5H-1,8-naphthyridin-4-yl)oxy]chromane-3-carboxylic acid (150 mg, 0.44 mmol) and N,O-Dimethylhydroxylamine hydrochloride (64.49 mg, 0.66 mmol) in DMF (3 mL) was added DIPEA (0.31 mL, 1.76 mmol) and HATU (201.1 mg, 0.53 mmol). The mixture was stirred for 24 hrs, diluted with EtOAc (100 mL), washed with water (233 30 mL), brine (30 mL), dried ($Na_2SO_4$), filtered and concentrated in vacuo. The residue was purified by flash column chromatography (0-4% MeOH/DCM) to provide N-methoxy-N-methyl-6-[(7-oxo-6,8-dihydro-5H-1,8-naphthyridin-4-yl)oxy]chromane-3-carboxamide (133 mg, 79% yield) as an off white foam.

LC-MS (ES$^+$, Short): RT 1.37 min, m/z 384.2 [M+H]$^+$ $^1$H NMR (400 MHz, $CDCl_3$) δ: 8.12 (1H, s), 7.96 (1H, d, J=6.0 Hz), 6.90-6.86 (1H, m), 6.85-6.80 (2H, m), 6.31 (1H, d, J=5.9 Hz), 4.46-4.40 (1H, m), 4.04 (1H, t, J=10.5 Hz), 3.76 (3H, s), 3.42-3.32 (1H, m), 3.24 (3H, s), 3.20-3.11 (1H, m), 3.06 (2H, t, J=7.5 Hz), 2.90-2.83 (1H, m), 2.73-2.66 (2H, m).

Step 2:

To a solution of phenylacetylene (0.09 mL, 0.85 mmol) in THF (6 mL) at −78° C. was added dropwise n-Butyllithium solution (0.34 mL, 0.85 mmol, 2.5M in THF) and the solution stirred for 30 mins. A solution of N-methoxy-N-methyl-6-[(7-oxo-6,8-dihydro-5H-1,8-naphthyridin-4-yl)oxy]chromane-3-carboxamide (130 mg, 0.34 mmol) in THF (2 mL) was added dropwise and the solution stirred for 3 hrs at −78° C. then warmed to room temperature over 1 hr. The reaction was quenched with sat. aq. $NH_4Cl$ (20 mL) and extracted with EtOAc (100 mL). The organic layer was washed with brine (20 mL), dried ($Na_2SO_4$), filtered and concentrated in vacuo. The residue was purified by flash column chromatography (0-5% MeOH/DCM) to provide 5-[3-(3-phenylprop-2-ynoyl)chroman-6-yl]oxy-3,4-dihydro-1H-1,8-naphthyridin-2-one (122 mg, 61% yield) as a yellow solid.

LCMS (ES$^+$, Short): RT 1.76 min, m/z 425.3 [M+H]$^{+.}$

Step 3:

To a solution of 5-[3-(3-phenylprop-2-ynoyl)chroman-6-yl]oxy-3,4-dihydro-1H-1,8-naphthyridin-2-one (122 mg, 0.21 mmol) in $^t$BuOH (2 mL) was added hydrazine hydrate (0.02 mL, 0.41 mmol) and the mixture heated to 85° C. for 18 hrs. The mixture was cooled, concentrated in vacuo and purified by flash column chromatography (0-5% MeOH/DCM) and prep HPLC to provide 5-[3-(5-phenyl-1H-pyrazol-3-yl)chroman-6-yl]oxy-3,4-dihydro-1H-1,8-naphthyridin-2-one (20 mg, 22% yield) as an off white solid.

LCMS (ES$^+$, Long): RT 3.71 min, m/z 439.2 [M+H]$^+$ $^1$H NMR shows a mixture of confirmers:

$^1$H NMR (400 MHz, $d_6$-DMSO) δ: 13.14 (0.5H, br s), 12.88 (0.5H, br s), 10.47 (1H, s), 7.96 (1H, d, J=5.8 Hz), 7.82-7.65 (2H, m), 7.50-7.24 (3H, m), 6.99 (1H, d, J=2.4 Hz), 6.96-6.85 (2H, m), 6.70-6.57 (1H, m), 6.27 (1H, d, J=5.8 Hz), 4.50-4.40 (1H, m), 4.19-4.02 (1H, m), 3.40-3.30 (1H, m), 3.17-3.03 (2H, m), 2.93 (2H, t, J=7.7 Hz), 2.57-2.52 (2H, m).

Example 19: 5- [[(3S)-3-(4-phenyl-1H-imidazol-2-yl)-2,3-dihydro-1,4-benzodioxin-6-yl]oxy]-3,4-dihydro-1H-1,8-naphthyridin-2-one

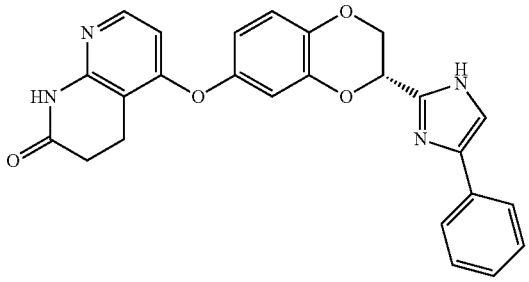

Step 1:

To a suspension of NaH (60%, 0.82 g, 20.58 mmol) in DMF (20 mL) at 0° C. was added slowly a solution of 2-hydroxy-5-tetrahydropyran-2-yloxy-benzaldehyde (3.43 g, 15.43 mmol) in DMF (20 mL) and the mixture stirred for 1 hr. [(2R)-oxiran-2-yl]methyl 3-nitrobenzenesulfonate (4.g, 15.43 mmol) was added, the mixture warmed to room temperature and heated at 70° C. for 18 hrs. The reaction was cooled and concentrated in vacuo. The residue was dissolved in DCM (200 mL), washed with aq. 1 M HCl (100 mL), sat. aq. $Na_2CO_3$ (100 mL) and brine (50 mL). The aqueous layers were extracted with DCM (2×200 mL) and the combined organic layers were dried ($Na_2SO_4$), filtered and concentrated in vacuo. The residue was purified by flash column chromatography (0-50% EtOAc/pet. Ether) to provide 2-[[(2R)-oxiran-2-yl]methoxy]-5-tetrahydropyran-2-yloxy-benzaldehyde (2.06 g, 48% yield) as a yellow oil.

$^1$H NMR (400 MHz, $CDCl_3$) δ: 10.47 (1H, s), 7.51 (1H, d, J=3.1 Hz), 7.26-7.21 (1H, m), 6.93 (1H, d, J=8.8 Hz), 5.35 (1H, t, J=3.3 Hz), 4.34 (1H, dd, J=2.9, 11.2 Hz), 4.02 (1H, dd, J=5.7, 11.1 Hz), 3.93-3.83 (1H, m), 3.63-3.56 (1H, m), 3.41-3.35 (1H, m), 2.93 (1H, t, J=4.5 Hz), 2.79-2.75 (1H, m), 2.03-1.91 (1H, m), 1.88-1.79 (2H, m), 1.74-1.50 (3H, m).

Step 2:

To a solution of 2-[[(2R)-oxiran-2-yl]methoxy]-5-tetrahydropyran-2-yloxy-benzaldehyde (2.06 g, 7.39 mmol) in DCM (25 mL) was added mCPBA (2.55 g, 14.79 mmol). The mixture was stirred for 18 hrs, filtered and concentrated in vacuo. The residue was dissolved in $Et_2O$, washed with aq. sodium thiosulphate, sat. aq. $Na_2CO_3$, brine, dried ($Na_2SO_4$), filtered and concentrated in vacuo to provide crude [2-[[(2R)-oxiran-2-yl]methoxy]-5-tetrahydropyran-2-yloxy-phenyl]formate (2.08 g, 95% yield).

$^1$H NMR (400 MHz, $CDCl_3$) δ: 8.26 (1H, s), 6.97-6.89 (2H, m), 6.87 (1H, d, J=2.6 Hz), 5.30 (1H, t, J=3.2 Hz), 4.19 (1H, dd, J=3.3, 11.4 Hz), 3.96 (1H, dd, J=5.6, 11.2 Hz), 3.92-3.83 (1H, m), 3.63-3.55 (1H, m), 3.32-3.26 (1H, m), 2.89-2.85 (1H, m), 2.70 (1H, dd, J=2.7, 4.9 Hz), 2.02-1.78 (3H, m), 1.73-1.58 (3H, m).

Step 3:

To a solution of [2-[[(2R)-oxiran-2-yl]methoxy]-5-tetrahydropyran-2-yloxy-phenyl] formate (2.08 g, 7.07 mmol) in MeOH (42.3 mL) was added $Na_2CO_3$ (2.1 g, 19.79 mmol) and the mixture stirred for 70 hrs. The mixture was diluted with DCM and washed with water. The aqueous layer was extracted with DCM and the combined organic layers were dried ($Na_2SO_4$), filtered, and concentrated in vacuo. The residue was purified by flash column chromatography (0-50% EtOAc/pet. Ether) to provide [(3S)-6-tetrahydropyran-2-yloxy-2,3-dihydro-1,4-benzodioxin-3-yl]methanol (1.76 g, 94% yield) as a clear, pale yellow oil.

LC/MS: (ES$^+$, Short): RT 1.51 min, m/z 267.0 [M+H]$^+$ $^1$H NMR (400 MHz, $CDCl_3$) δ: 6.78 (1H, d, J=8.9 Hz), 6.67 (1H, d, J=3.0 Hz), 6.59-6.53 (1H, m), 5.29-5.24 (1H, m), 4.28-4.21 (2H, m), 4.06 (1H, dd, J=8.2, 11.9 Hz), 3.96-3.79 (2H, m), 3.63-3.55 (1H, m), 2.03-1.78 (4H, m), 1.72-1.52 (4H, m).

Step 4

[(3S)-6-tetrahydropyran-2-yloxy-2,3-dihydro-1,4-benzodioxin-3-yl]methanol (500 mg, 1.88 mmol) was dissolved in DCM (8 mL) and cooled to 0° C. DMP (0.88 g, 2.07 mmol) was added and the reaction was stirred for 3 hrs. The mixture was diluted with sat. aq. $NaHCO_3$ (10 mL)/sat. aq. sodium thiosulphate (10 mL) and stirred for 1 hr. The layers were separated and the aqueous layer was extracted with DCM (15 mL), The combined organic layers were dried ($Na_2SO_4$), filtered and concentrated in vacuo to provide crude (3R)-6-tetrahydropyran-2-yloxy-2,3-dihydro-1,4-benzodioxine-3-carbaldehyde (586 mg, 118% yield) as an orange oil.

Step 5:

A solution of phenylglyoxal hydrate (285.57 mg, 1.88 mmol) in MeOH (10 mL) was added dropwise to a stirred suspension of crude (3R)-6-tetrahydropyran-2-yloxy-2,3-dihydro-1,4-benzodioxine-3-carbaldehyde (496 mg, 1.88 mmol) and $NH_4OAc$ (704.54 mg, 9.14 mmol) in MeOH (8 mL). The reaction mixture was stirred for 18 hrs and concentrated in vacuo. The residue was partitioned between sat. aq. $NaHCO_3$ (20 mL) and DCM (20 mL). The organic phase was dried ($Na_2SO_4$), filtered and concentrated in vacuo. The residue was purified by column chromatography (0-30% EtOAc/pet. Ether) to provide 4-phenyl-2-[(3S)-6-tetrahydropyran-2-yloxy-2,3-dihydro-1,4-benzodioxin-3-yl]-1H-imidazole (550 mg, 77%).

LC/MS (ES$^+$, Short): RT 1.57 min, m/z 379.2 [M+H]$^+$

Step 6:

To a solution of 4-phenyl-2-[(3S)-6-tetrahydropyran-2-yloxy-2,3-dihydro-1,4-benzodioxin-3-yl]-1H-imidazole (550 mg, 1.45 mmol) in DMF (9.4 mL), at 0° C., was added NaH (60%, 75.57 mg, 1.89 mmol) and the mixture stirred at this temperature for 1 hr. 2-(Trimethylsilyl)ethoxymethyl chloride (257.23 uL, 1.45 mmol) was added dropwise at 0° C. and the mixture stirred for 16 hrs at room temperature. The mixture was quenched with sat. aq. $NH_4Cl$ (5 mL) and extracted with EtOAc (25 mL). The organic layer was washed with water (25 mL) and the combined aqueous layers were extracted with EtOAc (25 mL). The combined organic layers were dried ($Na_2SO_4$), filtered and concentrated in vacuo to provide crude trimethyl-[2-[[4-phenyl-2-[(3S)-6-tetrahydropyran-2-yloxy-2,3-dihydro-1,4-benzodioxin-3-yl]imidazol-1-yl]methoxy]ethyl]silane (1.30 g, 176% yield) as a pale yellow oil.

LC/MS: (ES$^+$, Short): RT 2.36 min, m/z 509.6 [M+H]$^+$

Step 7:

Trimethyl-[2-[[4-phenyl-2-[(3S)-6-tetrahydropyran-2-yloxy-2,3-dihydro-1,4-benzodioxin-3-yl]imidazol-1-yl]methoxy]ethyl]silane (739 mg, 1.45 mmol) was dissolved in MeOH (5 mL), loaded onto a pre-wetted 5 g SCX cartridge and washed with methanol (3×15 mL), 1 N $NH_3$/MeOH (3×15 mL), and product fractions were concentrated in vacuo. The residue was purified by column chromatography (0-25% EtOAc/pet. Ether) to provide (3S)-3-[4-phenyl-1-(2-trimethylsilylethoxymethyl)imidazol-2-yl]-2,3-dihydro-1,4-benzodioxin-6-ol (260 mg, 42% yield) as a pale yellow oil.

LC/MS: (ES$^+$, Short): RT 2.02 min, m/z 425.4 [M+H]$^+$ $^1$H NMR (400 MHz, $CDCl_3$) δ: 7.78-7.73 (2H, m), 7.40-7.35 (2H, m), 7.33 (1H, s), 7.29-7.27 (0.5H, m), 7.25-7.23 (0.5H, m), 6.77 (1H, d, J=8.8 Hz), 6.52 (1H, d, J=3.0 Hz), 6.40-6.29 (2H, m), 5.52 (1H, d, J=10.8 Hz), 5.39-5.32 (2H, m), 4.61-4.51 (2H, m), 3.59 (2H, t, J=8.3 Hz), 0.97-0.87 (2H, m), 0.00-0.02 (9H, s).

Step 8:

(3S)-3-[4 -phenyl-1-(2 -trimethylsilylethoxymethyl)imidazol-2-yl]-2,3-dihydro-1,4-benzodioxin-6-ol (115 mg, 0.27 mmol), 5-fluoro-3,4-dihydro-1H-1,8-naphthyridin-2-one (45 mg, 0.27 mmol) and $Cs_2CO_3$ (220.63 mg, 0.68 mmol) in DMF (2 mL) was irradiated at 150° C. for 2 hrs. The resultant was partitioned between EtOAc (50 mL) and water (50 mL). To the aqueous layer was added $NH_4Cl$ (until pH to 5) and the aqueous layer was extracted with EtOAc (5×50 mL). The combined organic layers were washed with brine (3×50 mL), dried ($Na_2SO_4$), filtered and concentrated in vacuo. The residue was redissolved in EtOAc (100 mL), washed with brine (2×100 mL), dried ($Na_2SO_4$), filtered and concentrated in vacuo to provide crude 5-[[(3S)-3-[4-phenyl-1-(2-trimethylsilylethoxymethyl)imidazol-2-yl]-2,3-dihydro-1,4-benzodioxin-6-yl]oxy]-3,4-dihydro-1H-1,8-naphthyridin-2-one (105 mg, 68% yield) as an orange-brown solid.

LC/MS: (ES$^+$, Short): RT 2.08 min, m/z 571.3 [M+H]$^+$

Step 9:

To a solution of 5-[[(3S)-3-[4-phenyl-1-(2-trimethylsilylethoxymethyl)imidazol-2-yl]-2,3-dihydro-1,4-benzodioxin-6-yl]oxy]-3,4-dihydro-1H-1,8-naphthyridin-2 -one (105 mg, 0.18 mmol) in EtOH (3 mL) was added aq. 1N HCl (4 mL, 4 mmol) and the mixture stirred at 70° C. for 16 hrs. The mixture was concentrated in vacuo. The residue was dissolved in MeOH (5 mL)/DCM (50 mL) and washed with sat. aq. $Na_2CO_3$ (25 mL). The aqueous layer was washed with DCM (4×50 mL) and EtOAc (50 mL). The combined organic layers were dried ($Na_2SO_4$), filtered and concentrated in vacuo. The residue was purified by flash column chromatography (0-100% EtOAc/pet. Ether), reverse phase flash chromatography (20-60% MeCN/water/0.1% formic acid) and SCX-2 to provide 5-[[(3S)-3-(4-phenyl-1H-imidazol-2-yl)-2,3-dihydro-1,4-benzodioxin-6-yl]oxy]-3,4-dihydro-1H-1,8-naphthyridin-2-one (4.72 mg, 5% yield) as an off-white solid.

LCMS (ES$^+$, Long): RT 3.01 min, m/z 441.1 [M+H]$^+$

Chiral ee of enantiomer—96.8% [RT—7.70 mins]

$^1$H NMR (400 MHz, $d_6$-DMSO) δ: 12.84 (0.2H, br s), 12.52 (0.8H, s), 10.46 (1H, m), 7.97 (1H, d, J=5.8 Hz), 7.84-7.62 (3H, m), 7.42-7.30 (3H, m), 7.02 (2H, d, J=8.8 Hz), 6.80 (1H, d, J=2.9 Hz), 6.69 (1H, dd, J=8.8, 2.9 Hz) 6.29 (1H, d, J=5.8 Hz), 5.39 (1H, d, J=7.0 Hz), 4.62 (1H, dd,

J=2.5, 11.6 Hz), 4.44 (1H, dd, J=8.3, 11.6 Hz), 2.91 (2H, t, J=7.7 Hz), 2.56-2.51 (2H, m).

Example 20: 5-[[(3R)-3-(4-phenyl-1H-imidazol-2-yl)-2,3-dihydro-1,4-benzodioxin-6-yl]oxy]-3,4-dihydro-1H-1,8-naphthyridin-2-one

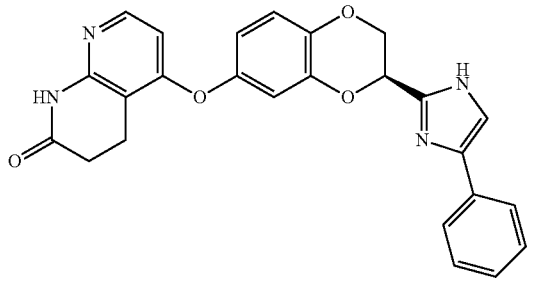

Prepared in a similar way to Example 19 using (2S)-oxiran-2-yl]methyl 3-nitrobenzenesulfonate instead of (2R)-oxiran-2-yl]methyl 3-nitrobenzenesulfonate.

LCMS (ES$^+$, Long): RT 3.02 min, m/z 441.1 [M+H]$^+$

Chiral ee of enantiomer 92.8% [RT 8.98 mins]

$^1$H NMR (400 MHz, $d_6$-DMSO) δ: 12.84 (0.2H, br s), 12.55 (0.8H, br s), 10.46 (1H, s), 7.97 (1H, d, J=5.8 Hz), 7.82-7.63 (3H, m), 7.45-7.28 (3H, m), 7.02 (1H, d, J=8.8 Hz), 6.80 (1H, d, J=2.8 Hz), 6.69 (1H, dd, J=2.8, 8.8 Hz), 6.29 (1H, d, J=5.8 Hz), 5.42-5.33 (1H, m), 4.65-4.57 (1H, m), 4.48-4.39 (1H, m), 2.91 (2H, t, J=7.7 Hz), 2.66-2.51 (2H, m).

Example 21: 2-Methyl-4-[3-(5-phenyl-1H-imidazol-2-yl)chroman-6-yl]oxy-pyridine

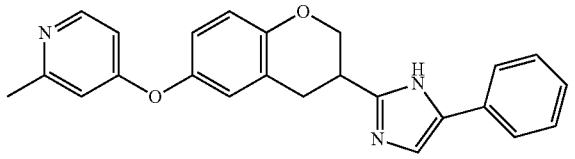

Step 1:

A mixture of 4-fluoro-2-methylpyridine (100 mg, 0.9 mmol), 6-hydroxychromane-3-carboxylic acid (199.99 mg, 1.03 mmol) and $Cs_2CO_3$ (678.01 mg, 2.08 mmol) in DMF (4 mL) was irradiated at 150° C. for 3 hrs. The mixture was cooled. To the mixture was added $Cs_2CO_3$ (293.21 mg, 0.9 mmol) and 2-bromoacetophenone (340 mg, 1.71 mmol). The mixture was stirred for 3 hrs, diluted with EtOAc (120 mL), washed with water (50, 30 mL), brine (30 mL), dried ($Na_2SO_4$), filtered and concentrated in vacuo. The residue was purified by flash column chromatography (0-100% EtOAc/Hept) to provide phenacyl 6-[(2-methyl-4-pyridyl)oxy]chromane-3-carboxylate (239 mg, 66% yield) as a brown oil.

LCMS (ES$^+$, Short): RT 1.40 min, m/z 404.4 [M+H]$^+$ $^1$H NMR (400 MHz, $CDCl_3$) δ: 8.34 (1H, d, J=5.7 Hz), 7.96-7.91 (2H, m), 7.68-7.63 (1H, m), 7.56-7.49 (2H, m), 6.93-6.91 (0.2H, m), 6.90-6.89 (0.8H, m), 6.88-6.85 (1.7H, m), 6.85-6.84 (0.3H, m), 6.68-6.63 (2H, m), 5.45 (2H, d, J=0.9 Hz), 4.64-4.57 (1H, m), 4.33-4.25 (1H, m), 3.33-3.20 (2H, m), 3.18-3.10 (1H, m), 2.51 (3H, s).

Step 2:

A mixture of phenacyl 6-[(2-methyl-4-pyridyl)oxy]chromane-3-carboxylate (230 mg, 0.57 mmol) and $NH_4OAc$ (4.39 g, 57.01 mmol) in AcOH (4 mL) was heated at 120° C. for 5 hrs. The reaction was cooled and added slowly to sat. aq. $NaHCO_3$ (150 mL) and stirred for 1 hr. The aqueous layer was extracted with EtOAc (2×200 mL) and the combiped organic layers were dried ($Na_2SO_4$), filtered, concentrated in vacuo. The residue was purified by flash column chromatography (0-5% MeOH/DCM), partitoned between DCM (50 mL)/sat. aq. $NaHCO_3$ (50 mL), the organic layer was dried (phase separator) and concentrated in vacuo to provide 2-methyl-4-[3-(5-phenyl-1H-imidazol-2-yl)chroman-6-yl]oxy-pyridine (29.3 mg, 13% yield) as a light tan solid.

LCMS: (ES$^+$, Long): RT 2.16 min, m/z 384.0 [M+H]$^+$.

$^1$H NMR shows a mixture of confirmers:

$^1$H NMR (400 MHz, $d_6$-DMSO) δ: 12.31 (0.2H, br s), 12.10 (0.8H, br s), 8.30 (1H, d, J=5.7 Hz), 7.77-7.73 (1.6H, m), 7.66-7.62 (0.4H, m), 7.60 (0.8H, d, J=2.0 Hz), 7.43-7.38 (0.3H, m), 7.36-7.30 (1.7H, m), 7.28 (0.2H, d, J=1.4 Hz), 7.26-7.21 (0.2H, m), 7.19-7.13 (0.8H, m), 7.04-7.00 (1H, m), 6.95-6.88 (2H, m), 6.75 (1H, d, J=2.4 Hz), 6.69 (1H, dd, J=2.4, 5.7 Hz), 4.55-4.49 (1H, m), 4.17-4.09 (1H, m), 3.45-3.36 (1H, m), 3.30-3.20 (1H, m), 3.17-3.07 (1H, m), 2.40 (3H, s).

Example 22: Biological data

In vitro biological evaluation of compounds of the invention was carried out following the procedure detailed below. The procedure provides binding affinity data for the compounds of the invention against B-RAFRAF$^{V600E}$ and C-RAF. The binding affinity is shown in Table 4 below.

LanthaScreen™ Eu kinase binding assay

To determine whether compounds bind to RAF kinases, they are tested in a competition binding assay. The Invitrogen LanthaScreen™ Eu binding assay involves the binding of an Alexa-Fluor® 647-labelled, ATP-competitive kinase tracer to the kinase of interest. A Europium-labelled anti-tag antibody also binds to the kinase of interest. Simultaneous binding of the tracer and the antibody brings them into close proximity and upon excitation at 340 nm, triggers fluorescence resonance energy transfer (FRET) between the Europium donor fluorophore on the antibody and the Alexa Fluor® 647 acceptor on the tracer. The dual emission signal produced can be measured at 665 and 615 nm.

Compounds at a concentration of 3 mM are serially diluted (e.g. 10 μl, 90 μl of 100% dimethyl sulfoxide (DMSO)) seven times in 96-well plates for a total of 8 dilution points. Each DMSO dilution is further diluted 1:100 in kinase buffer (e.g. 5 μl into 495 μl kinase buffer) containing 50 mM HEPES pH 7.5, 10 mM $MgCl_2$, 1 mM EGTA, 0.01% Brij-35.

Each well in a 96-well Optiplate™ (Perkin Elmer 6005569) contains 30 μl of final volume per sample, including 10 μl compound at 3× the desired concentration, providing 10 μM at the final maximum concentration, 10 μl of kinase/antibody mixture at 3× the desired concentration of RAF recombinant kinases and antibody providing 5 nM final concentration of B-RAF$^{V600E}$ kinase (Invitrogen PV3849) and 3 nM final concentration of C-RAF Y340D/Y341D kinase (Invitrogen PV3805) and 2 nM final concentration of Eu-anti-GST antibody (PV5594), and 10 μl of 3× the desired concentration of kinase tracer 178 (Invitrogen PV5593) providing final concentrations of 20 nM tracer for B-RAF$^{V600E}$ kinase and 6 nM tracer for C-RAF kinase. The plates are incubated for 5 hours at room temperature and read on an EnVision plate reader (Perkin Elmer).

All data are analysed using the GraphPad Prism software package. Inhibition of tracer binding to the kinase of interest is assessed by determination of $IC_{50}$ value, which is defined as the concentration of compound which decreased the level of FRET signal measured at 665 nm by 50%.

The results of the in vitro biological binding affinity study of the compounds of the invention are given in Table 3 below. The compounds all show binding affinity against B-RAF$^{V600E}$ mutant and C-RAF. The table shows the B-RAF$^{V600E}$ and C-RAF inhibition activity of compounds of the invention categorised based on the $IC_{50}$ values, the categories being "+", "++" and "+++". The category "+" refers to compounds with an $IC_{50}$ value of greater than 100 nM. The category "++" refers to compounds with an $IC_{50}$ value of 4 nM to 100 nM. The category "+++" refers to compounds with an $IC_{50}$ value of less than 4 nM. Compounds having a designation of "+++" are thus more active against B-RAF$^{V600E}$ and/or C-RAF than compounds having a designation of "++". Similarly, compounds having a designation of "++" are more active against B-RAF and/or C-RAF than compounds having a designation of "+".

TABLE 4

| Example | Name | BRAF$^{V600E}$ binding affinity | CRAF binding affinity |
|---|---|---|---|
| 1 | 5-[3-(1H-benzimidazol-2-yl)chroman-6-yl] oxy-3,4-dihydro-1H-1,8-naphthyridin-2-one | +++ | +++ |
| 2 | 5-[3-(7-chloro-1H-benzimidazol-2-yl] chroman-6-yl]oxy-3,4-dihydro-1H-1,8-naphthyridin-2-one | ++ | ++ |
| 3 | 5-[3-(4-phenyl-1H-imidazol-2-yl)chroman-6-yl]oxy-3,4-dihydro-1H-1,8-naphthyridin-2-one] | +++ | +++ |
| 3A | Enantiomer 1 of 5-[3-(4-phenyl-1H-imidazol-2-yl)chroman-6-yl]oxy-3,4-dihydro-1H-1,8-naphthyridin-2-one] | +++ | +++ |
| 3B | Enantiomer 2 of 5-[3-(4-phenyl-1H-imidazol-2-yl)chroman-6-yl]oxy-3,4-dihydro-1H-1,8-naphthyridin-2-one] | +++ | +++ |
| 4 | 5-[3[4-(4-pyridyl)-1H-imidazol-2-yl] chroman-6-yl]oxy-3,4-dihydro-1H-1,8-naphthyridin-2-one | +++ | +++ |
| 5 | 5-[3-(4-tert-butyl-1H-imidazol-2-yl) chroman-6-yl]oxy-3,4-dihydro-1H-1,8-naphthyridin-2-one | ++ | +++ |
| 6 | 5-[3-[4-(3-thienyl)-1H-imidazol-2-yl] chroman-6-yl]oxy-3,4-dihydro-1H-1,8-naphthyridin-2-one | +++ | +++ |
| 7 | 5-[3-[4-(2-thienyl)-1H-imidazol-2-yl] chroman-6-yl]oxy-3,4-dihydro-1H-1,8-naphthyridin-2-one | +++ | +++ |
| 8 | 5-[3-[5-(2-chlorophenyl)-1H-imidazol-2-yl] chroman-6-yl]oxy-3,4-dihydro-1H-1,8-naphthyridin-2-one | +++ | +++ |
| 9 | 5-[3-[5-(3-chlorophenyl)-1H-imidazol-2-yl] chroman-6-yl]oxy-3,4-dihydro-1H-1,8-naphthyridin-2-one | +++ | +++ |
| 10 | 5-[3-[4-(benzofuran-3-yl)-1H-imidazol-2-yl] chroman-6-yl]oxy-3,4-dihydro-1H-1,8-naphthyridin-2-one | +++ | +++ |
| 11 | 5-[3-[5-(3-pyridyl)-1H-imidazol-2-yl] chroman-6-yl]oxy-3,4-dihydro-1H-1,8-naphthyridin-2-one | +++ | +++ |
| 12 | 5-[3-[5-(4-methylsulfonylphenyl)-1H-imidazol-2-yl]chroman-6-yl]oxy-3,4-dihydro-1H-1,8-naphthyridin-2-one | + | ++ |
| 13 | 5-[3-[5-(4-fluorophenyl)-1H-imidazol-2-yl] chroman-6-yl]oxy-3,4-dihydro-1H-1,8-naphthyridin-2-one | +++ | +++ |
| 14 | 5-[3-[5-(1,3-benzodioxol-5-yl)-1H-imidazol-2-yl]chroman-6-yl]oxy-3,4-dihydro-1H-1,8-naphthyridin-2-one | +++ | +++ |
| 15 | 5-[3-[5-(2,3-dihydro-1,4-benzodioxin-6-yl)-1H-imidazol-2-yl]chroman-6-yl]oxy-3,4-dihydro-1H-1,8-naphthyridin-2-one | ++ | +++ |
| 16 | 5-[[3-(4-phenyl-1H-imidazol-2-yl)-2H-chromen-6-yl]oxy]-3,4-dihydro-1H-1,8-naphthyridin-2-one | ++ | +++ |
| 17 | 5-[3-(3-phenyl-1,2,4-oxadiazol-5-yl) chroman-6-yl]oxy-3,4-dihydro-1H-1,8-naphthyridin-2-one | ++ | ++ |
| 18 | 5-[3-(5-phenyl-1H-pyrazol-3-yl) chroman-6-yl]oxy-3,4-dihydro-1H-1,8-naphthyridin-2-one | +++ | +++ |
| 19 | 5-[[(3S)-3-(4-phenyl-1H-imidazol-2-yl)-2,3-dihydro-1,4-benzodioxin-6-yl]oxy]-3,4-dihydro-1H-1,8-naphthyridin-2-one | +++ | +++ |
| 20 | 5-[[(3R)-3-(4-phenyl-1H-imidazol-2-yl)-2,3-dihydro-1,4-benzodioxin-6-yl]oxy]-3,4-dihydro-1H-1,8-naphthyridin-2-one | +++ | +++ |
| 21 | 2-Methyl-4-[3-(5-phenyl-1H-imidazol-2-yl) chroman-6-yl]oxy-pyridine | ++ | ++ |

Examples of compounds of the invention with values for their $IC_{50}$ are given in Table 5 below.

TABLE 5

| Example | Name | BRAF$^{V600E}$ binding affinity $IC_{50}$ (nM) | CRAF binding affinity $IC_{50}$ (nM) |
|---|---|---|---|
| 3 | 5-[3-(4-phenyl-1H-imidazol-2-yl) chroman-6-yl]oxy-3,4-dihydro-1H-1,8-naphthyridin-2-one] | 0.8 | 0.6 |
| 3A | Enantiomer 1 of 5-[3-(4-phenyl-1H-imidazol-2-yl)chroman-6-yl]oxy-3,4-dihydro-1H-1,8-naphthyridin-2-one] | 1.5 | 1.0 |
| 3B | Enantiomer 2 of 5-[3-(4-phenyl-1H-imidazol-2-yl)chroman-6-yl]oxy-3,4-dihydro-1H-1,8-naphthyridin-2-one] | 1.4 | 0.8 |
| 6 | 5-[3-[4-(3-thienyl)-1H-imidazol-2-yl] chroman-6-yl]oxy-3,4-dihydro-1H-1,8-naphthyridin-2-one | 1.0 | 0.4 |
| 7 | 5-[3-[4-(2-thienyl)-1H-imidazol-2-yl] chroman-6-yl]oxy-3,4-dihydro-1H-1,8-naphthyridin-2-one | 1.1 | 0.5 |

Compounds of the invention were selected to be tested in an AlphaScreen® SureFire® pERK1/2 assay to assess the compounds cellular activity.

WiDr AlphaScreen® SureFire® pERK1/2 Cellular Assay

The human WiDr colorectal cell line endogenously expresses the B-RAF$^{V600E}$ mutation, which leads to constitutive activation of the MAP kinase pathway and phosphorylation of ERK in the absence of ligands. To determine whether compounds inhibit constitutive ERK phosphorylation in WiDr cells, they are tested using AlphaScreen® SureFire® technology (Perkin Elmer ERK1/2 p-T202/Y204 assay kit TGRES10K). On day 1, WiDr cells (ATCC CRL-218™) are counted, centrifuged and resuspended in growth media (Minimum essential medium containing 1 g/L D-glucose and 2 mM L-glutamine (Gibco 31095), 10% fetal bovine serum (VWR S061)). The cells are plated, 200 μl in each well of 96-well culture dish (Corning 3585) to a final cell density of 80,000 cells per well and incubated at 37° C. in 5% $CO_2$ overnight.

On day 2, compounds at a concentration of 6 mM are serially diluted 10 μl into 90 μl of 100% dimethyl sulfoxide (DMSO) six times in 96-well plates for a total of 7 dilution points. Each dilution and a DMSO control are further diluted 1:200 (e.g. 5 μl into 995 μl minimum essential medium+ 0.1% fetal bovine serum). The media is removed and 100 μl compound dilution or control in minimum essential medium+0.1% fetal bovine serum is added to triplicate wells containing cells, providing 30 μM compound at the maximum concentration. The cells are treated for 1 hour or 24 hours at 37° C. The treatment is then removed and the cells are incubated with lysis buffer containing phosphatase inhibitors for 10 minutes at room temperature. Cell lysates are transferred to a 96-well Optiplate™ (Perkin Elmer 6005569) and incubated with anti-mouse IgG acceptor beads, a biotinylated anti-ERK1/2 rabbit antibody recognising both phosphorylated and non-phosphorylated ERK1/2, a mouse antibody targeted to the Thr202/Tyr204 epitope and recognising phosphorylated ERK proteins only, and streptavidin-coated donor beads. The biotinylated antibody binds to the streptavidin-coated donor beads and the phopsho-ERK1/2 antibody binds to the acceptor beads. Plates are read on an EnVision reader (Perkin Elmer) and excitation of the beads at 680 nm with a laser induces the release of singlet oxygen molecules from the donor beads that triggers energy transfer to the acceptor beads in close proximity, producing a signal that can be measured at 570 nm. Both antibodies bind to phosphorylated ERK proteins, bringing the donor and acceptor beads into close proximity.

All data are analysed using the GraphPad Prism software package. Inhibition of ERK phosphorylation is assessed by determination of $IC_{50}$ value, which is defined as the concentration of compound which decreased the level of phosphorylated ERK proteins by 50%.

The results of WiDr AlphaScreen SureFire pERK1/2 cellular assay are given in Table 6 below. The compounds tested all showed activity within a cell. The activity of the compounds of the invention has been categorised based on the $IC_{50}$ values, the categories being "+", "++" and "+++" The category "+" refers to compounds with an $IC_{50}$ value of greater than 300 nM. The category "++" refers to compounds with an $IC_{50}$ value of 70 nM to 300 nM. The category "+++" refers to compounds with an $IC_{50}$ value of less than 70 nM.

TABLE 6

| Example | Name | WiDr pERK inhibition category 1 hr | WiDr pERK inhibition category 24 hrs |
|---|---|---|---|
| 3 | 5-[3-(4-phenyl-1H-imidazol-2-yl)chroman-6-yl]oxy-3,4-dihydro-1H-1,8-naphthyridin-2-one] | ++ | + |
| 3A | Enantiomer 1 of 5-[3-(4-phenyl-1H-imidazol-2-yl)chroman-6-yl]oxy-3,4-dihydro-1H-1,8-naphthyridin-2-one] | +++ | + |
| 3B | Enantiomer 2 of 5-[3-(4-phenyl-1H-imidazol-2-yl)chroman-6-yl]oxy-3,4-dihydro-1H-1,8-naphthyridin-2-one] | ++ | + |
| 19 | 5-[[(3S)-3-(4-phenyl-1H-imidazol-2-yl)-2,3-dihydro-1,4-benzodioxin-6-yl]oxy]-3,4-dihydro-1H-1,8-naphthyridin-2-one | ++ | + |
| 20 | 5-[[(3R)-3-(4-phenyl-1H-imidazol-2-yl)-2,3-dihydro-1,4-benzodioxin-6-yl]oxy]-3,4-dihydro-1H-1,8-naphthyridin-2-one | ++ | + |

Examples of compounds of the invention with values for their $IC_{50}$ are given in Table 7 below.

TABLE 7

| Example | Name | WiDr pERK inhibition $IC_{50}$ (nM) 1 hr | WiDr pERK inhibition $IC_{50}$ (nM) 24 hrs |
|---|---|---|---|
| 3 | 5-[3-(4-phenyl-1H-imidazol-2-yl)chroman-6-yl]oxy-3,4-dihydro-1H-1,8-naphthyridin-2-one] | 100 | 671 |
| 3A | Enantiomer 1 of 5-[3-(4-phenyl-1H-imidazol-2-yl)chroman-6-yl]oxy-3,4-dihydro-1H-1,8-naphthyridin-2-one] | 32 | 562 |
| 3B | Enantiomer 2 of 5-[3-(4-phenyl-1H-imidazol-2-yl)chroman-6-yl]oxy-3,4-dihydro-1H-1,8-naphthyridin-2-one] | 115 | 416 |

A375 AlphaScreen SureFire pERK1/2 Cellular Assay

The human A375 malignant melanoma cell line endogenously expresses the B-RAF$^{V600E}$ mutation, which leads to constitutive activation of the MAP kinase pathway and phosphorylation of ERK in the absence of ligands. To determine whether compounds inhibit constitutive ERK phosphorylation in A375 cells, they are tested using AlphaScreen® SureFire® technology (Perkin Elmer ERK1/2 p-T202/Y204 assay kit TGRES10K). On day 1, A375 cells (ATCC CRL-1619) are counted, centrifuged and resuspended in growth media (Dulbecco's modified Eagle's medium containing 4.5 g/L D-glucose (Gibco 41965), 10% fetal bovine serum (VWR S061) and 4 mM L-glutamine (Sigma G7513)). The cells are plated, 200 μl in each well of 96-well culture dish (Corning 3585) to a final cell density of 60,000 cells per well and incubated at 37° C. in 5% $CO_2$ overnight.

On day 2, compounds at a concentration of 6 mM are serially diluted 10 μl into 90 μl of 100% dimethyl sulfoxide (DMSO) six times in 96-well plates for a total of 7 dilution points. Each dilution and a DMSO control are further diluted 1:200 (e.g. 5 μl into 995 μl serum-free growth media). The media is removed and 50 μl compound dilution or control in serum-free media is added to triplicate wells containing cells, providing 30 μM compound at the maximum concentration. The cells are treated for 30 minutes at room temperature. The treatment is then removed and the cells are incubated with lysis buffer containing phosphatase inhibitors for 10 minutes at room temperature. Cell lysates are transferred to a 96-well Optiplate™ (Perkin Elmer 6005569) and incubated with anti-mouse IgG acceptor beads, a biotinylated anti-ERK1/2 rabbit antibody recognising both phosphorylated and non-phosphorylated ERK1/2, a mouse antibody targeted to the Thr202/Tyr204 epitope and recognising phosphorylated ERK proteins only, and streptavidin-coated donor beads. The biotinylated antibody binds to the streptavidin-coated donor beads and the phopsho-ERK1/2 antibody binds to the acceptor beads. Plates are read on an EnVision reader (Perkin Elmer) and excitation of the beads at 680 nm with a laser induces the release of singlet oxygen molecules from the donor beads that trigger energy transfer to the acceptor beads in close proximity, producing a signal that can be measured at 570 nm. Both antibodies bind to phosphorylated ERK proteins, bringing the donor and acceptor beads into close proximity.

All data are analysed using the GraphPad Prism software package. Inhibition of ERK phosphorylation is assessed by determination of $IC_{50}$ value, which is defined as the concentration of compound which decreased the level of phosphorylated ERK proteins by 50%.

The results of AlphaScreen SureFire pERK1/2 cellular assay are given in Table 8 below. The compounds tested all showed activity within a cell. The activity of the compounds of the invention has been categorised based on the $IC_{50}$ values, the categories being "+", "++" and "+++" The category "+" refers to compounds with an $IC_{50}$ value of greater than 300 nM. The category "++" refers to compounds with an $IC_{50}$ value of 70 nM to 300 nM. The category "+++" refers to compounds with an $IC_{50}$ value of less than 70 nM.

TABLE 8

| Example | Name | A375 pERK inhibition category |
|---|---|---|
| 2 | 5-[3-(7-chloro-1H-benzimidazol-2-yl)chroman-6-yl]oxy-3,4-dihydro-1H-1,8-naphthyridin-2-one | ++ |
| 3 | 5-[3-(4-phenyl-1H-imidazol-2-yl)chroman-6-yl]oxy-3,4-dihydro-1H-1,8-naphthyridin-2-one] | +++ |
| 3A | Enantiomer 1 of 5-[3-(4-phenyl-1H-imidazol-2-yl)chroman-6-yl]oxy-3,4-dihydro-1H-1,8-naphthyridin-2-one] | +++ |
| 3B | Enantiomer 2 of 5-[3-(4-phenyl-1H-imidazol-2-yl)chroman-6-yl]oxy-3,4-dihydro-1H-1,8-naphthyridin-2-one] | ++ |
| 4 | 5-[3-[4-(4-pyridyl)-1H-imidazol-2-yl]chroman-6-yl]oxy-3,4-dihydro-1H-1,8-naphthyridin-2-one | + |
| 6 | 5-[3-[4-(3-thienyl)-1H-imidazol-2-yl]chroman-6-yl]oxy-3,4-dihydro-1H-1,8-naphthyridin-2-one | +++ |
| 7 | 5-[3-[4-(2-thienyl)-1H-imidazol-2-yl]chroman-6-yl]oxy-3,4-dihydro-1H-1,8-naphthyridin-2-one | +++ |
| 16 | 5-[[3-[4-phenyl-1H-imidazol-2-yl)-2H-chromen-6-yl]oxy]-3,4-dihydro-1H-1,8-naphthyridin-2-one | + |
| 18 | 5-[3-(5-phenyl-1H-pyrazol-3-yl)chroman-6-yl]oxy-3,4-dihydro-1H-1,8-naphthyridin-2-one | + |
| 19 | 5-[[3S)-3-[4-phenyl-1H-imidazol-2-yl)-2,3-dihydro-1,4-benzodioxin-6-yl]oxy]-3,4-dihydro-1H-1,8-naphthyridin-2-one | ++ |
| 20 | 5-[[(3R)-3-[4-phenyl-1H-imidazol-2-yl)-2,3-dihydro-1,4-benzodioxin-6-yl]oxy]-3,4-dihydro-1H-1,8-naphthyridin-2-one | ++ |

Examples of compounds of the invention with values for their $IC_{50}$ are given in Table 9 below.

TABLE 9

| Example | Name | A375 pERK inhibition $IC_{50}$ (nM) |
|---|---|---|
| 3 | 5-[3-(4-phenyl-1H-imidazol-2-yl)chroman-6-yl]oxy-3,4-dihydro-1H-1,8-naphthyridin-2-one] | 9.8 |
| 3A | Enantiomer 1 of 5-[3-(4-phenyl-1H-imidazol-2-yl)chroman-6-yl]oxy-3,4-dihydro-1H-1,8-naphthyridin-2-one] | 12.0 |
| 3B | Enantiomer 2 of 5-[3-(4-phenyl-1H-imidazol-2-yl)chroman-6-yl]oxy-3,4-dihydro-1H-1,8-naphthyridin-2-one] | 112 |
| 6 | 5-[3-[4-(3-thienyl)-1H-imidazol-2-yl]chroman-6-yl]oxy-3,4-dihydro-1H-1,8-naphthyridin-2-one | 23.4 |
| 19 | 5-[[(3S)-3-(4-phenyl-1H-imidazol-2-yl)-2,3-dihydro-1,4-benzodioxin-6-yl]oxy]-3,4-dihydro-1H-1,8-naphthyridin-2-one | 155 |
| 20 | 5-[[(3R)-3-(4-phenyl-1H-imidazol-2-yl)-2,3-dihydro-1,4-benzodioxin-6-yl]oxy]-3,4-dihydro-1H-1,8-naphthyridin-2-one | 282 |

IPC-298 AlphaScreen SureFire pERK1/2 Cellular Assay

The human IPC-298 melanoma cell line endogenously expresses the $NRAS^{Q61L}$ mutation leading to constitutive activation of the MAPK pathway and phosphorylation of ERK via C-RAF in the absence of ligands. To determine whether compounds inhibit C-RAF-mediated ERK activation in $B\text{-}RAF^{WT}$ IPC-298 cells, they are tested using AlphaScreen® SureFire® technology (Perkin Elmer ERK1/2 p-T202/Y204 assay kit TGRES10K). On day 1, IPC-298 cells (DSMZ ACC-251) are counted, centrifuged and resuspended in growth medium (RPMI 1640 containing 2 g/L D-glucose (Gibco 31870), 10% fetal bovine serum (VWR S061) and 2 mM L-glutamine (Sigma G7513). The cells are plated, 100 uL in each well of 96 well culture dish (Corning 3585) to a final cell density of 40,000 cells per well and incubated at 37° C. in 5% $CO_2$ overnight.

On day 2, compounds at a concentration of 6 mM are serially diluted 5 μl into 45 μl of 100% dimethyl sulfoxide (DMSO) six times in 96-well plates for a total of 7 dilution points. Each dilution and a DMSO control are further diluted 1:200 (e.g. 5 μl into 995 μl serum-free RPMI 1640 medium). The media is removed and 100 μl compound dilution or control in serum-free RPMI 1640 medium is added to triplicate wells containing cells, providing 30 μM compound at the maximum concentration. The cells are treated for 1 hour at 37° C. in 5% $CO_2$. The treatment is then removed and the cells are incubated with lysis buffer containing phosphatase inhibitors for 10 minutes at room temperature with gentle shaking. Cell lysates are transferred to a 96-well Optiplate™ (Perkin Elmer 6005569) and incubated with anti-mouse IgG acceptor beads, a biotinylated anti-ERK1/2 rabbit antibody recognising both phosphorylated and non-phosphorylated ERK1/2, a mouse antibody targeted to the Thr202/Tyr204 epitope and recognising phosphorylated ERK proteins only, and streptavidin-coated donor beads. The biotinylated antibody binds to the streptavidin-coated donor beads and the phopsho-ERK1/2 antibody binds to the acceptor beads. Plates are read on an EnVision reader (Perkin Elmer) and excitation of the beads at 680 nm with a laser induces the release of singlet oxygen molecules from the donor beads that triggers energy transfer to the acceptor beads in close proximity, producing a signal that can be measured at 570 nm. Both antibodies bind to phosphorylated ERK proteins, bringing the donor and acceptor beads into close proximity.

All data are analysed using the GraphPad Prism software package. Activation of ERK phosphorylation is expressed as a percentage of activation relative to the reference compound, Dabrafenib.

A representative example of the results of IPC-298 AlphaScreen SureFire pERK1/2 cellular assay is given in FIG. 1. Example 3 (5-[3-(4-phenyl-1H-imidazol-2-yl)chroman-6-yl]oxy-3,4 -dihydro-1H-1,8-naphthyridin-2 -one]) shows reduced paradoxical activation of MAPK pathway in comparison to Dabrafenib.

In total nine compounds of the invention were tested in the IPC-298 AlphaScreen SureFire pERK1/2 cellular assay. The compounds were examples 3, 3A, 3B, 4, 6, 7, 18, 19 and 20. Each compound yielded similar results to that of FIG. 1 and showed reduced paradoxical activity Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The reader's attention is directed to all papers and documents which are filed concurrently with or previous to this specification in connection with this application and which are open to public inspection with this specification, and the contents of all such papers and documents are incorporated herein by reference.

The invention claimed is:

1. A compound of formula (I):

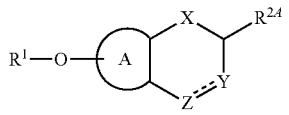

(I)

or a pharmaceutically acceptable salt thereof;

wherein:

the bond between Y and Z is a single bond or a double bond;

A is a phenyl ring;

$R^1$ is a substituted or unsubstituted heterocyclic moiety which either contains 5 or 6 atoms in a single ring or 8, 9, 10 or 11 atoms in a fused bicyclic ring system, when substituted $R^1$ contains 1 to 4 substituents independently selected from the group consisting of halo, —$OR^A$, —$NR^AR^B$, =O, —$OC(O)R^C$, —$C(O)R^C$, —$C(O)OR^A$, —$NR^AC(O)R^C$, —$C(O)NR^AR^B$, —$SO_2R^C$, —$SOR^C$, —$NR^ASO_2R^C$, —$SO_2NR^AR^B$, —CN, $C_{1-4}$ alkyl, $C_{1-4}$ haloalkyl and $C_{3-6}$ cycloalkyl;

X is O;

Y is —CHW and the bond between Y and Z is a single bond; or Y is —CW and the bond between Y and Z is a double bond;

W represents -$het^1$-$R^3$ or -$het^2$, in which $het^1$ is an optionally further substituted five or six membered cycloalkyl ring or heterocyclic ring, and $het^2$ is a carbocyclic or heterocyclic ring system containing 8, 9 or 10 atoms in a fused bicyclic ring system; in which $het^2$ is unsubstituted or substituted; and $het^1$, when further substituted, and $het^2$ when substituted contain 1 or 2 substituents independently selected at each occurrence from halo, —$OR^A$, —CN, $C_{1-4}$ alkyl, $C_{1-4}$ haloalkyl, $C_{3-6}$ cycloalkyl, in which the aforementioned alkyl, haloalkyl and cycloalkyl groups are themselves unsubstituted or substituted with 1 to 3 groups independently selected from the group consisting of —$OR^A$, —CN, and —$NR^AR^B$;

Z is O, or —$CH_2$ and the bond between Y and Z is a single bond: or Z is —CH and the bond between Y and Z is a double bond;

$R^{2A}$ is selected from the group consisting of H, halo, —$OR^A$, —CN, $C_{1-4}$ alkyl, $C_{1-4}$ haloalkyl and $C_{3-6}$ cycloalkyl;

$R^3$ is selected from the group consisting of substituted or unsubstituted: $C_{1-6}$ alkyl, $C_{1-6}$ haloalkyl, a carbocyclic moiety or a heterocyclic moiety, wherein the carbocyclic moiety and heterocyclic moiety either contain 5 or 6 atoms in a single ring or 8, 9 or 10 atoms in a fused bicyclic ring system, and when substituted $R^3$ contains 1 to 4 substituents independently selected from the group consisting of halo, —$OR^A$, —$NR^AR^B$, —$SO_2R^C$, —$SOR^C$, CN, $C_{1-4}$ alkyl, $C_{1-4}$ haloalkyl, $C_{3-6}$ cycloalkyl in which the aforementioned alkyl, haloalkyl and cycloalkyl groups are themselves unsubstituted or substituted with 1 to 3 groups independently selected from the group consisting of —$OR^A$, —CN, —$SOR^C$ and —$NR^AR^B$;

$R^A$ and $R^B$ are each independently selected from the group consisting of H, $C_{1-4}$ alkyl and $C_{1-4}$ haloalkyl; and $R^C$ is selected from the group consisting of $C_{1-4}$ alkyl and $C_{1-4}$ haloalkyl.

2. The compound of claim 1, wherein Z is O; and Y is —CHW.

3. The compound of claim 1, wherein Z is —$CH_2$; and Y is —CHW.

4. The compound of claim 1, wherein Z is —CH; and Y is —CW.

5. The compound of claim 1, wherein $R^1$ is a substituted or unsubstituted heterocyclic moiety which either contains 6 atoms in a single ring or 10 atoms in a fused bicyclic ring system.

6. The compound of claim 1, wherein $R^1$ is selected from the group consisting of substituted or unsubstituted: pyridyl, pyridazinyl, pyrimidinyl, pyrazinyl, quinolinyl, tetrahydroquinolinyl, dihydroquinolinyl, quinolinone-yl, tetrahydroquinolinone-yl, dihydroquinolinone-yl, isoquinolinyl, tetrahydroisoquinolinyl, dihydroisoquinolinyl, isoquinolinoneyl, tetrahydroisoquinolinone-yl, dihydroisoquinolinone-yl, napthyridinyl, oxo-napthyridinyl, dihydronappthyridinyl, tetrahydronaphthyridinyl, oxo-tetrahydronaphthyridinyl, and oxo-dihydro-H-naphthyridinyl.

7. The compound of claim 6, wherein $R^1$ is substituted or unsubstituted pyridyl or substituted or unsubstituted oxodihydro-H-naphthyridinyl.

8. The compound of claim 1, wherein

W represents -$het^1$-$R^3$ or -$het^2$, wherein $het^1$ is represented by a group selected from the group consisting of substituted or unsubstituted: $C_{5-6}$ cycloalkyl, $C_{5-6}$ heterocycloalkyl and $C_{5-6}$ heteroaryl, and $het^2$ is represented by a group selected from the group consisting of substituted or unsubstituted: $C_{8-10}$ cycloalkyl, $C_{10}$ aryl, $C_{8-10}$ heterocycloalkyl and $C_{8-10}$ heteroaryl.

9. The compound of claim 1, wherein $het^1$ is represented by substituted or unsubstituted: pyrazole, imidazole or oxadiazole; and $het^2$ is represented by substituted or unsubstituted benzimidazole.

10. The compound of claim 1, wherein $R^3$ is selected from the group consisting of $C_{1-6}$ alkyl, a substituted or unsubstituted carbocyclic moiety or a substituted or unsubstituted heterocyclic moiety, wherein the carbocyclic moiety and heterocyclic moiety either contain 5 or 6 atoms in a single aromatic ring or 8, 9 or 10 atoms in a fused bicyclic ring system, wherein one ring of the bicyclic ring system is aromatic.

11. The compound of claim 10, wherein $R^3$ is selected from the group consisting of a substituted or unsubstituted: iso-propyl, tert-butyl, phenyl, pyridyl, pyridazinyl, pyrimidinyl, pyrazinyl pyrrolyl, furanyl, thiophenyl, pyrazolyl, imidazolyl, oxazolyl, isoxazolyl, thiazolyl, isothiazolyl, oxadiazolyl, thiadiazolyl, triazolyl, indolinyl, isoindolinyl, benzodioxanyl, benzofuranyl, isobenzofuranyl, benzothiophenyl, isobenzothiophenyl, benzodioxolanyl, indazolyl, indazolinyl, benzimidazolyl, benzimidazolinyl, benzthiazolyl, benzoisothiazol, chromanyl, isochromanyl, tetralinyl, quinolinyl, isoquinolinyl, tetrahydroquinolinyl, tetrahydroisoquinolinyl and tetrahydroquinoxalinyl.

12. The compound of claim 1, wherein $R^A$ and $R^B$ are each independently H, methyl, ethyl or trifluoromethyl; and $R^C$ is methyl, ethyl or trifluoromethyl.

13. The compound of claim 12, wherein $R^A$ and $R^B$ are H; $R^A$ and $R^B$ are methyl; or $R^A$ is H and $R^B$ is methyl and $R^C$ is methyl.

14. The compound of claim 1, wherein the compound of formula (I) is selected from the group consisting of:

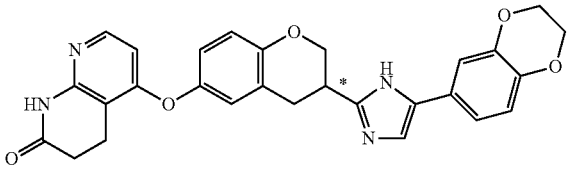

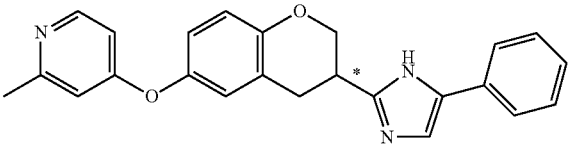

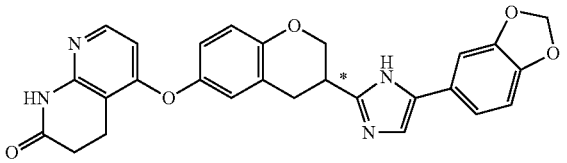

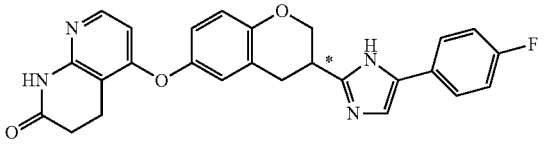

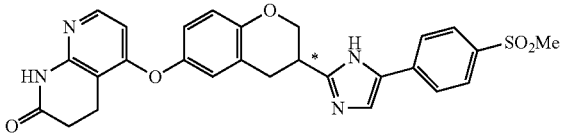

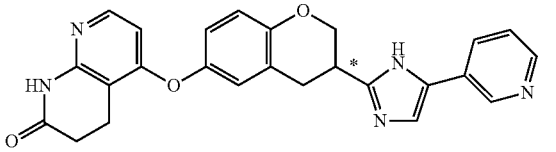

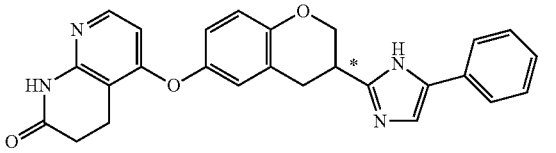

-continued

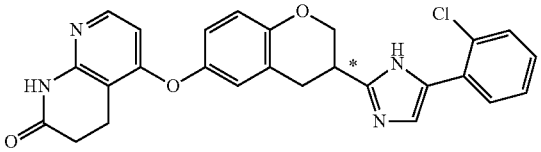

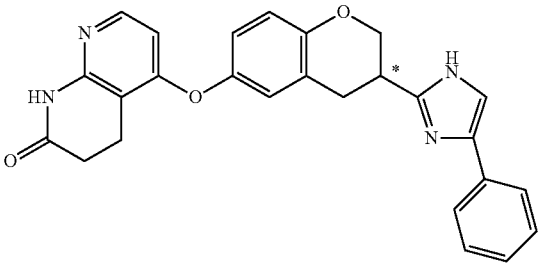

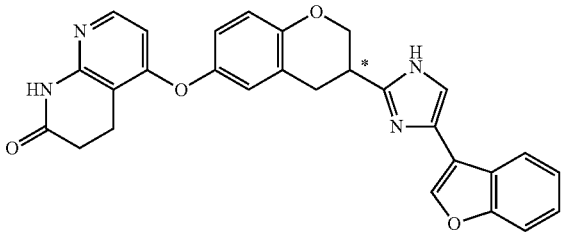

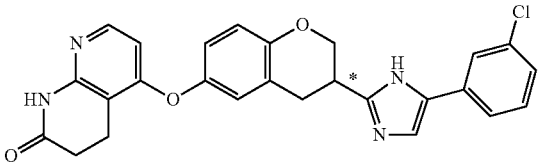

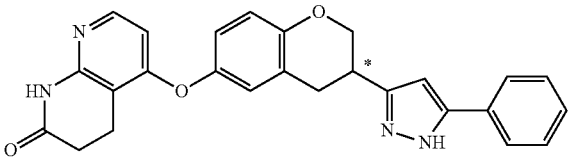

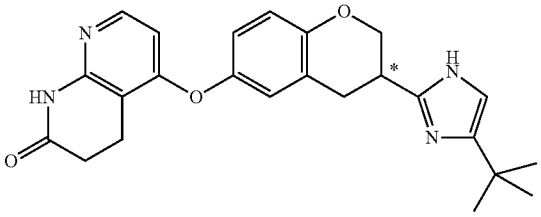

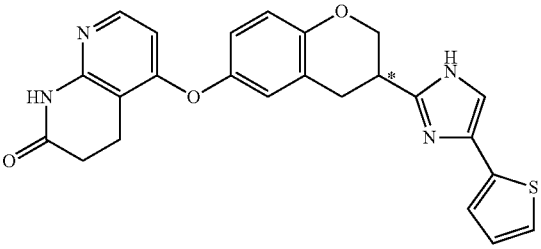

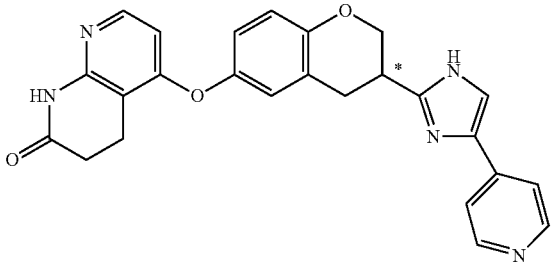

-continued

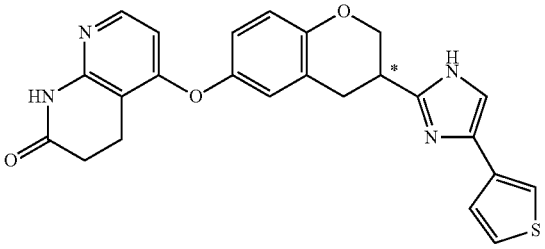

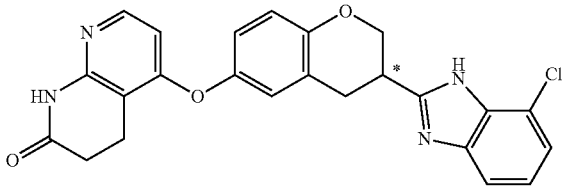

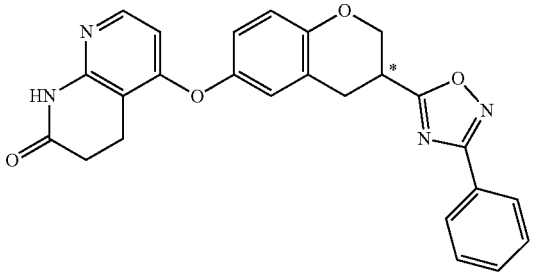

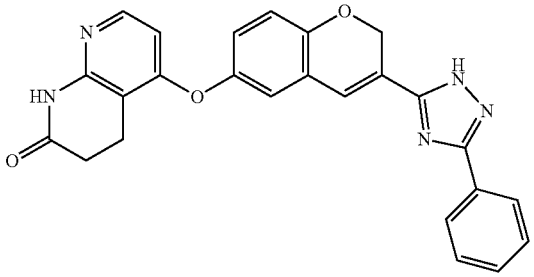

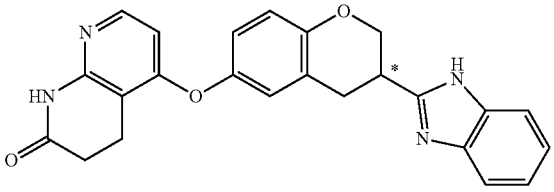

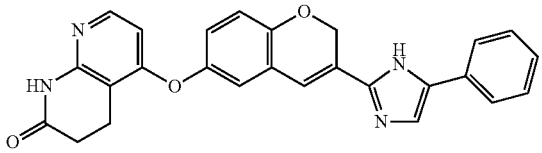

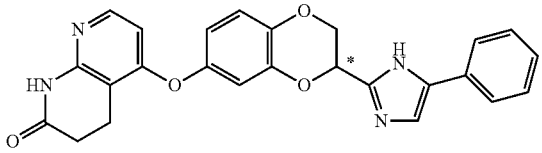

and

-continued

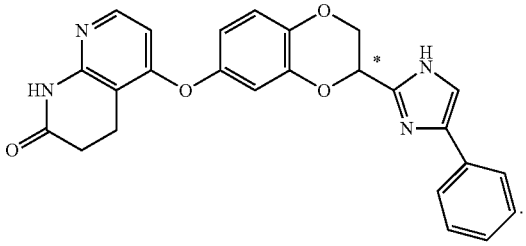

15. The compound of claim 14, wherein a * symbol indicates a chiral centre; and the chiral centre relates to a single enantiomer that has either a (R)-configuration or a (S)-configuration.

16. The compound of claim 1, wherein the compound is a pharmaceutically acceptable salt thereof.

17. A method of treatment of a condition which is modulated by RAF kinases, wherein the condition is selected from the group consisting of cancer, sarcoma, melanoma, skin cancer, haematological tumors, lymphoma, carcinoma and leukemia, wherein the method comprises administering to a patient in need thereof a therapeutic amount of a compound of formula (I):

(I)

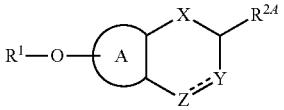

wherein:

the bond between Y and Z is a single bond or a double bond;

A is a phenyl ring;

$R^1$ is a substituted or unsubstituted heterocyclic moiety which either contains 5 or 6 atoms in a single ring or 8, 9, 10 or 11 atoms in a fused bicyclic ring system, when substituted $R^1$ contains 1 to 4 substituents independently selected from the group consisting of halo, —$OR^A$, —$NR^AR^B$, =O, —$OC(O)R^C$, —$C(O)R^C$, —$C(O)OR^A$, —$NR^AC(O)R^C$, —$C(O)NR^AR^B$, —$SO_2R^C$, —$SOR^C$, —$NR^ASO_2R^C$, —$SO_2NR^AR^B$, —CN, $C_{1-4}$ alkyl, $C_{1-4}$ haloalkyl and $C_{3-6}$ cycloalkyl;

X is O;

Y is —CHW and the bond between Y and Z is a single bond; or Y is —CW and the bond between Y and Z is a double bond;

W represents -$het^1$-$R^3$ or -$het^2$, in which $het^1$ is an optionally further substituted five or six membered cycloalkyl ring or heterocyclic ring, and $het^2$ is a carbocyclic or heterocyclic ring system containing 8, 9 or 10 atoms in a fused bicyclic ring system; in which $het^2$ is unsubstituted or substituted; and $het^1$, when further substituted, and $het^2$ when substituted contain 1 or 2 substituents independently selected at each occurrence from halo, —$OR^A$, —CN, $C_{1-4}$ alkyl, $C_{1-4}$ haloalkyl, $C_{3-6}$ cycloalkyl, in which the aforementioned alkyl, haloalkyl and cycloalkyl groups are themselves unsubstituted or substituted with 1 to 3 groups independently selected from the group consisting of —$OR^A$, —CN, and —$NR^AR^B$;

Z is O, or —$CH_2$ and the bond between Y and Z is a single bond: or Z is —CH and the bond between Y and Z is a double bond;

$R^{2A}$ is selected from the group consisting of H, halo, —$OR^A$, —CN, $C_{1-4}$ alkyl, $C_{1-4}$ haloalkyl and $C_{3-6}$ cycloalkyl;

$R^3$ is selected from the group consisting of substituted or unsubstituted: $C_{1-6}$ alkyl, $C_{1-6}$ haloalkyl, a carbocyclic moiety or a heterocyclic moiety, wherein the carbocyclic moiety and heterocyclic moiety either contain 5 or 6 atoms in a single ring or 8, 9 or 10 atoms in a fused bicyclic ring system, and when substituted $R^3$ contains 1 to 4 substituents independently selected from the group consisting of halo, —$OR^A$, —$NR^AR^B$, —$SO_2R^C$, —$SOR^C$, —CN, $C_{1-4}$ alkyl, $C_{1-4}$ haloalkyl, $C_{3-6}$ cycloalkyl in which the aforementioned alkyl, haloalkyl and cycloalkyl groups are themselves unsubstituted or substituted with 1 to 3 groups independently selected from the group consisting of —$OR^A$, —CN, —$SOR^C$ and —$NR^AR^B$;

$R^A$ and $R^B$ are each independently selected from H, $C_{1-4}$ alkyl and $C_{1-4}$ haloalkyl; and $R^C$ is selected from $C_{1-4}$ alkyl and $C_{1-4}$ haloalkyl.

18. The method of claim 17, wherein the condition treatable by the inhibition of Raf kinases is the group consisting of Barret's adenocarcinoma; biliary tract carcinomas; breast cancer; cervical cancer; cholangiocarcinoma; central nervous system tumors; primary CNS tumors; glioblastomas, astrocytomas; glioblastoma multiforme; ependymomas; seconday CNS tumors (metastases to the central nervous system of tumors originating outside of the central nervous system); brain tumors; brain metastases; colorectal cancer; large intestinal colon carcinoma; gastric cancer; carcinoma of the head and neck; squamous cell carcinoma of the head and neck; acute lymphoblastic leukemia; acute myelogenous leukemia (AML); myelodysplastic syndromes; chronic myelogenous leukemia; Hodgkin's lymphoma; non-Hodgkin's lymphoma; megakaryoblastic leukemia; multiple myeloma; erythroleukemia; hepatocellular carcinoma; lung cancer; small cell lung cancer; non-small cell lung cancer; ovarian cancer; endometrial cancer; pancreatic cancer; pituitary adenoma; prostate cancer; renal cancer; metastatic melanoma and thyroid cancers.

19. The method of claim 17, wherein the condition is colorectal cancer or melanoma.

20. The method of claim 17, further comprising administering simultaneously, sequentially or separately a therapeutic amount of an anti-tumour agent.

21. A pharmaceutical composition, wherein the composition comprises a compound of claim 1; and one or more pharmaceutically acceptable excipients.

*22. The compound of claim 1, wherein the compound of formula (I) is*

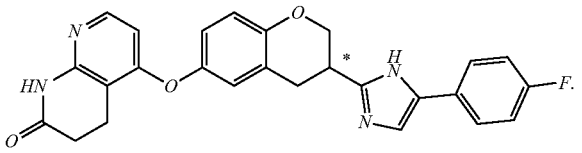

*23. The compound of claim 1, wherein the compound of formula (I) is*

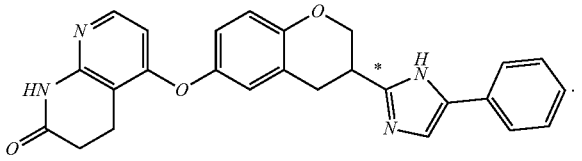

*24. The compound of claim 1, wherein the compound of formula (I) is*

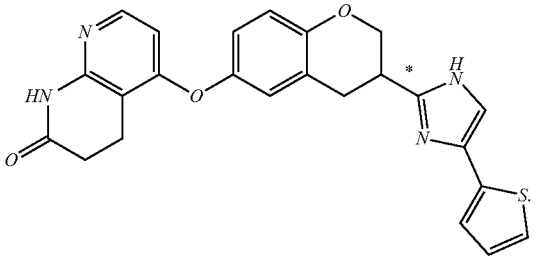

* * * * *